United States Patent
Hu et al.

(10) Patent No.: US 9,783,524 B2
(45) Date of Patent: Oct. 10, 2017

(54) PROTEIN TYROSINE KINASE MODULATORS AND METHODS OF USE

(71) Applicant: BETTA PHARMACEUTICALS CO., LTD., Yuhang, Hangzhou, Zhejiang (CN)

(72) Inventors: Shaojing Hu, Beijing (CN); Xiangyong Liu, Beijing (CN); Jinlong Bai, Beijing (CN); Wei Long, Beijing (CN)

(73) Assignee: BETTA PHARMACEUTICALS CO., LTD., Yuhang, Hangzhou, Zhejiang (CN)

( * ) Notice: Subject to any disclaimer, the term of this patent is extended or adjusted under 35 U.S.C. 154(b) by 0 days.

(21) Appl. No.: 14/903,369

(22) PCT Filed: Jul. 11, 2014

(86) PCT No.: PCT/CN2014/082084
§ 371 (c)(1),
(2) Date: Jan. 7, 2016

(87) PCT Pub. No.: WO2015/003658
PCT Pub. Date: Jan. 15, 2015

(65) Prior Publication Data
US 2016/0145237 A1 May 26, 2016

(30) Foreign Application Priority Data

Jul. 11, 2013 (WO) ................ PCT/CN2013/079232

(51) Int. Cl.
| | | |
|---|---|---|
| *C07D 401/12* | (2006.01) |
| *C07D 401/14* | (2006.01) |
| *C07D 405/12* | (2006.01) |
| *C07D 239/48* | (2006.01) |
| *C07D 403/12* | (2006.01) |
| *C07D 413/12* | (2006.01) |

(52) U.S. Cl.
CPC ......... *C07D 401/12* (2013.01); *C07D 239/48* (2013.01); *C07D 401/14* (2013.01); *C07D 403/12* (2013.01); *C07D 405/12* (2013.01); *C07D 413/12* (2013.01)

(58) Field of Classification Search
CPC .. C07D 401/12; C07D 413/12; C07D 403/12; C07D 239/48; C07D 405/12; C07D 401/14
See application file for complete search history.

(56) References Cited

FOREIGN PATENT DOCUMENTS

| WO | WO 2004/080980 A1 | 9/2004 |
|---|---|---|
| WO | WO 2005/016894 A1 | 2/2005 |
| WO | WO 2008/118823 A2 | 10/2008 |
| WO | WO 2009/158571 A1 | 12/2009 |
| WO | WO 2010/058030 A1 | 5/2010 |
| WO | WO 2011/140338 A1 | 11/2011 |
| WO | WO 2012/106540 A1 | 8/2012 |

OTHER PUBLICATIONS

Walter; "Discovery of a Mutant-Selective Covalent Inhibitor of EGFR that Overcomes T790M Mediated Resistance in NSCLC"; Cancer Discovery, 3:1404-1415 (Dec. 2013); published online Sep. 24, 2013.
Zhou; "Novel mutant-selective EGFR kinase inhibitors against EGFR T790M"; Nature, 462(24/31):1070-1074 (Dec. 2009).

*Primary Examiner* — Sudhakar Katakam
(74) *Attorney, Agent, or Firm* — Foley & Lardner LLP

(57) ABSTRACT

Heterocyclic pyrimidine compounds that modulate mutant-selective epidermal growth factor receptor (EGFR) and ALK kinase activity are disclosed. More specifically, the invention provides pyrimidines which inhibit, regulate and/or modulate kinase receptor, particularly in selectively modulation of various EGFR mutant activity and ALK kinase activity have been disclosed. Pharmaceutical compositions comprising the pyrimidine derivative, and methods of treatment for diseases associated with protein kinase enzymatic activity, particularly EGFR or ALK kinase activity including non-small cell lung cancer comprising administration of the pyrimidine derivative are disclosed.

9 Claims, No Drawings

PROTEIN TYROSINE KINASE MODULATORS AND METHODS OF USE

CROSS-REFERENCE TO RELATED APPLICATIONS

This application is a National Stage application of PCT/CN2014/082084, filed Jul. 11, 2014, which claims priority from International application PCT/CN2013/079232, filed Jul. 11, 2013.

TECHNICAL FIELD

This invention relates to heterocyclic pyrimidine compounds that modulate mutant-selective epidermal growth factor receptor (EGFR) kinase activity for modulating cellular activities such as proliferation, differentiation, programmed cell death, migration and chemoinvasion. More specifically, the invention provides pyrimidines which selectively inhibit, regulate and/or modulate kinase receptor, particularly in modulation of various EGFR mutant activity related to the changes in cellular activities as mentioned above, pharmaceutical compositions comprising the pyrimidine derivative, and methods of treatment for diseases associated with protein kinase enzymatic activity, particularly EGFR kinase activity including non-small cell lung cancer comprising administration of the pyrimidine derivative.

BACKGROUND ART

The epidermal growth factor receptor (EGFR, Erb-B1) belongs to a family of proteins, involved in the proliferation of normal and malignant cells (Artega, C. L., J. Clin Oncol 19, 2001, 32-40). Overexpression of Epidermal Growth Factor Receptor (EGFR) is present in at least 70% of human cancers (Seymour, L. K., Curr Drug Targets 2, 2001, 117-133) such as, non-small cell lung carcinomas (NSCLC), breast cancers, gliomas, squamous cell carcinoma of the head and neck, and prostate cancer (Raymond et al., Drugs 60 Suppl 1, 2000, discussion 41-2; Salomon et al., Crit Rev Oncol Hematol 19, 1995, 183-232; Voldborg et al., Ann Oncol 8, 1997, 1197-1206). The EGFR-TK is therefore widely recognized as an attractive target for the design and development of compounds that can specifically bind and inhibit the tyrosine kinase activity and its signal transduction pathway in cancer cells, and thus can serve as either diagnostic or therapeutic agents. For example, the EGFR tyrosine kinase (EGFR-TK) reversible inhibitor, TARCEVA®, is approved by the FDA for treatment of NSCLC and advanced pancreatic cancer. Other anti-EGFR targeted molecules have also been approved including LAPATINIB®, and IRESSA®.

The efficacy of erlotinib and gefitinib is limited when administered to all lung cancer patients. When erlotinib or gefitinib are used in the treatment of all lung cancer patients (not selected for presence/absence of activated (mutant) EGFR), the likelihood of tumor shrinkage (response rate) is 8-10% and the median time to tumor progression is approximately 2 months {Shepherd et al NEJM 2004, Thatcher et al. Lancet 2005}. In 2004 it was discovered that lung cancers with somatic mutations in EGFR were associated with dramatic clinical responses following treatment with geftinib and erlotinib {Paez et al. Science 2004; Lynch et al. NEJM 2004; Pao et al PNAS 2004}. Somatic mutations identified to date include point mutations in which a single aminoacid residue is altered in the expressed protein (e.g. L858R, G719S, G719C, G719A, L861Q), as well as small in frame deletions in Exon19 or insertions in Exon20. Somatic mutations in EGFR are found in 10-15% of Caucasian and in 30-40% of Asian NSCLC patients. EGFR mutations are present more frequently in never-smokers, females, those with adenocarcinoma and in patients of East Asian ethnicity {Shigematsu et al JNCI 2005}. These are the same groups of patients previously clinically identified as most likely to benefit from gefltinib or erlotinib {Fukuoka et al. JCO 2003; Kris et al JAMA 2003 and Shepherd et al NEJM 2004}. Six prospective clinical trials treating chemotherapy na[iota]ve patients with EGFR mutations with gefltinib or erlotinib have been reported to date {Inoue et al JCO 2006, Tamura et al Br. J Cancer 2008; Asahina et al., Br. J. Cancer 2006; Sequist et al., JCO 2008}. Cumulatively, these studies have prospectively identified and treated over 200 patients with EGFR mutations. Together they demonstrate radiographic response rates ranging from 60-82% and median times to progression of 9.4 to 13.3 months in the patients treated with gefltinib and erlotinib. These outcomes are 3 to 4 folder greater than that observed with platin-based chemotherapy (20-30% and 3-4 months, respectively) for advanced NSCLC {Schiller, et al JCO 2002}. In a recently completed phase III clinical trial, EGFR mutant chemotherapy na[iota]ve NSCLC patients had a significantly longer (hazard ratio=0.48 (95% CI; 0.36-0.64); p<0.0001) progression free survival (PFS) and tumor response rate (71.3 vs. 47.2%; p=0.0001) when treated with gefltinib compared with conventional chemotherapy {Mok et al. ESMO meeting 2008}. Conversely, NSCLC patients that were EGFR wild type had a worse outcome when they received gefltinib compared to chemotherapy as their initial treatment for advanced NSCLC {Mok et al ESMO meeting 2008}. Thus EGFR mutations provide an important selection method for NSCLC patients for a therapy (EGFR TKIs) that is more effective than conventional systemic chemotherapy. EGFR mutations are routinely being evaluated in NSCLC patients in many clinical centers.

Despite the initial clinical benefits of gefitinib/erlotinib in NSCLC patients harboring EGFR mutations, most if not all patients ultimately develop progressive cancer while receiving therapy on these agents. Initial studies of relapsed specimens identified a secondary EGFR mutation, T790M, that renders gefitinib and erlotinib ineffective inhibitors of EGFR kinase activity {Kobayashi et al NEJM 2005 and Pao et al PLOS Medicien 2005}. Subsequent studies have demonstrated that the EGFR T790M mutation is found in approximately 50% of tumors (24/48) from patients that have developed acquired resistance to gefitinib or erlotinib {Kosaka et al CCR 2006; Balak et al CCR 2006 and Engelman et al Science 2007}. This secondary genetic alteration occurs in the 'gatekeeper' residue and in an analogous position to other secondary resistance alleles in diseases treated with kinase inhibitors (for example T315I in ABL in imatinib resistant CML).

The initial identification of EGFR T790M also determined that an irreversible EGFR inhibitor, CL-387,785, could still inhibit EGFR even when it possessed the T790M mutation. Subsequent studies demonstrated that other irreversible EGFR inhibitors, EKB-569 and HKI-272, could also inhibit phosphorylation of EGFR T790M and the growth of EGFR mutant NSCLC cell lines harboring the T790M mutation {Kwak et al PNAS 2005; Kobayashi et al NEJM 2005}. These irreversible EGFR inhibitors are structurally similar to reversible inhibitors gefitinib and erlotinib, but differ in that they contain a Michael-acceptor that allows them to covalently bind EGFR at Cys 797. The T790M mutation does not preclude binding of irreversible inhibitors; instead, it confers resistance to reversible inhibitors in part by increasing the affinity of the enzyme for ATP, at least in the L858R/T790M mutant EGFR {Yun et al., PNAS 2008}. Irreversible inhibitors overcome this mechanism of resistance because once they are covalently bound, they are no longer in competition with ATP. These observations have led to clinical development of irreversible EGFR inhibitors for patients developing acquired resistance to gefitinib or erlotinib. Three such agents (HKI-272, BIBW2992 and PF00299804) are currently under clinical development. However, the preclinical studies to date would suggest that these agents are not optimal at inhibiting EGFR variants bearing the T790M mutation.

Recent studies in a mouse model of EGFR L858R/T790M mediated lung cancer demonstrate that a subset of cancers in these mice (bronchial tumors) were insensitive to HKI-272 alone {Li et al Cancer Cell 2007}. Thus even in this solely EGFR-driven model, HKI-272 alone is unable to cause tumor regression. This is in sharp contrast to the dramatic effects of erlotinib alone in mouse lung cancer models that contain only EGFR activating mutations {Ji et al Cancer Cell 2006} and suggests that HKI-272 may also be ineffective in some NSCLC patients with EGFR T790M. Similar findings have been reported for BIBW 2992 (Li et al. Oncogene 2008) Furthermore, the IC50 of HKI-272 required to inhibit the growth of Ba/F3 cells harboring EGFR T790M in conjunction with different exon 19 deletion mutations ranges from 200-800 nM while the mean Cmax in the Phase I trial was only about 200 nM {Yuza et al Cancer Biol Ther 2007; Wong et al CCR 2009 in press}. Thus there continues to be a need to develop more effective EGFR targeted agents capable of inhibiting EGFR T790M.

A major limitation of all current EGFR inhibitors is the development of toxicity in normal tissues. Since ATP affinity of EGFR T790M is similar to WT EGFR, the concentration of an irreversible EGFR inhibitor required to inhibit EGFR T790M will also effectively inhibit WT EGFR. The class-specific toxicities of current EGFR kinase inhibitors, skin rash and diarrhea, are a result of inhibiting WT EGFR in non-cancer tissues. This toxicity, as a result of inhibiting WT EGFR, precludes dose escalation of current agents to plasma levels that would effectively inhibit EGFR T790M. A major advance would be the identification of a mutant specific EGFR inhibitor that was less effective against wild type EGFR. Such an agent would likely be clinically more effective and also potentially more tolerable as a therapeutic agent in patients with cancer.

Anaplastic lymphoma kinase (ALK) belongs to the receptor tyrosine kinase (RTK) superfamily of protein kinases. ALK expression in normal adult human tissues is restricted to endothelial cells, pericytes, and rare neural cells. Oncogenic, constitutively active ALK fusion proteins are expressed in anaplastic large cell lymphoma (ALCL) and inflammatory myofibroblastic tumors (IMT). ALK has also recently been implicated as an oncogene in a small fraction of non-small-cell lung cancers and neuroblastomas (Choi et al, Cancer Res 2008; 68: (13); Webb et al, Expert Rev. Anticancer Ther. 9(3), 331-356, 2009).

Anaplastic large-cell lymphomas (ALCLs) are a subtype of the high-grade non-Hodgkin's family of lymphomas with distinct morphology, immunophenotype, and prognosis. ALCLs are postulated to arise from T cells and, in rare cases, can also exhibit a B cell phenotype. In addition, there are 40% of cases for which the cell of origin remains unknown and that are classified as "null". First described as a histological entity by Stein et al. based on the expression of CD30 (Ki-1), ALCL presents as a systemic disease afflicting skin, bone, soft tissues, and other organs, with or without the involvement of lymph nodes. ALCL can be subdivided into at least two subtypes, characterized by the presence or absence of chromosomal rearrangements between the anaplastic lymphoma kinase (ALK) gene locus and various fusion partners such as nucleophosmin (NPM). Approximately 50-60% of cases of ALCL are associated with the t(2;5)(p23; q35) chromosomal translocation, which generates a hybrid gene consisting of the intracellular domain of the ALK tyrosine kinase receptor juxtaposed with NPM. The resulting fusion protein, NPM-ALK has constitutive tyrosine kinase activity and has been shown to transform various hematopoietic cell types in vitro and support tumor formation in vivo.

NPM-ALK, an oncogenic fusion protein variant of the Anaplastic Lymphoma Kinase, which results from a chromosomal translocation is implicated in the pathogenesis of human anaplastic large cell lymphoma (Pulford K, Morris S W, Turturro F. Anaplastic lymphoma kinase proteins in growth control and cancer. J Cell Physiol 2004; 199: 330-58). The roles of aberrant expression of constitutively active ALK chimeric proteins in the pathogenesis of ALCL have been well defined (Weihua Wan, et. al. Anaplastic lymphoma kinase activity is essential for the proliferation and survival of anaplastic large cell lymphoma cells. Blood First Edition Paper, prepublished online Oct. 27, 2005; DOI 10.1182/blood-2005-08-3254). NPM-ALK is implicated in the dysregulation of cell proliferation and apoptosis in ALCL lymphoma cells (Pulford et al, 2004).

Other less frequent ALK fusion partners, e.g., tropomyosin-3 and clathrin heavy chain, have also been identified in ALCL as well as in CD30-negative diffuse large-cell lymphoma. Despite subtle differences in signaling and some biological functions, all fusions appear to be transforming to fibroblasts and hematopoietic cells. Extensive analysis of the leukemogenic potential of NPM-ALK in animal models has further corroborated the importance of NPM-ALK and other ALK rearrangements in the development of ALK-positive ALCL and other diseases.

ALK fusion proteins have also been detected in cell lines and/or primary specimens representing a variety of other tumors including inflammatory myofibroblastic tumor (IMT), neuroectodermal tumors, glioblastomas, melanoma, rhabdomyosarcoma tumors, and esophageal squamous cell carcinomas (see review by Webb T R, Slavish J, et al. Anaplastic lymphoma kinase: role in cancer pathogenesis and small-molecule inhibitor development for therapy. Expert Rev Anticancer Ther. 2009; 9(3): 331-356). Recently, ALK is also implicated in small percent of breast colorectal and non-small cell lung cancers (Lin E, Li L, et al. Exon Array Profiling Detects EML4-ALK Fusion in Breast, Colorectal, and Non-Small Cell Lung Cancers. Mol Cancer Res 2009; 7(9): 1466-76).

Approximately 3-7% of lung tumors harbor ALK fusions, and multiple different ALK rearrangements have been described in NSCLC. The majority of these ALK fusion variants are comprised of portions of the echinoderm microtubule-associated protein-like 4 (EML4) gene with the ALK gene. At least nine different EML4-ALK fusion variants have been identified in NSCLC (Takeuchi et al. Multiplex reverse transcription-PCR screening for EML4-ALK fusion transcripts. Clin Cancer Res. 2008, 15(9):3143-9). In addition, non-EML4 fusion partners have also been identified, including KIFSB-ALK (Takeuchi et al. KIFSB-ALK, a novel fusion oncokinase identified by an immunohistochemistry-based diagnostic system for ALK-positive lung cancer.

2009, 15(9):3143-9) and TFG-ALK (Rikova et al. Global survey of phosphotyrosine signaling identifies oncogenic kinases in lung cancer. Cell 2007, 131(6):1190-203).

The various N-terminal fusion partners promote dimerization and therefore constitutive kinase activity. Signaling downstream of ALK fusions results in activation of cellular pathways known to be involved in cell growth and cell proliferation (Mosse et al. Inhibition of ALK signaling for cancer therapy. Clin Cancer Res. 2009, 15(18):5609-14).

SUMMARY OF INVENTION

The present invention relates to heterocyclic pyrimidine compounds useful as EGFR or ALK inhibitors and for the treatment of conditions mediated by EGFR or ALK. The compounds of the invention have the general structure as Formula I or a pharmaceutically acceptable salt:

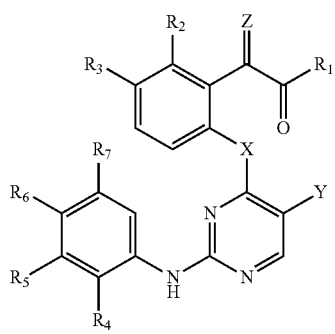

Formula I and

X is absent, O, S, or $NR_{16}$; $R_{16}$ is H or $C_{1-6}$ alkyl;

Y is halogen, OH, $NH_2$, CN, $N_3$, $NO_2$, or substituted or unsubstituted $C_{1-6}$ alkyl;

Z is O, S, $NR_{20}$, or $CR_{20}R_{21}$; and each $R_{20}$ or $R_{21}$ is independently H, halogen, substituted or unsubstituted $C_{1-6}$ alkyl, or substituted or unsubstituted $C_{1-6}$ alkoxy;

$R_1$ is hydroxy, $N(R_8)(R_9)$, $N(R_8)(CH_2)N(R_8)(R_9)$, $N(R_8)(R_9)CO(R_9)$, $N(R_8)CO(R_9)$, $C(O)R_8$, $C(O)OR_8$, $C(O)NH_2$, $C(O)NH(R_8)$, $C(O)N(R_8)(R_9)$, alkyl, haloalkyl, aryl, arylalkyl, alkoxy, heteroaryl, heterocyclic, or carbocyclic, each of which may be optionally substituted; each $R_8$ and $R_9$ is independently H, hydroxy, alkyl, alkenyl, vinyl, heterocyclic, cycloalkyl, or carbocyclic, each of which may be optionally substituted;

$R_2$ is H, F, or $C_{1-4}$ alkyl; or $R_2$ and $R_1$ together with the atoms to which they are attached form a 5- to 7-member heterocyclic ring comprising 1-3 hetero atoms independently selected from P, N, O or S, the heterocyclic ring being unsubstituted or substituted;

$R_3$ is H, halogen, or a 5 or 6 member heterocyclic ring comprising 1 or 2 N atoms, the heterocyclic ring being unsubstituted or substitute; or $R_2$ and $R_3$ together form 5- to 12-membered substituted or unsubstituted heterocyclic ring comprising 1, 2, 3 or 4 hetero atoms independently selected from N, or O;

$R_4$ is H, $C_{1-6}$alkoxy, $C_{3-6}$alkenyloxy, $C_{3-6}$cycloalkyloxy, halogen, —O-heterocyclic, heterocyclic, or —$NR_{24}(CH_2)_pNR_{24}R_{25}$, each of which may be optionally substituted; and P is 0, 1, 2, or 3, and each $R_{24}$ or $R_{25}$ is independently H, halogen, substituted or unsubstituted $C_{1-6}$ alkyl, or substituted or unsubstituted $C_{1-6}$ alkoxy;

$R_5$ is H, F, $C_{1-6}$alkyl, haloalkyl, $C_{1-6}$alkoxy, cycloalkyloxy, —$NR_{15}C(O)(CH_2)_nCR_{17}$=$CR_{18}R_{19}$, —$NR_{15}C(O)(CH_2)_nOCHR_{17}R_{18}$, —$NR_{15}C(O)(CH_2)_nCR_{17}(CH_2)_mCHR_{18}R_{19}$, —$NR_{15}C(O)(CH_2)_nCR_{17}$=$CH(CH_2)_mNR_{18}R_{19}$, —$NR_{15}C(O)CR_{17}(CH_2)_mNR_{18}(CH_2)_nNR_{18}R_{19}$, —$NR_{15}C(O)(CH_2)_nCHR_{17}R_{18}$, —$NR_{15}C(O)(CH_2)_nCR_{17}(CH_2)_mCHR_{18}R_{19}$, or

each of which may be optionally substituted; or is a 5 or 6 member heterocyclic ring containing 1, 2 or 3 hetero atoms independently selected from N or O, the heterocyclic ring being unsubstituted or substituted; and each $R_{15}$, $R_{17}$, $R_{18}$ or $R_{19}$ is independently absent, —H, —OH, —$NH_2$, halogen, alkyl, alkenyl, alkynyl, alkoxy, cycloalkyl, cycloalkenyl, cycloalkynyl, aryl, heteroalkyl, heterocyclic, a bond, or heteroaryl, each of which may be optionally substituted; and each m or n is independently 0, 1, 2, or 3;

$R_7$ is H, halogen, $C_{1-6}$alkyl, $C_{1-6}$alkoxy, $C_{3-6}$alkenyloxy, $C_{3-6}$cycloalkyloxy, —$OC(O)N(R_{10})(R_{11})$, —$NR_{10}C(O)OR_{11}$, —$NR_{22}C(O)CR_{23}$=$CR_{10}R_{11}$, —$NR_{22}C(O)CR_{23}(CH_2)_sCHR_{10}R_{11}$,

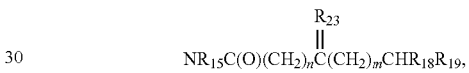

—$NR_{22}C(O)CR_{23}$=$CR_{10}(CH_2)_sR_{11}$, —$NR_{22}C(O)CR_{23}(CH_2)_sNR_{10}(CH_2)_tNR_{10}R_{11}$, or —$NR_{22}C(O)(CH_2)_sCR_{23}$=$CH(CH_2)_tNR_{10}R_{11}$, each of which may be optionally substituted; or is a 5 or 6 member heterocyclic ring comprising 1, 2 or 3 hetero atoms independently selected from N or O, the heterocyclic ring being unsubstituted or substituted; and each $R_{10}$, $R_{11}$, $R_{22}$ or $R_{23}$ is independently H, alkyl, alkenyl, alkynyl, and heteroalkyl, heterocyclic, cycloalkyl, cycloalkyloxy, heteroalkyl or a bond, each of which may be optionally substituted; or $R_{10}$ and $R_{11}$, together with the atoms to which they are attached, combine to form a 3-, 4-, 5- or 6-membered heterocyclic ring which is unsubstituted or substituted; and each s or t is independently 0, 1, 2, or 3;

$R_6$ combines with $R_7$ to form a 6 member heterocyclic ring, or is H, halogen, —CN, —$NO_2$, cycloalkyl, heteroalkyl, heterocyclic, heterocyclic-CO-alkyl, heterocyclic-CO-alkenyl, heteroaryl, —$R_{12}$, —$OR_{13}$, —O—$NR_{12}R_{13}$, —$NR_{12}R_{13}$, —$NR_{12}$—$NR_{12}R_{13}$, —$NR_{12}$—$OR_{13}$, —$C(O)GR_{13}$, —$OC(O)GR_{13}$, —$NR_{12}C(O)GR_{13}$, —$SC(O)GR_{13}$, —$NR_{12}C(=S)GR_{13}$, —$OC(=S)GR_{13}$, —$C(=S)GR_{13}$, —$YC(=NR_{12})GR_{13}$, -$GC(=N$—$OR_{12})GR_{13}$, -$GC(=N$—$NR_{12}R_{13})GR_{13}$, -$GP(=O)(GR_{12})(GR_{13})$, —$NR_{12}SO_2R_{13}$, —$S(O)_rR_{13}$, —$SO_2NR_{12}R_{13}$, —$NR^1SO_2NR_{12}R_{13}$, —$O(CH_2)_rR_{13}$, —$O(CH_2)_rNR_{12}R_{13}$, —$NR_{12}(CH_2)_rNR_{12}R_{13}$, —$NR_{12}(CH_2)_rR_{13}$, —$(CH_2)_rNR_{12}R_{13}$, or —$CH_2O(CH_2)_rNR_{12}R_{13}$, each of which may be optionally substituted; or

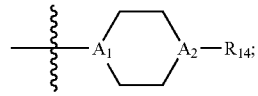

each G is, independently, a bond, —O—, —S—, or —NR$_{15}$; and each R$_{12}$, R$_{13}$, or R$_{15}$ is independently H, alkyl, alkenyl, alkynyl, cycloalkyl, cycloalkenyl, cycloalkynyl, aryl, heteroalkyl, heterocyclic or heteroaryl, each of which may be optionally substituted;

r is 0, 1, 2, or 3;

each A$_1$ or A$_2$ is, independently, CH or N; and R$_{14}$ is alkyl, alkoxy, alkenyl, alkynyl, cycloalkyl, cycloalkenyl, cycloalkynyl, aryl, heteroalkyl, heterocyclic or heteroary, each of which may be optionally substituted.

The present invention further provides some preferred technical solutions with regard to compound of Formula (I).

In some embodiments of Formula (I), Y is halogen, or substituted or unsubstituted C$_{1-6}$ alkyl.

In some embodiments of Formula (I), Y is halogen, methyl, or methyl substituted with halogen.

In some embodiments of Formula (I), Y is Cl, or CF$_3$.

In some embodiments of Formula (I), Y is CH$_3$.

In some embodiments of Formula (I), X is NR$_{16}$.

In some embodiments of Formula (I), R$_{16}$ is H.

In some embodiments of Formula (I), Z is O, or CH$_2$.

In some embodiments of Formula (I), Z is O.

In some embodiments of Formula (I), r is 0, 1, or 2.

In some embodiments of Formula (I), r is 3.

In some embodiments of Formula (I), each R$_6$ is independently H, halo, —R$_{12}$, —OR$_{13}$, or —NR$_{12}$R$_{13}$, each of which may be optionally substituted.

In some embodiments of Formula (I), each R$_6$ combines with R$_7$ to form a 6 member heterocyclic ring optionally substituted with H, hydroxy, alkyl, alkenyl, heterocyclic, cycloalkyl, —OR$_{13}$, —C(O)R$_{12}$, —NR$_{12}$R$_{13}$, or carbocyclic; or R$_6$ is —O(CH$_2$)$_r$R$_{13}$, —O(CH$_2$)$_r$NR$_{12}$R$_{13}$, —NR$_{12}$(CH$_2$)$_r$NR$_{12}$R$_{13}$, —NR$_{12}$(CH$_2$)$_r$R$_{13}$, —(CH$_2$)$_r$NR$_{12}$R$_{13}$, or —CH$_2$O(CH$_2$)$_r$NR$_{12}$R$_{13}$, each of which may be optionally substituted with substituted or unsubstituted C$_{1-6}$alkyl, substituted or unsubstituted C$_{2-6}$alkenyl, substituted or unsubstituted C$_{2-6}$alknyl, haloalkyl, halogen, substituted or unsubstituted alkoxy, —NH$_2$, —NCH$_3$CH$_3$, or —NHCH$_3$.

In some embodiments of Formula (I), each R$_{12}$, R$_{13}$, or R$_{15}$ is independently H, (C$_{1-6}$)alkyl, (C$_{2-6}$)alkenyl, (C$_{3-6}$)cycloalkyl, or (C$_{3-6}$)heterocyclic, each of which may be optionally substituted.

In some embodiments of Formula (I), each R$_6$ is independently —OH, —OEt, —NH$_2$, —NHCH$_3$, —NCH$_3$CH$_3$,

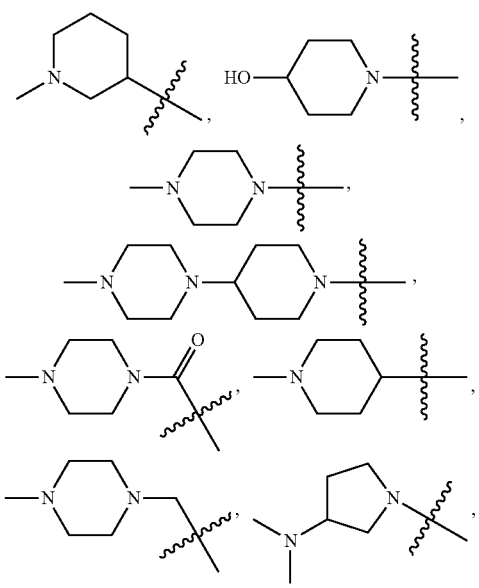

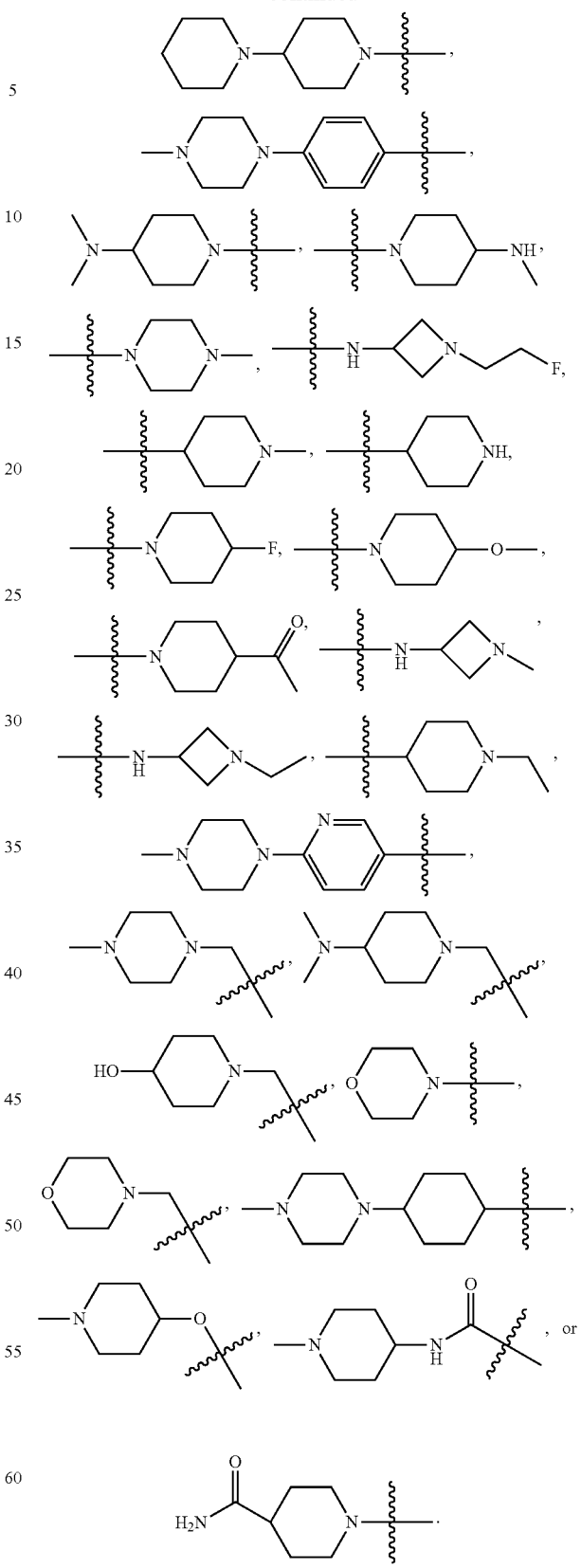

In some embodiments of Formula (I), each R$_6$ is independently —H, —F,

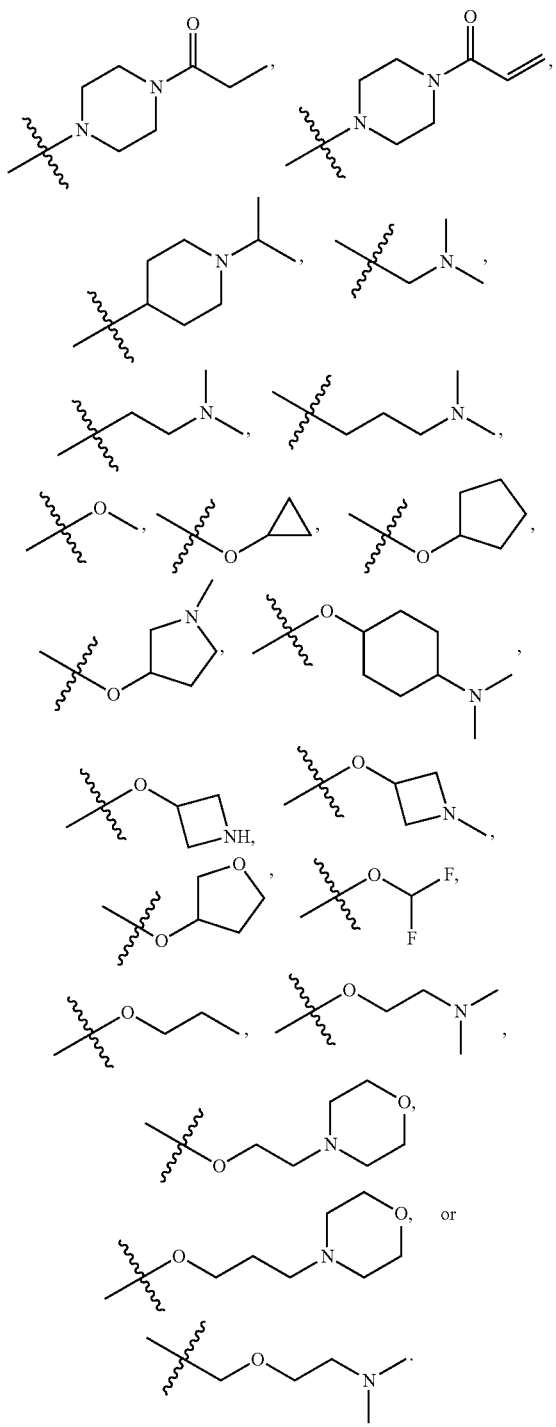

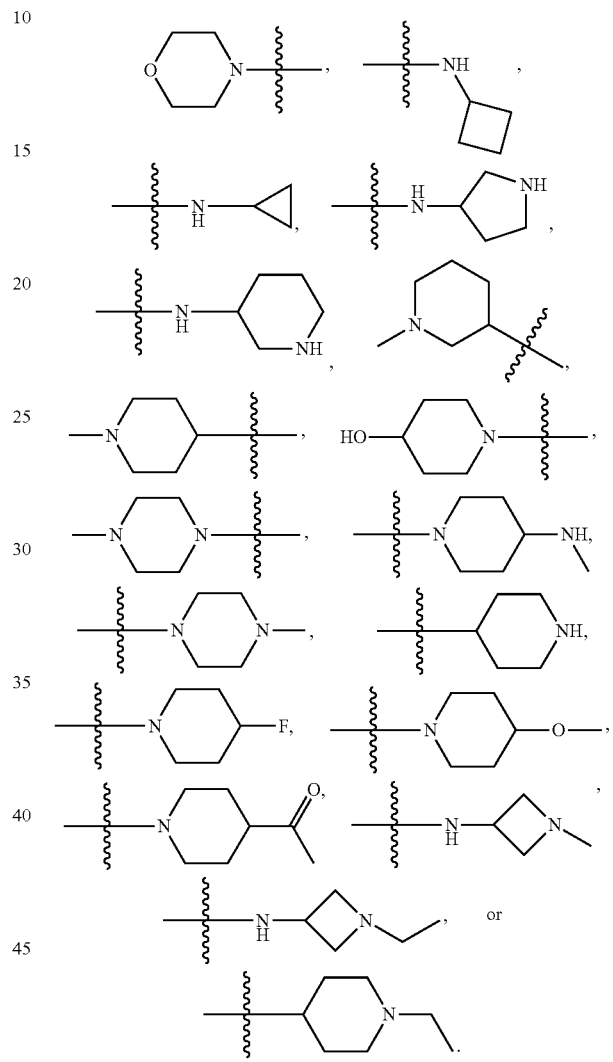

In some embodiments of Formula (I), each $R_8$ and $R_9$ is independently heterocyclic, cycloalkyl, or carbocyclic, each of which may be optionally substituted.

In some embodiments of Formula (I), each $R_1$ is independently —OH, —OEt, —NHOH, —NH$_2$, —NHCH$_3$, —NCH$_3$CH$_3$, —NHCH$_2$CH$_2$NCH$_3$CH$_3$, —NHCH$_2$CH$_2$OH, In some embodiments of Formula (I), each $R_2$ and $R_3$ is independently hydrogen, or halogen.

In some embodiments of Formula (I), $R_2$ and $R_3$ are both hydrogen.

In some embodiments of Formula (I), $R_1$ is hydroxy, $N(R_8)(R_9)$, alkyl, alkoxy, or haloalkyl, each of which may be optionally substituted.

In some embodiments of Formula (I), each $R_8$ and $R_9$ is independently H, hydroxy, $C_{1-6}$alkyl, $C_{2-6}$alkenyl.

In some embodiments of Formula (I), each $R_8$ or $R_9$ is independently methyl, or vinyl.

In some embodiments of Formula (I), each $R_1$ is independently —CH$_2$CH$_3$,

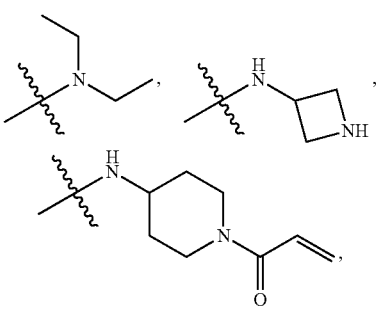

-continued

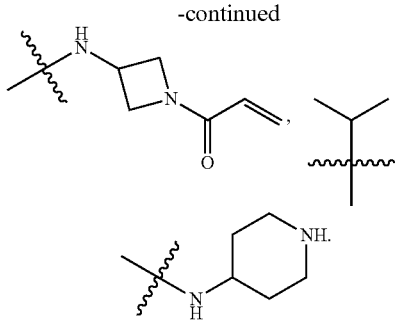

In some embodiments of Formula (I), $R_2$, $R_3$, and $R_5$ are all H.

In some embodiments of Formula (I), $R_4$ is $C_{1-6}$alkoxy, $C_{3-6}$ alkenyloxy, or $C_{3-6}$ cycloalkyloxy.

In some embodiments of Formula (I), $R_4$ is hydrogen, —OCH$_3$, —OEt,

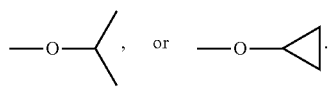

In some embodiments of Formula (I), $R_4$ is halogen, —O-heterocyclic, heterocyclic, or —NR$_{24}$(CH$_2$)$_P$NR$_{24}$R$_{25}$, each of which may be optionally substituted; and P is 1, or 2, each $R_{24}$ or $R_{25}$ is independently $C_{1-6}$ alkyl, $C_{1-6}$alkoxy, —NHOH, —NH$_2$, NHCH$_3$, NCH$_3$CH$_3$, or halogen.

In some embodiments of Formula (I), $R_4$ is hydrogen, F, —OCH$_3$,

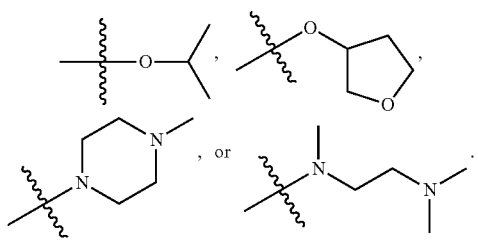

In some embodiments of Formula (I), $R_5$ is H, haloalkyl, $C_{1-6}$alkoxy, —NR$_{15}$C(O)(CH$_2$)$_n$CR$_{17}$=CR$_{18}$R$_{19}$, —NR$_{15}$C(O)(CH$_2$)$_n$OCHR$_{17}$R$_{18}$,

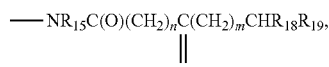

—NR$_{15}$C(O)(CH$_2$)$_n$CR$_{17}$=CH(CH$_2$)$_m$NR$_{18}$R$_{19}$, —NR$_{15}$C(O)CR$_{17}$(CH$_2$)$_m$NR$_{18}$(CH$_2$)$_n$NR$_{18}$R$_{19}$, or —NR$_{15}$C(O)(CH$_2$)—CHR$_{17}$R$_{18}$, each of which may be optionally substituted with $C_{1-6}$alkoxy, —NH$_2$, —NHCH$_3$, —NCH$_3$CH$_3$, —NHOH, $C_{1-6}$alkyl, halogen, or a bond; and each $R_{15}$, $R_{17}$, $R_{18}$ or $R_{19}$ is independently absent, —H, $C_{1-6}$alkyl, alkenyl, $C_{1-6}$alkoxy, —NHOH, —NH$_2$, —NHCH$_3$, —NCH$_3$CH$_3$, a bond, or $C_{3-6}$heterocyclic; and each m or n is independently 0, 1, or 2.

In some embodiments of Formula (I), $R_5$ is H, methyl, methyl substituted by halogen, methoxy,

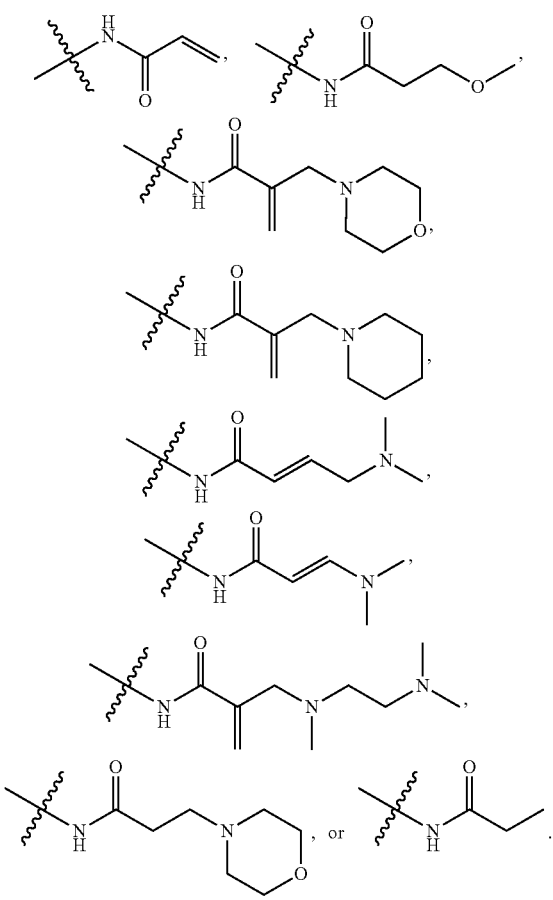

In some embodiments of Formula (I), $R_7$ is H, $C_{1-6}$alkyl, —NR$_{22}$C(O)CR$_{23}$=CR$_{10}$R$_{11}$, —NR$_{22}$C(O)CR$_{23}$(CH$_2$)$_s$CHR$_{10}$R$_{11}$, —NR$_{22}$C(O)CR$_{23}$=CR$_{10}$(CH$_2$)$_s$R$_{11}$, —NR$_{22}$C(O)CR$_{23}$(CH$_2$)$_s$NR$_{10}$(CH$_2$)$_t$NR$_{10}$R$_{11}$, or —NR$_{22}$C(O)(CH$_2$)$_s$CR$_{23}$=CH(CH$_2$)$_t$NR$_{10}$R$_{11}$, each of which may be optionally substituted; and each $R_{10}$, $R_{11}$, $R_{22}$ or $R_{23}$ is independently H, alkyl, alkenyl, heterocyclic, cycloalkyl, cycloalkyloxy, heteroalkyl or a bond, each of which may be optionally substituted with $C_{1-6}$alkyl, alkoxy, heterocyclic, cycloalkyl, cycloalkyloxy, heteroalkyl or a bond; and each s or t is independently 0, 1, or 2.

In some embodiments of Formula (I), wherein, $R_7$ is H, $C_{1-6}$alkyl,

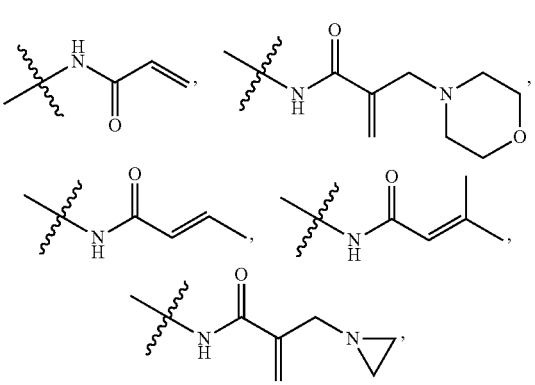

-continued

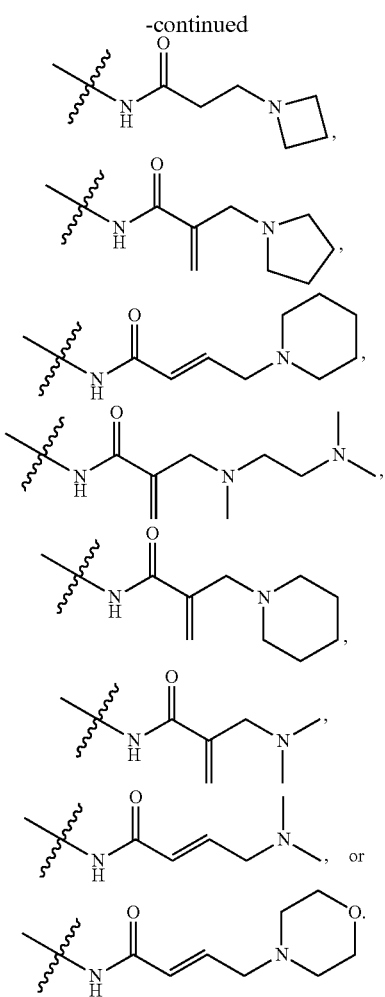

In some embodiments of Formula (I), the compound is of Formula II:

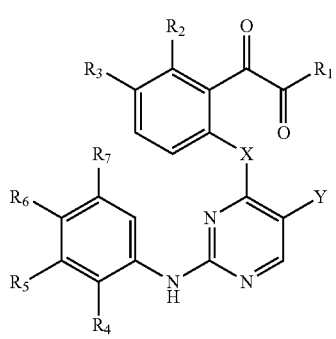

Formula II

The present invention further provides some preferred technical solutions with regard to compound of Formula (II).

In some embodiments of Formula (II), X is NH.

In some embodiments of Formula (II), Y is halogen, or haloalkyl.

In some embodiments of Formula (II), Y is Cl, or $CF_3$.

In some embodiments of Formula (II), Y is $C_{1-6}$alkyl.

In some embodiments of Formula (II), Y is $CH_3$.

In some embodiments of Formula (II), $R_1$ is —OH, —OEt, —NHOH, —$NH_2$, —$NHCH_3$, —$NCH_3CH_3$, —$NHCH_2CH_2NCH_3CH_3$, —$NHCH_2CH_2OH$,

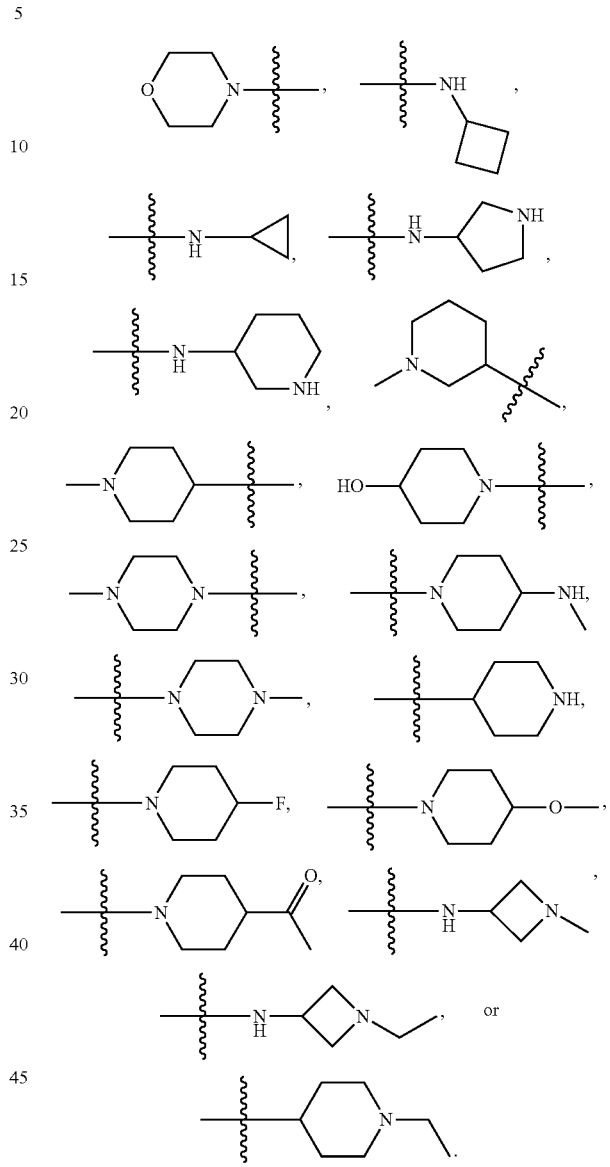

In some embodiments of Formula (II), each $R_1$ is independently —$CH_2CH_3$,

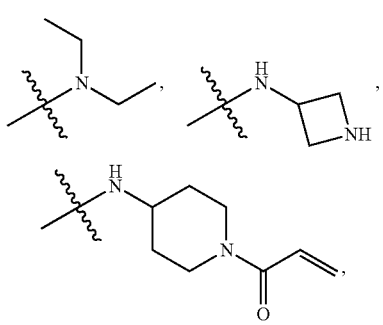

-continued
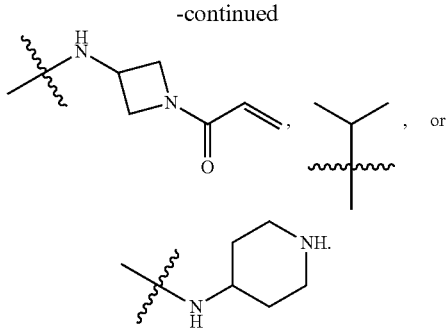
In some embodiments of Formula (II), R₂, R₃, R₅, and R₇ are all H.
In some embodiments of Formula (II), R₂, R₃, and R₅ are all H.
In some embodiments of Formula (II), R₅ is H, methyl substituted by halogen, methoxy,
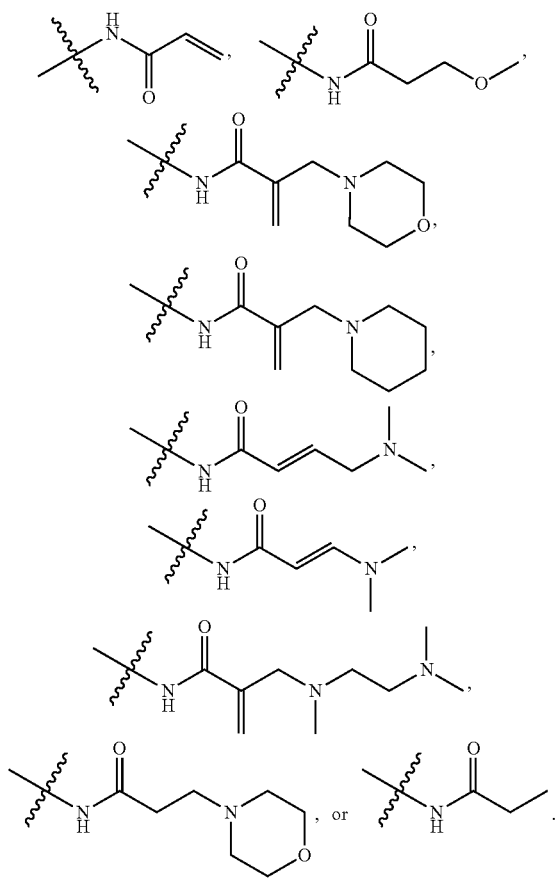
In some embodiments of Formula (II), R₄ is hydrogen, F, —OCH₃,
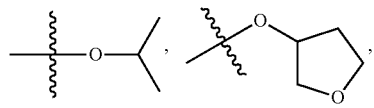
-continued
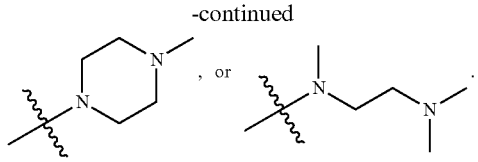
In some embodiments of Formula (II), each R₆ is independently —OH, —OEt, —NHOH, —NH₂, —NHCH₃, or —NCH₃CH₃,
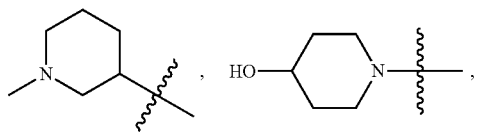
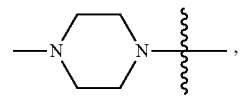
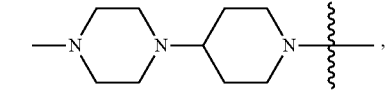
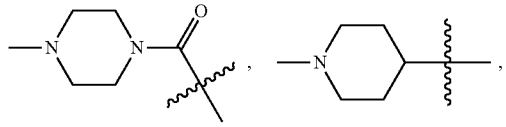
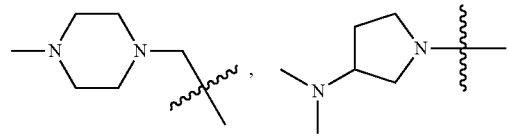
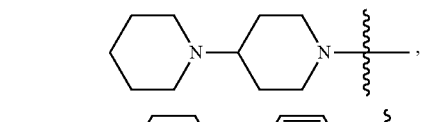
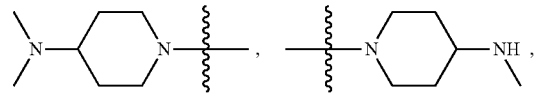
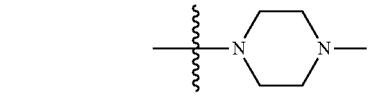
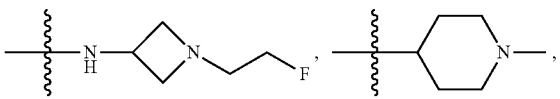
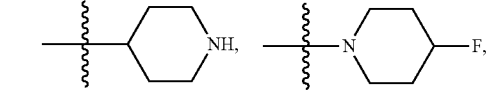
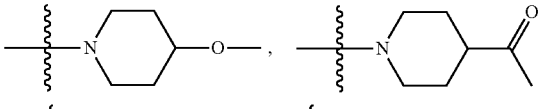
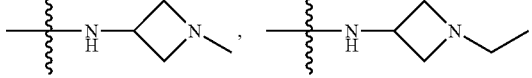

17
-continued

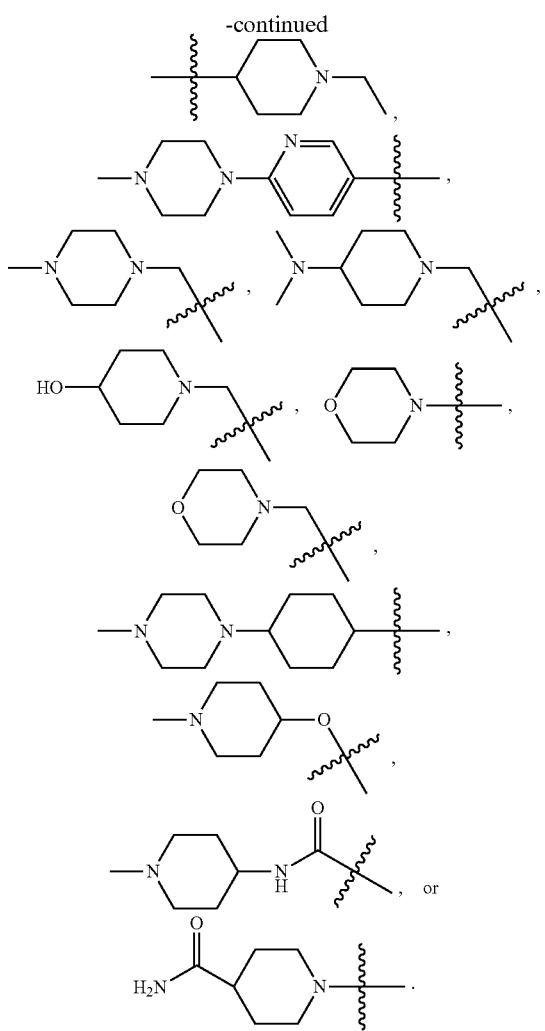

In some embodiments of Formula (II), each $R_6$ is independently —H, —F,

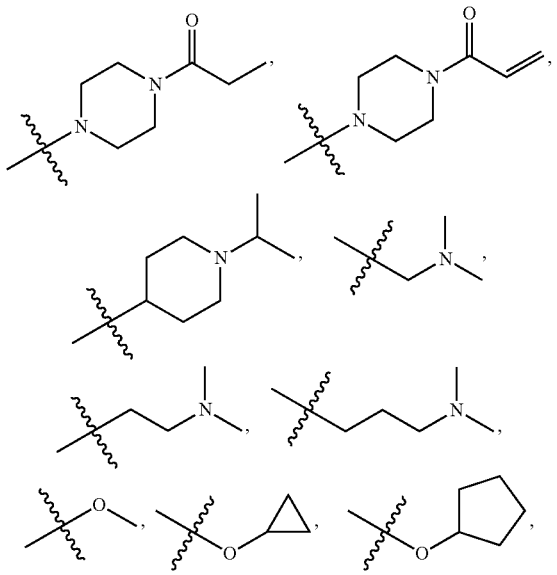

18
-continued

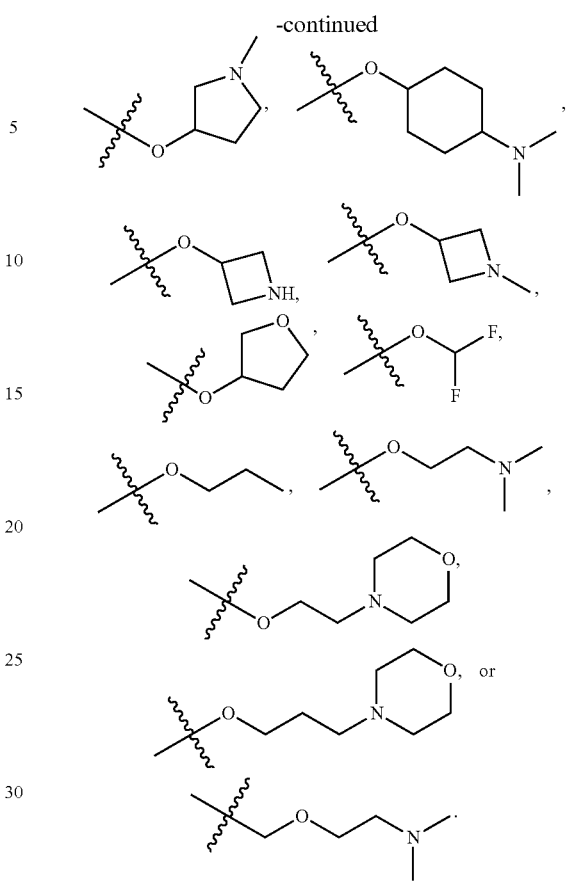

The present invention further provides some preferred technical solutions with regard to compound of Formula (I) or Formula (II), compound is 1) ethyl 2-(2-(5-chloro-2-(4-(4-(dimethylamino)piperidin-1-yl)-2-methoxyphenylamino)pyrimidin-4-ylamino)phenyl)-2-oxoacetate;
2) 2-(2-(5-chloro-2-(4-(4-(dimethylamino)piperidin-1-yl)-2-methoxyphenylamino)pyrimidin-4-ylamino)phenyl)-2-oxoacetic acid;
3) 2-(2-(5-chloro-2-(4-(4-(dimethylamino)piperidin-1-yl)-2-methoxyphenylamino)pyrimidin-4-ylamino)phenyl)-N-hydroxy-2-oxoacetamide;
4) 2-(2-(5-chloro-2-(4-(4-(dimethylamino)piperidin-1-yl)-2-methoxyphenylamino)pyrimidin-4-ylamino)phenyl)-2-oxoacetamide;
5) ethyl 2-(2-(5-chloro-2-(4-(4-(dimethylamino)piperidin-1-yl)-2-methoxyphenylamino)pyrimidin-4-ylamino)phenyl)acrylate;
6) 2-(2-((5-chloro-2-((2-methoxy-4-(4-methylpiperazin-1-yl)phenyl)amino)pyrimidin-4-yl)amino)phenyl)-2-oxoacetamide;
7) 2-(2-((2-((4-(4-acetylpiperazin-1-yl)-2-methoxyphenyl)amino)-5-chloropyrimidin-4-yl)amino)phenyl)-2-oxoacetamide;
8) 2-(2-((5-chloro-2-((2-isopropoxy-5-methyl-4-(piperidin-4-yl)phenyl)amino)pyrimidin-4-yl)amino)phenyl)-2-oxoacetamide;
9) 2-(2-((5-chloro-2-((4-((1-(2-fluoroethyl)azetidin-3-yl)amino)-2-methoxyphenyl)amino)pyrimidin-4-yl)amino)phenyl)-2-oxoacetamide;
10) 2-(2-((2-((2-methoxy-4-(4-methylpiperazin-1-yl)phenyl)amino)-5-(trifluoromethyl)pyrimidin-4-yl)amino)phenyl)-2-oxoacetamide;

11) 2-(2-((2-((4-(4-acetylpiperazin-1-yl)-2-methoxyphenyl)amino)-5-(trifluoromethyl)pyrimidin-4-yl)amino)phenyl)-2-oxoacetamide;
12) 2-(2-((2-((2-isopropoxy-5-methyl-4-(piperidin-4-yl)phenyl)amino)-5-(trifluoromethyl)pyrimidin-4-yl)amino)phenyl)-2-oxoacetamide;
13) 2-(2-((2-((4-((1-(2-fluoroethyl)azetidin-3-yl)amino)-2-methoxyphenyl)amino)-5-(trifluoromethyl)pyrimidin-4-yl)amino)phenyl)-2-oxoacetamide;
14) 2-(2-((2-((4-(4-(dimethylamino)piperidin-1-yl)-2-methoxyphenyl)amino)-5-(trifluoromethyl)pyrimidin-4-yl)amino)phenyl)-2-oxoacetamide;
15) 2-(2-((2-((4-(4-(dimethylamino)piperidin-1-yl)-2-methoxyphenyl)amino)-5-(trifluoro methyl)pyrimidin-4-yl)amino)phenyl)-2-oxoacetic acid;
16) 2-(2-((5-chloro-2-((4-(4-(dimethylamino)piperidin-1-yl)-2-methoxyphenyl)amino)pyrimidin-4-yl)amino)phenyl)-N-methyl-2-oxoacetamide;
17) 2-(2-((5-chloro-2-((4-(4-(dimethylamino)piperidin-1-yl)-2-methoxyphenyl)amino)pyrimidin-4-yl)amino)phenyl)-N,N-dimethyl-2-oxoacetamide;
18) 1-(2-((5-chloro-2-((4-(4-(dimethylamino)piperidin-1-yl)-2-methoxyphenyl)amino)pyrimidin-4-yl)amino)phenyl)-2-morpholinoethane-1,2-dione;
19) 2-(2-((5-chloro-2-((4-(4-(dimethylamino)piperidin-1-yl)-2-methoxyphenyl)amino)pyrimidin-4-yl)amino)phenyl)-N-(2-(dimethylamino)ethyl)-2-oxoacetamide;
20) 2-(2-((5-chloro-2-((2-methoxy-4-(4-(methylamino)piperidin-1-yl)phenyl)amino)pyrimidin-4-yl)amino)phenyl)-N-(2-hydroxyethyl)-2-oxoacetamide;
21) 1-(2-((5-chloro-2-((4-(4-(dimethylamino)piperidin-1-yl)-2-methoxyphenyl)amino)pyrimidin-4-yl)amino)phenyl)-3-methylbutane-1,2-dione;
22) 1-(2-((5-chloro-2-((4-(4-(dimethylamino)piperidin-1-yl)-2-methoxyphenyl)amino)pyrimidin-4-yl)amino)phenyl)propane-1,2-dione;
23) 1-(2-((5-chloro-2-((4-(4-(dimethylamino)piperidin-1-yl)-2-methoxyphenyl)amino)pyrimidin-4-yl)amino)phenyl)-3-(dimethylamino)propane-1,2-dione;
24) N-(azetidin-3-yl)-2-(2-((5-chloro-2-((4-(4-(dimethylamino)piperidin-1-yl)-2-methoxyphenyl)amino)pyrimidin-4-yl)amino)phenyl)-2-oxoacetamide;
25) 2-(2-((5-chloro-2-((4-(4-(dimethylamino)piperidin-1-yl)-2-methoxyphenyl)amino)pyrimidin-4-yl)amino)phenyl)-N-cyclopropyl-2-oxoacetamide;
26) 2-(2-((5-chloro-2-((4-(4-(dimethylamino)piperidin-1-yl)-2-methoxyphenyl)amino)pyrimidin-4-yl)amino)phenyl)-2-oxo-N-(pyrrolidin-3-yl)acetamide;
27) 2-(2-((5-chloro-2-((4-(4-(dimethylamino)piperidin-1-yl)-2-methoxyphenyl)amino)pyrimidin-4-yl)amino)phenyl)-2-oxo-N-(piperidin-4-yl)acetamide;
28) 2-(2-((5-chloro-2-((4-(4-(dimethylamino)piperidin-1-yl)-2-methoxyphenyl)amino)pyrimidin-4-yl)amino)phenyl)acrylamide;
29) 2-(2-((5-chloro-2-((4-(4-(dimethylamino)piperidin-1-yl)-2-methoxyphenyl)amino)pyrimidin-4-yl)amino)phenyl)acrylic acid;
30) 2-(2-((5-chloro-2-((2-methoxy-4-(4-methylpiperazin-1-yl)phenyl)amino)pyrimidin-4-yl)amino)phenyl)acrylamide;
31) 2-(2-((5-chloro-2-((2-methoxy-4-(4-methylpiperazin-1-yl)phenyl)amino)pyrimidin-4-yl)amino)phenyl)acrylic acid;
32) 2-(2-((5-chloro-2-((4-((1-(2-fluoroethyl)azetidin-3-yl)amino)-2-methoxyphenyl)amino)pyrimidin-4-yl)amino)phenyl)acrylamide;
33) 2-(2-((5-chloro-2-((4-((1-(2-fluoroethyl)azetidin-3-yl)amino)-2-methoxyphenyl)amino)pyrimidin-4-yl)amino)phenyl)acrylic acid;
34) 2-(2-((5-chloro-2-((2-methoxy-4-(1-methylpiperidin-4-yl)phenyl)amino)pyrimidin-4-yl)amino)phenyl)acrylamide;
35) 2-(2-((5-chloro-2-((2-methoxy-4-(1-methylpiperidin-4-yl)phenyl)amino)pyrimidin-4-yl)amino)phenyl)acrylic acid;
36) 2-(2-((5-chloro-2-((2-methoxy-4-(piperidin-4-yl)phenyl)amino)pyrimidin-4-yl)amino)phenyl)acrylamide;
37) 2-(2-((5-chloro-2-((2-methoxy-4-(piperidin-4-yl)phenyl)amino)pyrimidin-4-yl)amino)phenyl)acrylic acid;
38) 2-(2-((5-chloro-2-((4-(4-fluoropiperidin-1-yl)-2-methoxyphenyl)amino)pyrimidin-4-yl)amino)phenyl)acrylamide;
39) 2-(2-((5-chloro-2-((2-methoxy-4-(4-methoxypiperidin-1-yl)phenyl)amino)pyrimidin-4-yl)amino)phenyl)acrylamide;
40) N-(3-(5-chloro-4-(2-(2-(dimethylamino)-2-oxoacetyl)phenylamino)pyrimidin-2-ylamino)phenyl)acrylamide;
41) N-(3-(5-chloro-4-(2-(2-(dimethylamino)-2-oxoacetyl)phenylamino)pyrimidin-2-ylamino)-4-methoxyphenyl)-2-(morpholinomethyl)acrylamide;
42) 1-(2-(2-(4-(4-acetylpiperazin-1-yl)-2-methoxyphenylamino)-5-chloropyrimidin-4-ylamino)phenyl)-2-morpholinoethane-1,2-dione;
43) 1-(2-(2-(2-methoxy-4-(4-methylpiperazin-1-yl)phenylamino)-5-(trifluoromethyl)pyrimidin-4-ylamino)phenyl)-2-morpholinoethane-1,2-dione;
44) 1-(2-(5-chloro-2-(2-methoxy-4-(4-methylpiperazin-1-yl)phenylamino)pyrimidin-4-ylamino)phenyl)-2-morpholinoethane-1,2-dione;
45) 1-(2-(2-(4-(4-(dimethylamino)piperidin-1-yl)-2-methoxyphenylamino)-5-(trifluoromethyl)pyrimidin-4-ylamino)phenyl)-2-morpholinoethane-1,2-dione;
46) 2-(2-(5-chloro-2-(2-methoxy-4-(4-methylpiperazin-1-yl)phenylamino)pyrimidin-4-ylamino)phenyl)-N,N-dimethyl-2-oxoacetamide;
47) 2-(2-(5-chloro-2-(2-methoxy-4-(4-methylpiperazin-1-yl)phenylamino)pyrimidin-4-ylamino)phenyl)-N-methyl-2-oxoacetamide;
48) 2-(2-(5-chloro-2-(2-methoxy-4-morpholinophenylamino)pyrimidin-4-ylamino)phenyl)-N,N-dimethyl-2-oxoacetamide;
49) 2-(2-(5-chloro-2-(2-methoxy-4-(4-methylpiperazin-1-yl)phenylamino)pyrimidin-4-ylamino)phenyl)-N-cyclopropyl-2-oxoacetamide;
50) 2-(2-(2-(4-(4-acetylpiperazin-1-yl)-2-methoxyphenylamino)-5-chloropyrimidin-4-ylamino)phenyl)-N-cyclopropyl-2-oxoacetamide;
51) 2-(2-(5-chloro-2-(2-methoxy-4-morpholinophenylamino)pyrimidin-4-ylamino)phenyl)-N-cyclopropyl-2-oxoacetamide;
52) 2-(2-(5-chloro-2-(2-methoxy-4-(4-propionylpiperazin-1-yl)phenylamino)pyrimidin-4-ylamino)phenyl)-N,N-dimethyl-2-oxoacetamide;
53) 2-(2-(2-(4-(4-acetylpiperazin-1-yl)-2-methoxyphenylamino)-5-chloropyrimidin-4-ylamino)phenyl)-N,N-dimethyl-2-oxoacetamide;
54) 2-(2-(5-chloro-2-(2-methoxy-4-(4-propionylpiperazin-1-yl)phenylamino)pyrimidin-4-ylamino)phenyl)-N-methyl-2-oxoacetamide;
55) N-(1-acryloylazetidin-3-yl)-2-(2-(5-chloro-2-(2-methoxy-4-(4-methylpiperazin-1-yl)phenylamino)pyrimidin-4-ylamino)phenyl)-2-oxoacetamide;

56) N-(1-acryloylpiperidin-4-yl)-2-(2-(5-chloro-2-(2-methoxy-4-(4-methylpiperazin-1-yl)phenyl amino)pyrimidin-4-ylamino)phenyl)-2-oxoacetamide;
57) N-(3-(5-chloro-4-(2-(2-(methylamino)-2-oxoacetyl)phenylamino)pyrimidin-2-ylamino)phenyl)acrylamide;
58) N-(3-(4-(2-(2-amino-2-oxoacetyl)phenylamino)-5-(trifluoromethyl)pyrimidin-2-ylamino)phenyl)acrylamide;
59) N-(1-acryloylpiperidin-4-yl)-2-(2-(5-chloro-2-(4-fluoro-3-methoxyphenylamino)pyrimidin-4-ylamino)phenyl)-2-oxoacetamide;
60) 2-(2-(5-chloro-2-(3-methoxy-4-(4-methylpiperazin-1-yl)phenylamino)pyrimidin-4-ylamino)phenyl)-N-methyl-2-oxoacetamide;
61) 2-(2-(5-chloro-2-(3-methoxy-4-(4-methylpiperazin-1-yl)phenylamino)pyrimidin-4-ylamino)phenyl)-N,N-dimethyl-2-oxoacetamide;
62) 2-(2-(5-chloro-2-(4-fluoro-3-methoxyphenylamino)pyrimidin-4-ylamino)phenyl)-N,N-dimethyl-2-oxoacetamide;
63) 2-(2-(5-chloro-2-(4-fluoro-3-methoxyphenylamino)pyrimidin-4-ylamino)phenyl)-N-methyl-2-oxoacetamide;
64) N-(5-(5-chloro-4-(2-(2-(methylamino)-2-oxoacetyl)phenylamino)pyrimidin-2-ylamino)-2-methoxyphenyl)acrylamide;
65) N-(5-(5-chloro-4-(2-(2-(dimethylamino)-2-oxoacetyl)phenylamino)pyrimidin-2-ylamino)-2-methoxyphenyl)acrylamide;
66) N-(5-(5-chloro-4-(2-(2-(dimethylamino)-2-oxoacetyl)phenylamino)pyrimidin-2-ylamino)-2-fluoro-4-methoxyphenyl)acrylamide;
67) N-(3-(5-chloro-4-(2-(2-(dimethylamino)-2-oxoacetyl)phenylamino)pyrimidin-2-ylamino)-4-methoxyphenyl)acrylamide;
68) N-(5-(5-chloro-4-(2-(2-(methylamino)-2-oxoacetyl)phenylamino)pyrimidin-2-ylamino)-4-fluoro-2-methoxyphenyl)acrylamide;
69) N-(5-(5-chloro-4-(2-(2-(dimethylamino)-2-oxoacetyl)phenylamino)pyrimidin-2-ylamino)-4-fluoro-2-methoxyphenyl)acrylamide;
70) (E)-N-(3-(5-chloro-4-(2-(2-(dimethylamino)-2-oxoacetyl)phenylamino)pyrimidin-2-ylamino)-4-methoxyphenyl)but-2-enamide;
71) N-(3-(5-chloro-4-(2-(2-(dimethylamino)-2-oxoacetyl)phenylamino)pyrimidin-2-ylamino)-4-methoxyphenyl)-3-methylbut-2-enamide;
72) (E)-N-(3-(5-chloro-4-(2-(2-(dimethylamino)-2-oxoacetyl)phenylamino)pyrimidin-2-ylamino)-4-methoxyphenyl)-4-(piperidin-1-yl)but-2-enamide;
73) N-(3-(5-chloro-4-(2-(2-(dimethylamino)-2-oxoacetyl)phenylamino)pyrimidin-2-ylamino)-4-methoxyphenyl)-2-(piperidin-1-ylmethyl)acrylamide;
74) N-(5-(5-chloro-4-(2-(2-(dimethylamino)-2-oxoacetyl)phenylamino)pyrimidin-2-ylamino)-4-methoxy-2-(4-methylpiperazin-1-yl)phenyl)acrylamide;
75) N-(5-(5-chloro-4-(2-(2-(methylamino)-2-oxoacetyl)phenylamino)pyrimidin-2-ylamino)-4-m ethoxy-2-(4-methylpiperazin-1-yl)phenyl)acrylamide;
76) N-(3-(5-chloro-4-(2-(2-(2-(dimethylamino)ethylamino)-2-oxoacetyl)phenylamino)pyrimidin-2-ylamino)phenyl)acrylamide;
77) N-(3-(5-chloro-4-(2-(2-(2-(dimethylamino)ethylamino)-2-oxoacetyl)phenylamino)pyrimidin-2-ylamino)-4-methoxyphenyl)acrylamide;
78) N-(3-(5-chloro-4-(2-(2-(dimethylamino)-2-oxoacetyl)phenylamino)pyrimidin-2-ylamino)-4-methoxyphenyl)-2-((dimethylamino)methyl)acrylamide;
79) (E)-N-(3-(5-chloro-4-(2-(2-(dimethylamino)-2-oxoacetyl)phenylamino)pyrimidin-2-ylamino)-4-methoxyphenyl)-4-morpholinobut-2-enamide;
80) (E)-N-(3-(5-chloro-4-(2-(2-(dimethylamino)-2-oxoacetyl)phenylamino)pyrimidin-2-ylamino)-4-methoxyphenyl)-4-(dimethylamino)but-2-enamide;
81) N-(5-(5-chloro-4-(2-(2-(methylamino)-2-oxoacetyl)phenylamino)pyrimidin-2-ylamino)-2-(2-(dimethylamino)ethoxy)-4-methoxyphenyl)acrylamide;
82) N-(5-(5-chloro-4-(2-(2-(dimethylamino)-2-oxoacetyl)phenylamino)pyrimidin-2-ylamino)-2-(2-(dimethylamino)ethoxy)-4-methoxyphenyl)acrylamide;
83) N-(5-(5-chloro-4-(2-(2-(dimethylamino)-2-oxoacetyl)phenylamino)pyrimidin-2-ylamino)-4-methoxy-2-(3-morpholinopropoxy)phenyl)acrylamide;
84) N-(5-(5-chloro-4-(2-(2-(methylamino)-2-oxoacetyl)phenylamino)pyrimidin-2-ylamino)-4-methoxy-2-(3-morpholinopropoxy)phenyl)acrylamide;
85) N-(3-(5-chloro-4-(2-(2-morpholino-2-oxoacetyl)phenylamino)pyrimidin-2-ylamino)-4-methoxyphenyl)acrylamide;
86) N-(5-(5-chloro-4-(2-(2-(2-(dimethylamino)ethylamino)-2-oxoacetyl)phenylamino)pyrimidin-2-ylamino)-2-methoxyphenyl)acrylamide;
87) 2-(2-(2-(4-acryloyl-3,4-dihydro-2H-benzo[b][1,4]oxazin-6-ylamino)-5-chloropyrimidin-4-yl amino)phenyl)-N,N-dimethyl-2-oxoacetamide;
88) 2-(2-(2-(4-(4-acryloylpiperazin-1-yl)-2-methoxyphenylamino)-5-chloropyrimidin-4-ylamino)phenyl)-N,N-dimethyl-2-oxoacetamide;
89) N-(3-(5-chloro-4-(2-(2-(4-methylpiperazin-1-yl)-2-oxoacetyl)phenylamino)pyrimidin-2-ylamino)-4-methoxyphenyl)acrylamide;
90) N-(3-(5-chloro-4-(2-(2-morpholino-2-oxoacetyl)phenylamino)pyrimidin-2-ylamino)phenyl)acrylamide;
91) N-(3-(5-chloro-4-(2-(2-(4-methylpiperazin-1-yl)-2-oxoacetyl)phenylamino)pyrimidin-2-ylamino)phenyl)acrylamide;
92) N-(5-(5-chloro-4-(2-(2-morpholino-2-oxoacetyl)phenylamino)pyrimidin-2-ylamino)-2-methoxyphenyl)acrylamide;
93) N-(5-(5-chloro-4-(2-(2-(4-methylpiperazin-1-yl)-2-oxoacetyl)phenylamino)pyrimidin-2-ylamino)-2-methoxyphenyl)acrylamide;
94) 2-(2-(2-(4-(4-acetylpiperazin-1-yl)-3-methoxyphenylamino)-5-chloropyrimidin-4-ylamino)phenyl)-N,N-dimethyl-2-oxoacetamide;
95) 2-(aziridin-1-ylmethyl)-N-(3-(5-chloro-4-(2-(2-(dimethylamino)-2-oxoacetyl)phenylamino)pyrimidin-2-ylamino)-4-methoxyphenyl)acrylamide;
96) 2-(azetidin-1-ylmethyl)-N-(3-(5-chloro-4-(2-(2-(dimethylamino)-2-oxoacetyl)phenylamino)pyrimidin-2-ylamino)-4-methoxyphenyl)acrylamide;
97) N-(3-(5-chloro-4-(2-(2-(dimethylamino)-2-oxoacetyl)phenylamino)pyrimidin-2-ylamino)-4-methoxyphenyl)-2-(pyrrolidin-1-ylmethyl)acrylamide;
98) N-(5-(5-chloro-4-(2-(2-(dimethylamino)-2-oxoacetyl)phenylamino)pyrimidin-2-ylamino)-4-methoxy-2-(2-morpholinoethoxy)phenyl)acrylamide;
99) N-(5-(5-chloro-4-(2-(2-(dimethylamino)-2-oxoacetyl)phenylamino)pyrimidin-2-ylamino)-2-((2-(dimethylamino)ethyl)(methyl)amino)phenyl)acrylamide;
100) N-(3-(4-(2-(2-(dimethylamino)-2-oxoacetyl)phenylamino)-5-methylpyrimidin-2-ylamino)-4-methoxyphenyl)-2-((dimethylamino)methyl)acrylamide;

101) N-(5-(4-(2-(2-(dimethylamino)-2-oxoacetyl)phenylamino)-5-methylpyrimidin-2-ylamino)-2-methoxyphenyl)acrylamide;
102) N-(5-(5-chloro-4-(2-(2-((2-(dimethylamino)ethyl)(methyl)amino)-2-oxoacetyl)phenylamino)pyrimidin-2-ylamino)-2-methoxyphenyl)acrylamide;
103) N-(5-(5-chloro-4-(2-(2-(dimethylamino)-2-oxoacetyl)phenylamino)pyrimidin-2-ylamino)-2-(2-(dimethylamino)ethoxy)phenyl)-3-methoxypropanamide;
104) N-(5-(5-chloro-4-(2-(2-(dimethylamino)-2-oxoacetyl)phenylamino)pyrimidin-2-ylamino)-2-cyclopropoxyphenyl)acrylamide;
105) N-(5-(5-chloro-4-(2-(2-(dimethylamino)-2-oxoacetyl)phenylamino)pyrimidin-2-ylamino)-2-(cyclopentyloxy)phenyl)acrylamide;
106) N-(5-(5-chloro-4-(2-(2-(dimethylamino)-2-oxoacetyl)phenylamino)pyrimidin-2-ylamino)-2-(1-methylpyrrolidin-3-yloxy)phenyl)acrylamide;
107) N-(5-(5-chloro-4-(2-(2-(dimethylamino)-2-oxoacetyl)phenylamino)pyrimidin-2-ylamino)-2-(4-(dimethylamino)cyclohexyloxy)phenyl)acrylamide;
108) N-(2-(azetidin-3-yloxy)-5-(5-chloro-4-(2-(2-(dimethylamino)-2-oxoacetyl)phenylamino)pyrimidin-2-ylamino)phenyl)acrylamide;
109) N-(5-(5-chloro-4-(2-(2-(dimethylamino)-2-oxoacetyl)phenylamino)pyrimidin-2-ylamino)-2-(1-methylazetidin-3-yloxy)phenyl)acrylamide;
110) N-(5-(5-chloro-4-(2-(2-(dimethylamino)-2-oxoacetyl)phenylamino)pyrimidin-2-ylamino)-2-morpholinophenyl)acrylamide;
111) N-(5-(5-chloro-4-(2-(2-(dimethylamino)-2-oxoacetyl)phenylamino)pyrimidin-2-ylamino)-2-(4-methylpiperazin-1-yl)phenyl)acrylamide;
112) N-(3-(5-chloro-4-(2-(2-(dimethylamino)-2-oxoacetyl)phenylamino)pyrimidin-2-ylamino)phenyl)-2-(morpholinomethyl)acrylamide;
113) N-(3-(5-chloro-4-(2-(2-(dimethylamino)-2-oxoacetyl)phenylamino)pyrimidin-2-ylamino)phenyl)-2-(piperidin-1-ylmethyl)acrylamide;
114) (E)-N-(3-(5-chloro-4-(2-(2-(dimethylamino)-2-oxoacetyl)phenylamino)pyrimidin-2-ylamino)phenyl)-4-(dimethylamino)but-2-enamide;
115) N-(5-(5-chloro-4-(2-(2-(dimethylamino)-2-oxoacetyl)phenylamino)pyrimidin-2-ylamino)-2-(2-(dimethylamino)ethoxy)phenyl)acrylamide;
116) N-(5-(5-chloro-4-(2-(2-(dimethylamino)-2-oxoacetyl)phenylamino)pyrimidin-2-ylamino)-2-(difluoromethoxy)phenyl)acrylamide;
117) 2-(2-(5-chloro-2-(3-methoxy-4-morpholinophenylamino)pyrimidin-4-ylamino)phenyl)-N,N-dimethyl-2-oxoacetamide;
118) 2-(2-(5-chloro-2-(4-(4-(dimethylamino)piperidin-1-yl)-3-methoxyphenylamino)pyrimidin-4-ylamino)phenyl)-N,N-dimethyl-2-oxoacetamide;
119) 2-(2-(5-chloro-2-(4-(4-methylpiperazin-1-yl)phenylamino)pyrimidin-4-ylamino)phenyl)-N,N-dimethyl-2-oxoacetamide;
120) N-(5-(5-chloro-4-(2-(2-(dimethylamino)-2-oxoacetyl)phenylamino)pyrimidin-2-ylamino)-2-(2-(dimethylamino)ethoxy)phenyl)propionamide;
121) (E)-N-(5-(5-chloro-4-(2-(2-(dimethylamino)-2-oxoacetyl)phenylamino)pyrimidin-2-ylamino)-2-(4-methylpiperazin-1-yl)phenyl)-3-(dimethylamino)acrylamide;
122) N-(5-(5-chloro-4-(2-(2-(dimethylamino)-2-oxoacetyl)phenylamino)pyrimidin-2-ylamino)-2-propoxyphenyl)acrylamide;
123) N-(5-(5-chloro-4-(2-(2-(dimethylamino)-2-oxoacetyl)phenylamino)pyrimidin-2-ylamino)-2-fluorophenyl)-3-morpholinopropanamide;
124) N-(5-(5-chloro-4-(2-(2-(dimethylamino)-2-oxoacetyl)phenylamino)pyrimidin-2-ylamino)-2-(tetrahydrofuran-3-yloxy)phenyl)acrylamide;
125) N-(3-(5-chloro-4-(2-(2-(dimethylamino)-2-oxoacetyl)phenylamino)pyrimidin-2-ylamino)phenyl)-2-(((2-(dimethylamino)ethyl)(methyl)amino)methyl)acrylamide;
126) N-(3-(5-chloro-4-(2-(2-(dimethylamino)-2-oxoacetyl)phenylamino)pyrimidin-2-ylamino)-4-methoxyphenyl)-2-(((2-(dimethylamino)ethyl)(methyl)amino)methyl)acrylamide;
127) N-(3-(5-chloro-4-(2-(2-((2-(dimethylamino)ethyl)(methyl)amino)-2-oxoacetyl)phenylamino)pyrimidin-2-ylamino)-4-methoxyphenyl)acrylamide;
128) N-(5-(5-chloro-4-(2-(2-(dimethylamino)-2-oxoacetyl)phenylamino)pyrimidin-2-ylamino)-2-(4-methylpiperazin-1-yl)phenyl)-2-(piperidin-1-ylmethyl)acrylamide;
129) N-(5-(5-chloro-4-(2-(2-(dimethylamino)-2-oxoacetyl)phenylamino)pyrimidin-2-ylamino)-2-morpholinophenyl)-2-(piperidin-1-ylmethyl)acrylamide;
130) 2-(2-(5-chloro-2-(3-methoxy-4-(4-methylpiperazin-1-yl)phenylamino)pyrimidin-4-ylamino)phenyl)-N,N-diethyl-2-oxoacetamide;
131) N-(3-(5-chloro-4-(2-(2-(diethylamino)-2-oxoacetyl)phenylamino)pyrimidin-2-ylamino)-4-methoxyphenyl)acrylamide;
132) N-(5-(5-chloro-4-(2-(2-(diethylamino)-2-oxoacetyl)phenylamino)pyrimidin-2-ylamino)-2-methoxyphenyl)acrylamide;
133) N-(3-(5-chloro-4-(2-(2-(dimethylamino)-2-oxoacetyl)phenylamino)pyrimidin-2-ylamino)-5-(trifluoromethyl)phenyl)acrylamide;
134) N-(3-(5-chloro-4-(2-(2-(dimethylamino)-2-oxoacetyl)phenylamino)pyrimidin-2-ylamino)-4-((2-(dimethylamino)ethyl)(methyl)amino)phenyl)acrylamide;
135) N-(3-(5-chloro-4-(2-(2-(dimethylamino)-2-oxoacetyl)phenylamino)pyrimidin-2-ylamino)-4-(4-methylpiperazin-1-yl)phenyl)acrylamide;
136) N-(3-(5-chloro-4-(2-(2-(dimethylamino)-2-oxoacetyl)phenylamino)pyrimidin-2-ylamino)-4-(tetrahydrofuran-3-yloxy)phenyl)acrylamide;
137) N-(5-(5-chloro-4-(2-(2-(dimethylamino)-2-oxoacetyl)phenylamino)pyrimidin-2-ylamino)-2-((2-(dimethylamino)ethoxy)methyl)phenyl)acrylamide;
138) N-(5-(5-chloro-4-(2-(2-(dimethylamino)-2-oxoacetyl)phenylamino)pyrimidin-2-ylamino)-2-((2-(dimethylamino)ethoxy)methyl)-4-methoxyphenyl)acrylamide;
139) N-(5-(5-chloro-4-(2-(2-(dimethylamino)-2-oxoacetyl)phenylamino)pyrimidin-2-ylamino)-2-((dimethylamino)methyl)phenyl)acrylamide;
140) N-(5-(5-chloro-4-(2-(2-(dimethylamino)-2-oxoacetyl)phenylamino)pyrimidin-2-ylamino)-2-((dimethylamino)methyl)-4-methoxyphenyl)acrylamide;
141) N-(5-(5-chloro-4-(2-(2-(dimethylamino)-2-oxoacetyl)phenylamino)pyrimidin-2-ylamino)-2-((4-methylpiperazin-1-yl)methyl)phenyl)acrylamide;
142) N-(5-(5-chloro-4-(2-(2-(dimethylamino)-2-oxoacetyl)phenylamino)pyrimidin-2-ylamino)-4-methoxy-2-((4-methylpiperazin-1-yl)methyl)phenyl)acrylamide;
143) N-(5-(5-chloro-4-(2-(2-(dimethylamino)-2-oxoacetyl)phenylamino)pyrimidin-2-ylamino)-2-(1-methylpiperidin-4-yl)phenyl)acrylamide;
144) N-(5-(5-chloro-4-(2-(2-(dimethylamino)-2-oxoacetyl)phenylamino)pyrimidin-2-ylamino)-4-methoxy-2-(1-methylpiperidin-4-yl)phenyl)acrylamide;

145) 2-(2-(5-chloro-2-(3-methoxy-4-(1-methylpiperidin-4-yl)phenylamino)pyrimidin-4-ylamino)phenyl)-N,N-dimethyl-2-oxoacetamide;
146) 2-(2-(2-(4-(1-acetylpiperidin-4-yl)-3-methoxyphenylamino)-5-chloropyrimidin-4-ylamino)phenyl)-N,N-dimethyl-2-oxoacetamide;
147) N-(5-(5-chloro-4-(2-(2-(dimethylamino)-2-oxoacetyl)phenylamino)pyrimidin-2-ylamino)-2-(2-(dimethylamino)ethyl)phenyl)acrylamide;
148) N-(5-(5-chloro-4-(2-(2-(dimethylamino)-2-oxoacetyl)phenylamino)pyrimidin-2-ylamino)-2-(3-(dimethylamino)propyl)phenyl)acrylamide;
149) 2-(2-(5-chloro-2-(4-(1-isopropylpiperidin-4-yl)-3-methoxyphenylamino)pyrimidin-4-ylamino)phenyl)-N,N-dimethyl-2-oxoacetamide;
150) 2-(2-(5-chloro-2-(2-isopropoxy-5-methyl-4-(piperidin-4-yl)phenylamino)pyrimidin-4-ylamino)phenyl)-N,N-dimethyl-2-oxoacetamide.

The present invention also provides a pharmaceutical composition comprising a compound of any of claims 1-48 and a pharmaceutically acceptable excipient. such as hydroxypropyl methyl cellulose. In the composition, the said compound in a weight ratio to the said excipient within the range form about 0.0001 to about 10.

The present invention additionally provided a use of a pharmaceutical composition of Formula (I) or Formula (II) for the preparation of a medicament for treating a disease in a subject.

The present invention further provides some preferred technical solutions with regard to above-mentioned uses.

In some embodiments, a medicament thus prepared can be used for the treatment or prevention of, or for delaying or preventing onset or progression in, cancer, cancer metastasis, cardiovascular disease, an immunological disorder or an ocular disorder.

In some embodiments, a medicament thus prepared can be used for t inhibiting a kinase.

In some embodiments, the kinase comprises EGFR, ALK, ALK fusion proteins, Flt3, Jak3, Blk, Bmx, Btk, HER2 (ErbB2), HER4 (ErbB4), Itk, Tec, or Txk.

In some embodiments, the EGFR is a mutant EGFR; the cancer is EGFR-driven cancer, and the EGFR-driven cancer is characterized by the presence of one or more mutations selected from: (i) L858R, (ii) T790M, (iii) both L858R and T790M, (iv) delE746_A750, or (v) both delE746_A750 and T790M.

In some embodiments, the EGFR-driven cancer is a non-small cell lung cancer (NSCLS), glioblastoma, pancreatic cancer, head and neck cancer (e.g., squamous cell carcinoma), breast cancer, colorectal cancer, epithelial cancer, ovarian cancer, prostate cancer, or an adenocarcinoma.

In some embodiments, the ALK fusion proteins is MEL4-ALK or NPM-ALK kinases.

In some embodiments, the subject is a human.

The present invention also provides a method of inhibiting a kinase in a subject, comprising administering a compound of Formula (I) or Formula (II) or above-mentioned pharmaceutical composition.

The present invention further provides some preferred technical solutions with regard to above-mentioned methods.

In some embodiments, the kinase comprises EGFR, ALK, ALK fusion proteins, Flt3, Jak3, Blk, Bmx, Btk, HER2 (ErbB2), HER4 (ErbB4), Itk, Tec, or Txk.

In some embodiments, the EGFR is a mutant EGFR, the ALK fusion proteins is MEL4-ALK or NPM-ALK kinases.

The present invention also provides a method of treating a disease in a subject comprising administering to the subject a compound of Formula I or Formula II or above-mentioned pharmaceutical composition.

The present invention further provides some preferred technical solutions with regard to above-mentioned methods.

In some embodiments, the disease is caused by kinase regulation disorder, and the kinase comprises EGFR, ALK, ALK fusion proteins, Flt3, Jak3, Blk, Bmx, Btk, HER2 (ErbB2), HER4 (ErbB4), Itk, Tec, or Txk.

In some embodiments, the disease is EGFR-driven cancer, and the EGFR-driven cancer is characterized by the presence of one or more mutations selected from: (i) L858R, (ii) T790M, (iii) both L858R and T790M, (iv) delE746_A750, or (v) both delE746_A750 and T790M.

In some embodiments, the EGFR-driven cancer is a non-small cell lung cancer (NSCLS), glioblastoma, pancreatic cancer, head and neck cancer (e.g., squamous cell carcinoma), breast cancer, colorectal cancer, epithelial cancer, ovarian cancer, prostate cancer, or an adenocarcinoma.

In some embodiments, the ALK fusion proteins is MEL4-ALK or NPM-ALK kinases.

In some embodiments, the subject is a human.

By "EGFR-driven cancer" is meant a cancer characterized by a mutation in an EGFR gene that alters the biological activity of an EGFR nucleic acid molecule or polypeptide, including the specific mutations noted herein. EGFR-driven cancers can arise in any tissue, including brain, blood, connective tissue, liver, mouth, muscle, spleen, stomach, testis, and trachea. EGFR-driven cancers include non-small cell lung cancer (NSCLS), including one or more of squamous cell carcinoma, adenocarcinoma, adenocarcinoma, bronchioloalveolar carcinoma (BAC), BAC with focal invasion, adenocarcinoma with BAC features, and large cell carcinoma; neural tumors, such as glioblastomas; pancreatic cancer; head and neck cancers (e.g., squamous cell carcinoma); breast cancer; colorectal cancer; epithelial cancer, including squamous cell carcinoma; ovarian cancer; prostate cancer; adenocarcinomas; and including cancers which are EGFR mediated.

An "EGFR mutant" or "mutant" includes one or more deletions, substitutions, or additions in the amino acid or nucleotide sequences of EGFR protein, or EGFR coding sequence. The EGFR mutant can also include one or more deletions, substitutions, or additions, or a fragment thereof, as long as the mutant retains or increases tyrosine kinase activity, compared to wild type EGFR. In particular EGFR mutations, kinase or phosphorylation activity can be increased (e.g., by at least 5%, 10%, 15%, 20%, 30%, 40%, 50%, 60%, 70%, 80%, 90%, or even 100%), as compared to wild type EGFR. Particular EGFR mutants are described herein, where mutations are provided relative to the position of an amino acid in human EGFR, as described in the sequence provided in NCBI GenBank Reference Sequence: NP_005219.2.

As used herein, the term "inhibiting the proliferation of a cell expressing an EGFR mutant" refers to measurably slowing, stopping, or reversing the growth rate of the EGFR-expressing cells in vitro or in vivo. Desirably, a slowing of the growth rate is by at least 10%, 20%, 30%, 50%, or even 70%, as determined using a suitable assay for determination of cell growth rates (e.g., a cell growth assay described herein). The EGFR mutant can be any EGFR mutant described herein.

In addition, the present invention provides at least one compound for use in the treatment of cancer, the prevention of cancer metastasis or the treatment of cardiovascular disease, an immunological disorder or an ocular disorder.

The present invention also provides a method of treating a patient having a condition which is mediated by protein kinase activity, said method comprising administering to the patient a therapeutically effective amount of at least one compound as described herein, or a pharmaceutically acceptable salt thereof. Examples of the protein kinase include mutant EGFR, KDR, Tie-2, Flt3, FGFR3, AbI, Aurora A, c-Src, IGF-IR, ALK, c-MET, RON, PAK1, PAK2, and TAK1.

In some embodiments, the condition mediated by protein kinase activity is cancer.

Examples of cancer include a solid tumor, a sarcoma, fibrosarcoma, osteoma, melanoma, retinoblastoma, a rhabdomyosarcoma, glioblastoma, neuroblastoma, teratocarcinoma, hematopoietic malignancy, and malignant ascites.

Also provided is at least one compound as described herein or a pharmaceutically acceptable salt thereof for use as a medicament.

Further provided is at least one compound as described herein or a pharmaceutically acceptable salt thereof for use in the treatment of cancer.

Additionally provided is a method of treating cancer selected from the group consisting of lung cancer, breast cancer, colorectal cancer, renal cancer, pancreatic cancer, head cancer, neck cancer, hereditary papillary renal cell carcinoma, childhood hepatocellular carcinoma, and gastric cancer in a mammal comprising administering to a mammal in need of such treatment an effective amount of at least one compound described herein or a pharmaceutically acceptable salt thereof.

The term "halogen", as used herein, unless otherwise indicated, means fluoro, chloro, bromo or iodo. The preferred halogen groups include F, Cl and Br.

As used herein, unless otherwise indicated, alkyl includes saturated monovalent hydrocarbon radicals having straight, branched or cyclic moieties. For example, alkyl radicals include methyl, ethyl, propyl, isopropyl, cyclcopropyl, n-butyl, isobutyl, sec-butyl, t-butyl, cyclcobutyl, n-pentyl, 3-(2-methyl) butyl, 2-pentyl, 2-methylbutyl, neopentyl, cyclcopentyl, n-hexyl, 2-hexyl, 2-methylpentyl and cyclohexyl. Similarly, $C_{1-8}$, as in $C_{1-8}$alkyl is defined to identify the group as having 1, 2, 3, 4, 5, 6, 7 or 8 carbon atoms in a linear or branched arrangement.

Alkenyl and alkynyl groups include straight, branched chain or cyclic alkenes and alkynes. Likewise, "$C_{2-8}$ alkenyl" and "$C_{2-8}$ alkynyl" means an alkenyl or alkynyl radicals having 2, 3, 4, 5, 6, 7 or 8 carbon atoms in a linear or branched arrangement.

Alkoxy radicals are oxygen ethers formed from the previously described straight, branched chain or cyclic alkyl groups.

The term "aryl", as used herein, unless otherwise indicated, refers to an unsubstituted or substituted mono- or polycyclic ring system containing carbon ring atoms. The preferred aryls are mono cyclic or bicyclic 6-10 membered aromatic ring systems. Phenyl and naphthyl are preferred aryls. The most preferred aryl is phenyl.

The term "heterocyclyl", as used herein, unless otherwise indicated, represents an unsubstituted or substituted stable three to eight membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heterocyclyl group may be attached at any heteroatom or carbon atom which results in the creation of a stable structure. Examples of such heterocyclyl groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an unsubstituted or substituted stable five or six membered monocyclic aromatic ring system or an unsubstituted or substituted nine or ten membered benzofused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom which results in the creation of a stable structure. Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "carbonyl" refers to the group C(O).

The term "alkoxycarbonyl" refers to straight or branched chain esters of a carboxylic acid derivative of the present invention of the number of carbon atoms specified (e.g., $C_{1-6}$ alkoxycarbonyl), or any number within this range (e.g., methyloxycarbonyl(MeOCO—), ethyloxycarbonyl, or butyloxycarbonyl).

Whenever the term "alkyl" or "aryl" or either of their prefix roots appear in a name of a substituent (e.g., aralky or dialkylamino) it shall be interpreted as including those limitations given above for "alkyl" and "aryl." Designated numbers of carbon atoms (e.g., $C_{1-6}$) shall refer independently to the number of carbon atoms in an alkyl moiety or to the alkyl portion of a larger substituent in which alkyl appears as its prefix root.

The term "alkylsulphinyl" refers to straight or branched chain alkylsulfoxides of the number of carbon atoms specified (e.g., $C_{1-6}$ alkylsulfinyl), or any number within this range (e.g., methylsulphinyl (MeSO—), ethylsulphinyl, isopropylsulphinyl).

The term "alkylsulphonyl" refers to straight or branched chain alkylsulfones of the number of carbon atoms specified (e. g., $C_{1-6}$ alkylsulphonyl), or any number within this range [e. g, methylsulphonyl (MeSO$_2$—), ethylsulphonyl, isopropylsulphonyl, etc].

The term "alkylthio" refers to straight or branched chain alkylsulfides of the number of carbon atoms specified (e. g., $C_{1-6}$ alkylthio), or any number within this range [e. g., methylthio (MeS—), ethylthio, isopropylthio, etc].

The term "alkenyloxy" refers to the group —O-alkenyl, where alkenyl is defined as above.

The term "alknyloxy" refers to the group —O-alknyl, where alknyl is defined as above.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula (I) exists, the present invention includes any possible tautomers and pharmaceutically acceptable salts thereof, and mixtures thereof, except where specifically stated otherwise.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid. Since the compounds of Formula (I) are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

EXAMPLES

The following Examples are provided to better illustrate the present invention. All parts and percentages are by weight and all temperatures are degrees Celsius, unless explicitly stated otherwise. The following abbreviations have been used in the examples:

ATP: Adenosine triphosphate;
DIPEA: N,N-Diisopropylethylamine;
DMF: N,N-Dimethylformamide;
DMA: N,N-Dimethyacetamide;
DMAP: 4-N,N-Dimethylamiopryidine;
DMSO: Dimethyl sulfoxide;
DEAD: Diethyl azodicarboxylate;
HATU: O-(7-Azabenzotriazol-1-yl)-N,N,N',N'-tetramethyluronium hexafluorophosphate;
DIPEA: N,N-Diisopropylethylamine;
EDC: 1-ethyl-3-(3-dimethylaminopropyl)carbodiimide;
TBAB: Tetrabutyl ammonium bromide;
TEA: Triethylamine;
EtOAc: Ethyl acetate;
GSR: Glutathione-S-Transferase;
Crk: CT10 (Chicken Tumor Retrovirus 10);
min: Minute;
h or hr: Hour;
rt or RT: room temperature;
SDS, Sodium Dodecyl Sulfate;
SDS-PAGE, Sodium Dodecyl Sulfate PolyAcrylamide Electrophoresis Gel;
TLC, Thin layer chromatography.

Example 1 Synthesis of Compound 1

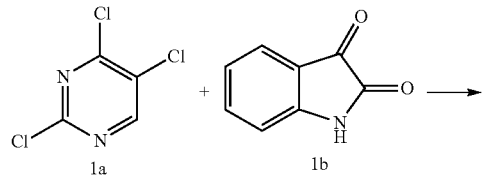

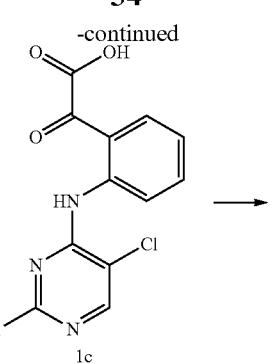

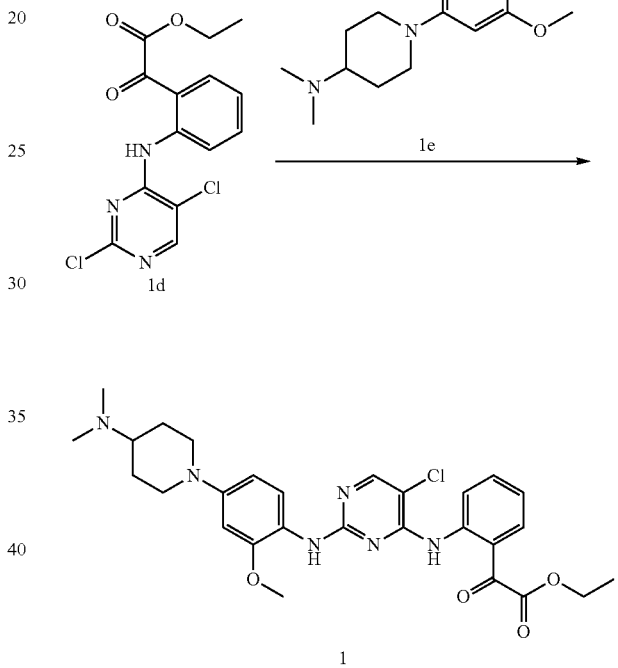

A mixture of Compound 1a (25 g, 0.11 mol), Compound 1b (20 g, 0.11 mol) and K$_2$CO$_3$ (37.5 g, 0.22 mol) in DMF (200 ml) was stirred at 70° C. for 3 hrs. Then H$_2$O (300 ml) was added to the mixture and extracted with EA (200 ml×3), the aqueous layer was acidified with HCl (1 mol/L) to pH 3-4. The precipitate was collected by filtration and washed with methanol (5 ml). After dried under air for 5 hrs, 23 g of Compound 1c was obtained.

(COCl)$_2$ (7.2 ml in 10 ml of DCM) was added to a solution of Compound 1c (5.0 g) and 2 drops of DMF in DCM at ice bath under N$_2$ with stirring. After 3.5 hrs, the solvent was removed. The residue was dissolved in DCM and then added 10 ml of EtOH. After stirring for 1 hr, the reaction mixture was quenched with water. The organic layer was separated and dried, and concentrated. The residue was purified by chromatography to give 4.7 g of Compound 1d as a yellow solid.

A mixture of Compound 1d (200 mg) and Compound 1e was stirred in sealed tube at 130° C. for 1 hr. After the solvent was removed, the residue was purified to give Compound 1. MS: 552.2 (M+H)$^+$.

Example 2 Synthesis of Compound 2

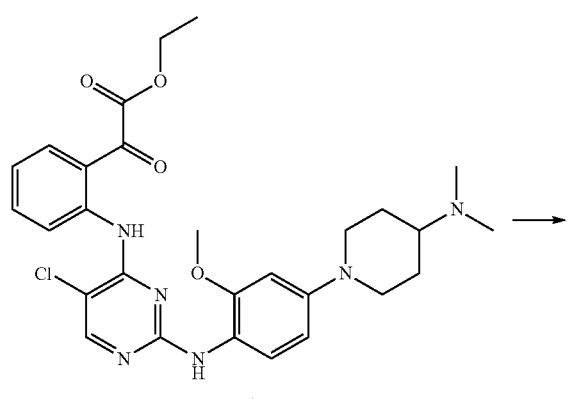

A mixture of Compound 1 and NaOH (0.5 ml, 2 mol/L) in MeOH was stirred at room temperature for 1 hr. Then the solution was acidified with HCl to about pH 5. After filtration, the solid was dried to give the Compound 2 (37 mg). MS: 524.2 (M+H)$^+$.

Example 3 Synthesis of Compound 3

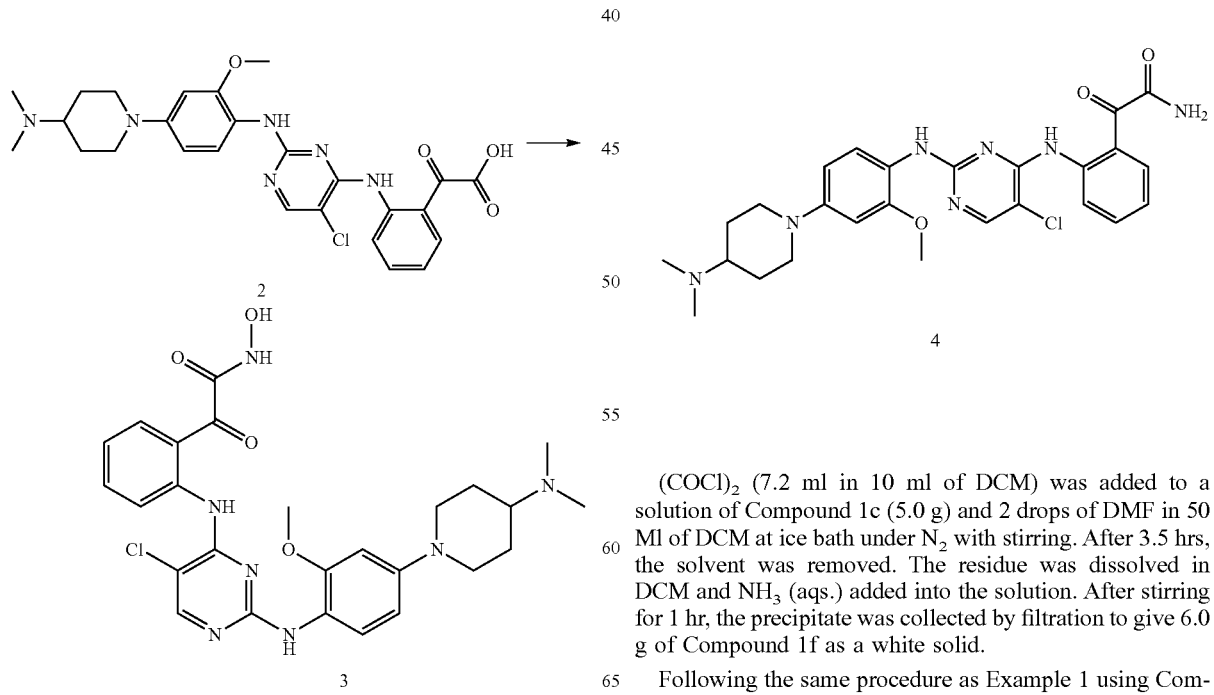

A mixture of Compound 2 (140 mg) and NH$_2$OH (72 mg), PyBOP (180 mg) in 10 mL of DMF was stirred at 45° C. for 3 hrs. Then, the reaction solution was purified by pre-HPLC to give 30 mg of compound 3 as a solid. MS: 539.2 (M+H)$^+$.

Example 4 Synthesis of Compound 4

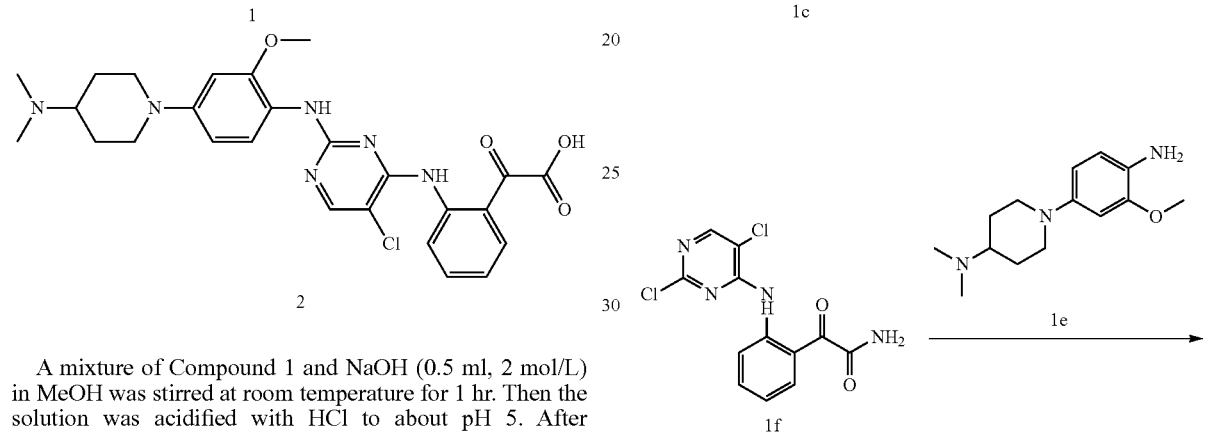

(COCl)$_2$ (7.2 ml in 10 ml of DCM) was added to a solution of Compound 1c (5.0 g) and 2 drops of DMF in 50 Ml of DCM at ice bath under N$_2$ with stirring. After 3.5 hrs, the solvent was removed. The residue was dissolved in DCM and NH$_3$ (aqs.) added into the solution. After stirring for 1 hr, the precipitate was collected by filtration to give 6.0 g of Compound 1f as a white solid.

Following the same procedure as Example 1 using Compound 1f instead of 1d with Compound 1e to yield Compound 4. MS: 523.2 (M+H)$^+$.

| Ex No | Chemical Name | Structure | Physical Data (MS) (M + H)+ |
|---|---|---|---|
| 5 | ethyl 2-(2-(5-chloro-2-(4-(4-(dimethylamino)piperidin-1-yl)-2-methoxyphenylamino)pyrimidin-4-ylamino)phenyl)acrylate | 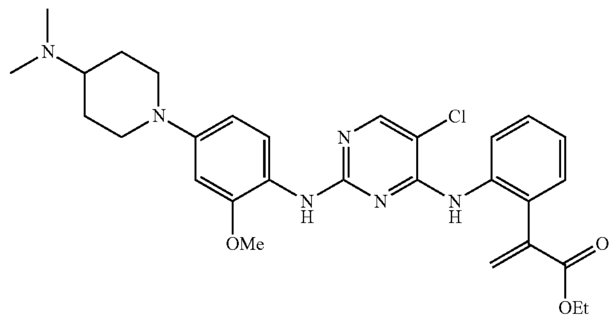 | 552 |
| 6 | 2-(2-((5-chloro-2-((2-methoxy-4-(4-methylpiperazin-1-yl)phenyl)amino)pyrimidin-4-yl)amino)phenyl)-2-oxoacetamide | 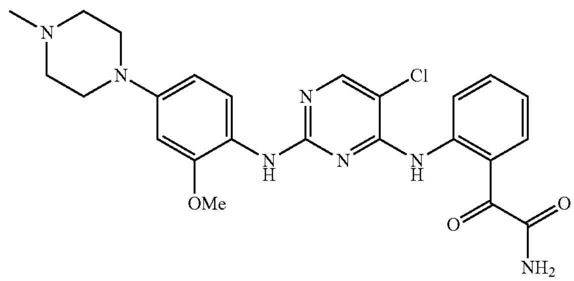 | 496 |
| 7 | 2-(2-((2-((4-(4-acetylpiperazin-1-yl)-2-methoxyphenyl)amino)-5-chloropyrimidin-4-yl)amino)phenyl)-2-oxoacetamide | 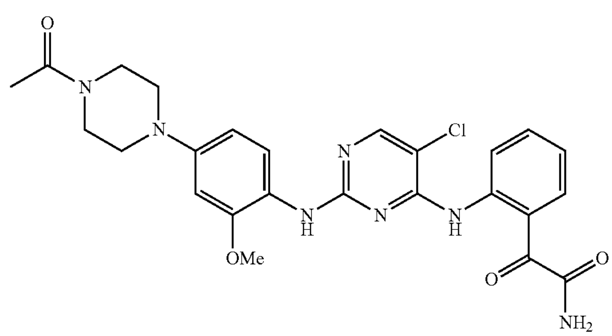 [SMILES: COc1cc(N2CCN(C(C)=O)CC2)ccc1Nc1ncc(Cl)c(Nc2ccccc2C(=O)C(N)=O)n1] | 524 |
| 8 | 2-(2-((5-chloro-2-((2-isopropoxy-5-methyl-4-(piperidin-4-yl)phenyl)amino)pyrimidin-4-yl)amino)phenyl)-2-oxoacetamide | 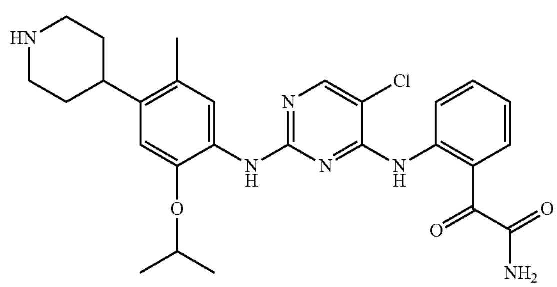 [SMILES: Cc1cc(Nc2ncc(Cl)c(Nc3ccccc3C(=O)C(N)=O)n2)c(OC(C)C)cc1C1CCNCC1] | 523 |
| 9 | 2-(2-((5-chloro-2-((4-((1-(2-fluoroethyl)azetidin-3-yl)amino)-2-methoxyphenyl)amino)pyrimidin-4-yl)amino)phenyl)-2-oxoacetamide | 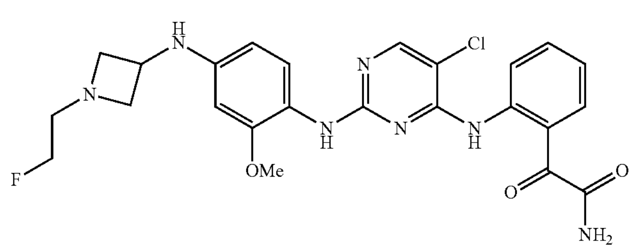 | 514 |

| Ex No | Chemical Name | Structure | Physical Data (MS) (M + H)+ |
|---|---|---|---|
| 10 | 2-(2-((2-((2-methoxy-4-(4-methylpiperazin-1-yl)phenyl)amino)-5-(trifluoromethyl)pyrimidin-4-yl)amino)phenyl)-2-oxoacetamide | 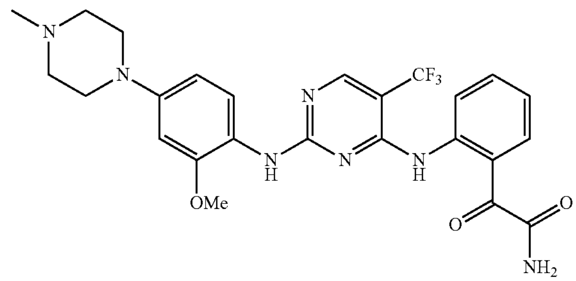 [SMILES: COc1cc(N2CCN(C)CC2)ccc1Nc1ncc(C(F)(F)F)c(Nc2ccccc2C(=O)C(N)=O)n1] | 530 |
| 11 | 2-(2-((2-((4-(4-acetylpiperazin-1-yl)-2-methoxyphenyl)amino)-5-(trifluoromethyl)pyrimidin-4-yl)amino)phenyl)-2-oxoacetamide | 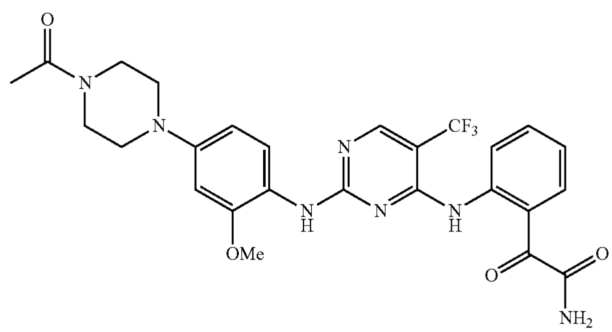 [SMILES: COc1cc(N2CCN(C(C)=O)CC2)ccc1Nc1ncc(C(F)(F)F)c(Nc2ccccc2C(=O)C(N)=O)n1] | 558 |
| 12 | 2-(2-((2-((2-isopropoxy-5-methyl-4-(piperidin-4-yl)phenyl)amino)-5-(trifluoromethyl)pyrimidin-4-yl)amino)phenyl)-2-oxoacetamide | 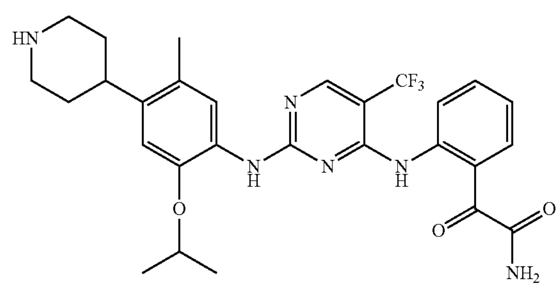 | 557 |
| 13 | 2-(2-((2-((4-((1-(2-fluoroethyl)azetidin-3-yl)amino)-2-methoxyphenyl)amino)-5-(trifluoromethyl)pyrimidin-4-yl)amino)phenyl)-2-oxoacetamide | 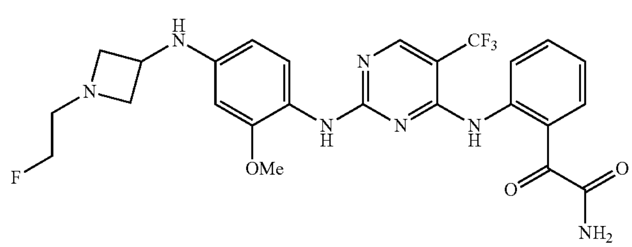 [SMILES: COc1cc(NC2CN(CCF)C2)ccc1Nc1ncc(C(F)(F)F)c(Nc2ccccc2C(=O)C(N)=O)n1] | 548 |
| 14 | 2-(2-((2-((4-(4-(dimethylamino)piperidin-1-yl)-2-methoxyphenyl)amino)-5-(trifluoromethyl)pyrimidin-4-yl)amino)phenyl)-2-oxoacetamide | 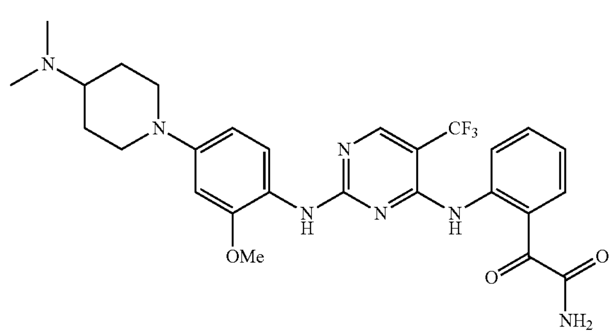 [SMILES: COc1cc(N2CCC(N(C)C)CC2)ccc1Nc1ncc(C(F)(F)F)c(Nc2ccccc2C(=O)C(N)=O)n1] | 558 |

| Ex No | Chemical Name | Structure | Physical Data (MS) (M + H)+ |
|---|---|---|---|
| 15 | 2-(2-((2-((4-(4-(dimethylamino)piperidin-1-yl)-2-methoxyphenyl)amino)-5-(trifluoromethyl)pyrimidin-4-yl)amino)phenyl)-2-oxo-acetic acid | 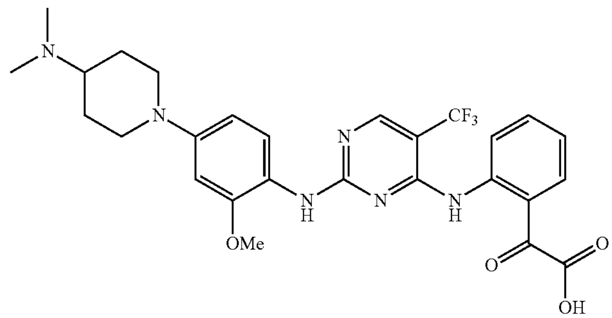 [SMILES: COc1cc(N2CCC(N(C)C)CC2)ccc1Nc1ncc(C(F)(F)F)c(Nc2ccccc2C(=O)C(=O)O)n1] | 559 |
| 16 | 2-(2-((5-chloro-2-((4-(4-(dimethylamino)piperidin-1-yl)-2-methoxyphenyl)amino)pyrimidin-4-yl)amino)phenyl)-N-methyl-2-oxo-acetamide | 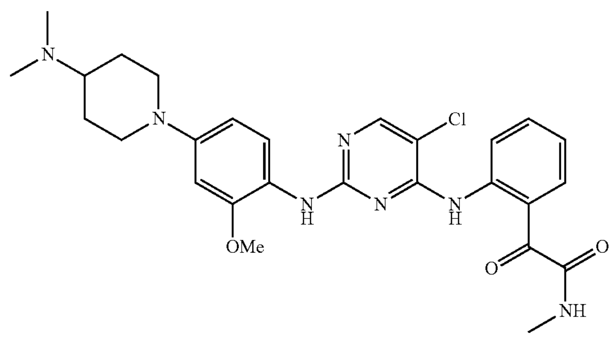 [SMILES: CNC(=O)C(=O)c1ccccc1Nc1nc(Nc2ccc(N3CCC(N(C)C)CC3)cc2OC)ncc1Cl] | 538 |
| 17 | 2-(2-((5-chloro-2-((4-(4-(dimethylamino)piperidin-1-yl)-2-methoxyphenyl)amino)pyrimidin-4-yl)amino)phenyl)-N,N-dimethyl-2-oxoacetamide | 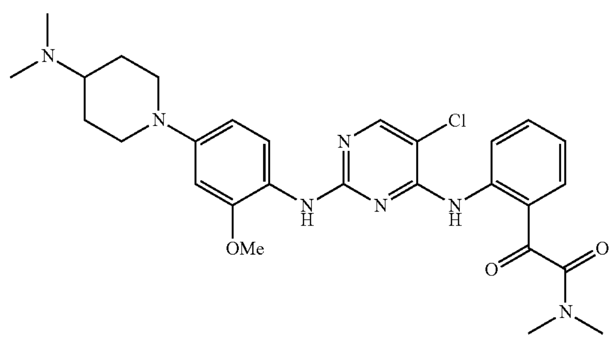 | 552 |
| 18 | 1-(2-((5-chloro-2-((4-(4-(dimethylamino)piperidin-1-yl)-2-methoxyphenyl)amino)pyrimidin-4-yl)amino)phenyl)-2-morpholino-ethane-1,2-dione | 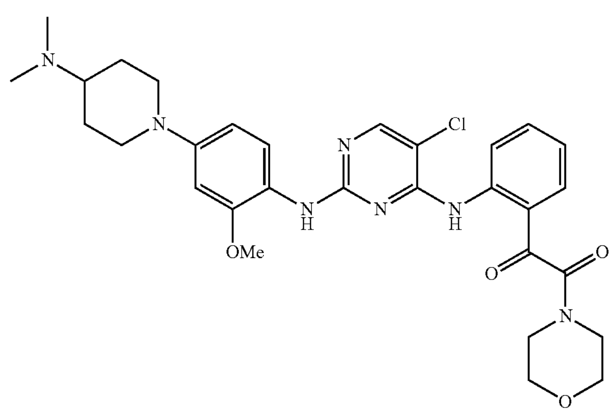 [SMILES: COc1cc(N2CCC(N(C)C)CC2)ccc1Nc1ncc(Cl)c(Nc2ccccc2C(=O)C(=O)N2CCOCC2)n1] | 594 |

-continued

| Ex No | Chemical Name | Structure | Physical Data (MS) (M + H)+ |
|---|---|---|---|
| 19 | 2-(2-((5-chloro-2-((4-(4-(dimethylamino) piperidin-1-yl)-2-methoxyphenyl)amino) pyrimidin-4-yl)amino)phenyl)-N-(2-(dimethylamino)ethyl)-2-oxoacetamide | 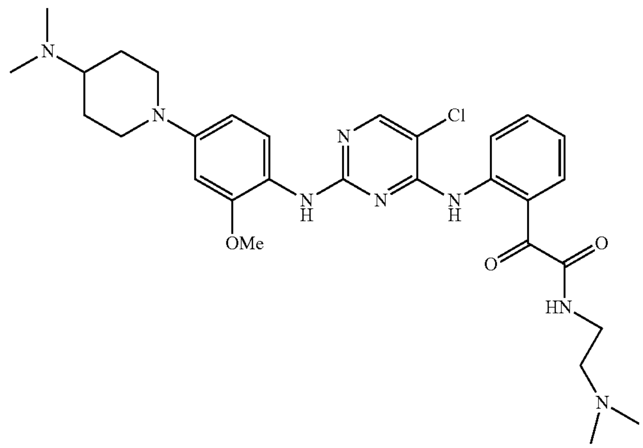 | 595 |
| 20 | 2-(2-((5-chloro-2-((2-methoxy-4-(4-(methyl-amino)piperidin-1-yl)phenyl)amino) pyrimidin-4-yl)amino)phenyl)-N-(2-hydroxyethyl)-2-oxoacetamide | 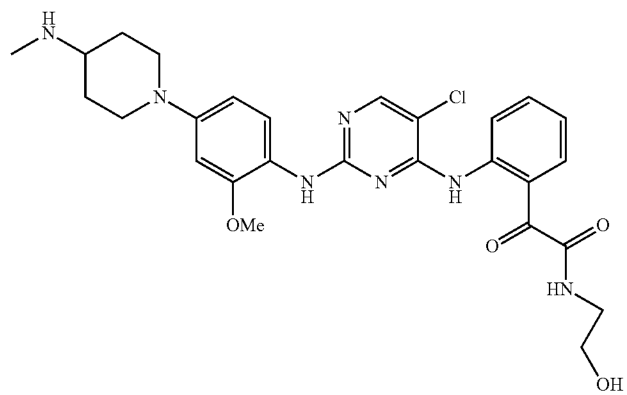 [SMILES: CNC1CCN(c2ccc(Nc3ncc(Cl)c(Nc4ccccc4C(=O)C(=O)NCCO)n3)c(OC)c2)CC1] | 554 |
| 21 | 1-(2-((5-chloro-2-((4-(4-(dimethylamino) piperidin-1-yl)-2-methoxyphenyl)amino) pyrimidin-4-yl)amino)phenyl)-3-methylbutane-1,2-dione | 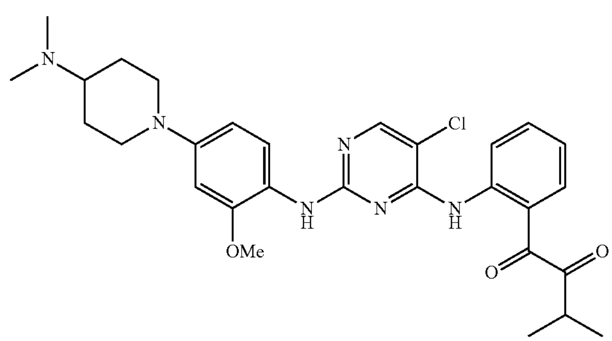 [SMILES: COc1cc(N2CCC(N(C)C)CC2)ccc1Nc1ncc(Cl)c(Nc2ccccc2C(=O)C(=O)C(C)C)n1] | 551 |
| 22 | 1-(2-((5-chloro-2-((4-(4-(dimethylamino) piperidin-1-yl)-2-methoxyphenyl)amino) pyrimidin-4-yl)amino)phenyl)propane-1,2-dione | 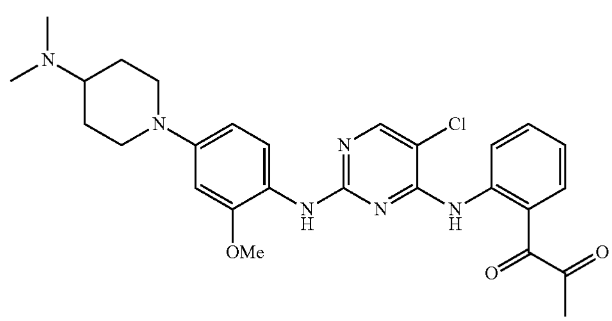 [SMILES: COc1cc(N2CCC(N(C)C)CC2)ccc1Nc1ncc(Cl)c(Nc2ccccc2C(=O)C(C)=O)n1] | 523 |

-continued

| Ex No | Chemical Name | Structure | Physical Data (MS) (M + H)+ |
|---|---|---|---|
| 23 | 1-(2-((5-chloro-2-((4-(4-(dimethylamino)piperidin-1-yl)-2-methoxyphenyl)amino)pyrimidin-4-yl)amino)phenyl)-3-(dimethylamino)propane-1,2-dione | 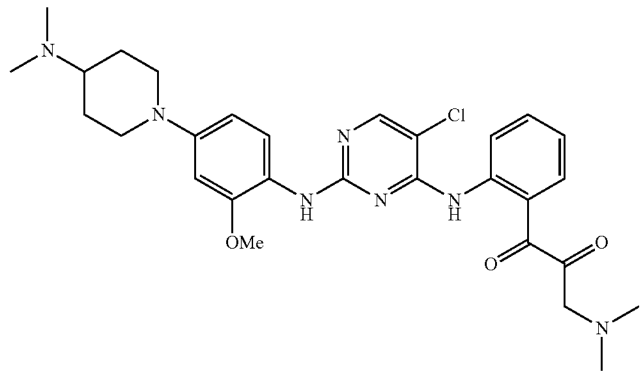 | 566 |
| 24 | N-(azetidin-3-yl)-2-(2-((5-chloro-((4-(4-(dimethylamino)piperidin-1-yl)-2-methoxyphenyl)amino)pyrimidin-4-yl)amino)phenyl)-2-oxoacetamide | 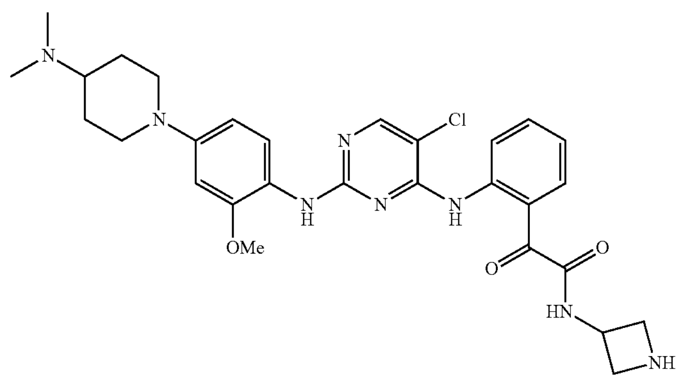 [SMILES: COc1cc(N2CCC(N(C)C)CC2)ccc1Nc1ncc(Cl)c(Nc2ccccc2C(=O)C(=O)NC2CNC2)n1] | 578 |
| 25 | 2-(2-((5-chloro-2-((4-(4-(dimethylamino)piperidin-1-yl)-2-methoxyphenyl)amino)pyrimidin-4-yl)amino)phenyl)-N-cyclopropyl-2-oxoacetamide | 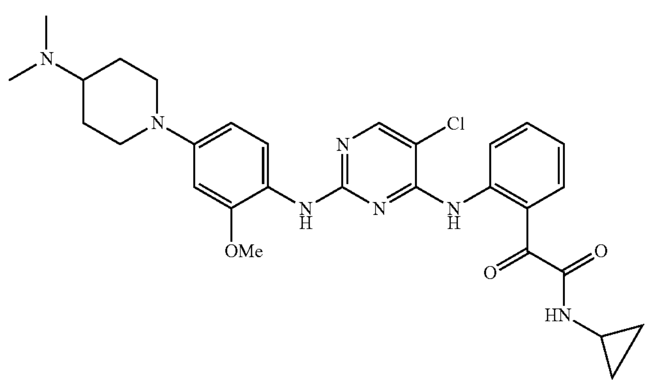 [SMILES: COc1cc(N2CCC(N(C)C)CC2)ccc1Nc1ncc(Cl)c(Nc2ccccc2C(=O)C(=O)NC2CC2)n1] | 564 |
| 26 | 2-(2-((5-chloro-2-((4-(4-(dimethylamino)piperidin-1-yl)-2-methoxyphenyl)amino)pyrimidin-4-yl)amino)phenyl)-2-oxo-N-(pyrrolidin-3-yl)acetamide | 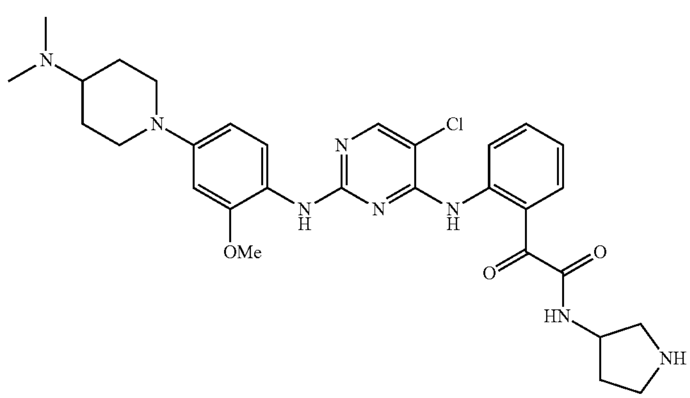 [SMILES: COc1cc(N2CCC(N(C)C)CC2)ccc1Nc1ncc(Cl)c(Nc2ccccc2C(=O)C(=O)NC2CCNC2)n1] | 592 |

| Ex No | Chemical Name | Structure | Physical Data (MS) (M + H)+ |
|---|---|---|---|
| 27 | 2-(2-((5-chloro-2-((4-(4-(dimethylamino) piperidin-1-yl)-2-methoxyphenyl)amino) pyrimidin-4-yl)amino)phenyl)-2-oxo-N- (piperidin-4-yl)acetamide | 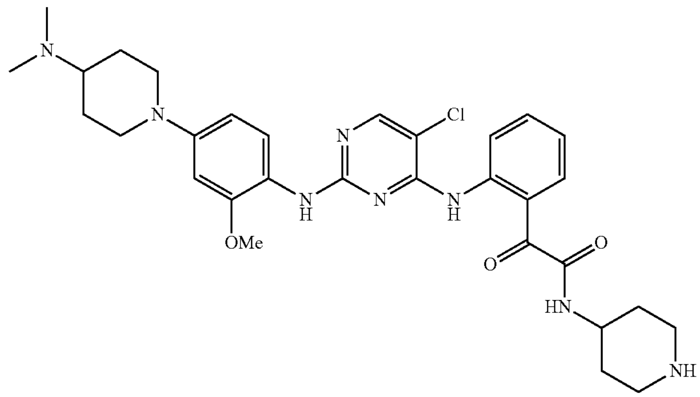 [SMILES: COc1cc(N2CCC(N(C)C)CC2)ccc1Nc1ncc(Cl)c(Nc2ccccc2C(=O)C(=O)NC2CCNCC2)n1] | 607 |
| 28 | 2-(2-((5-chloro-2-((4-(4-(dimethylamino) piperidin-1-yl)-2-methoxyphenyl)amino) pyrimidin-4-yl)amino)phenyl)acrylamide | 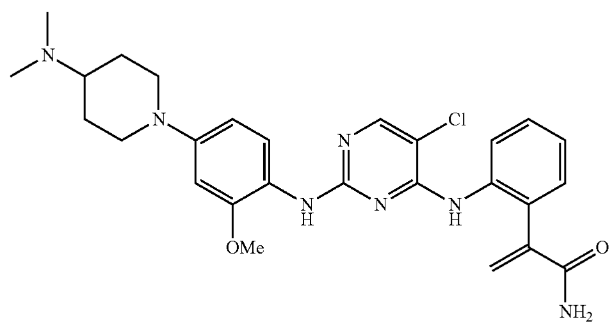 [SMILES: C=C(C(N)=O)c1ccccc1Nc1nc(Nc2ccc(N3CCC(N(C)C)CC3)cc2OC)ncc1Cl] | 522 |
| 29 | 2-(2-((5-chloro-2-((4-(4-(dimethylamino) piperidin-1-yl)-2-methoxyphenyl)amino) pyrimidin-4-yl)amino)phenyl)acrylic acid | 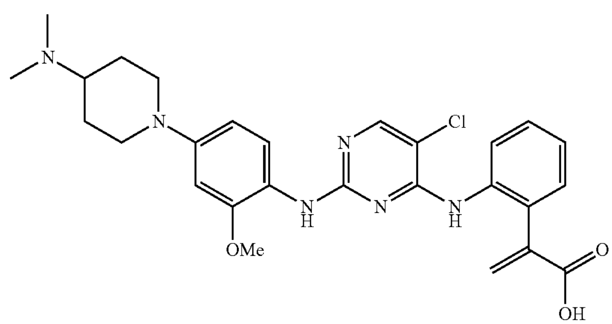 [SMILES: C=C(C(=O)O)c1ccccc1Nc1nc(Nc2ccc(N3CCC(N(C)C)CC3)cc2OC)ncc1Cl] | 523 |
| 30 | 2-(2-((5-chloro-2-((2-methoxy-4-(4-methyl- piperazin-1-yl)phenyl)amino)pyrimidin-4-yl) amino)phenyl)acrylamide | 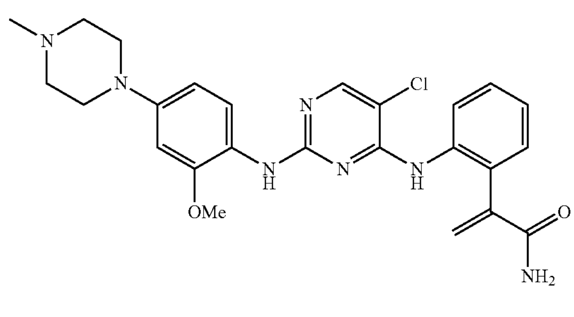 | 494 |

-continued

| Ex No | Chemical Name | Structure | Physical Data (MS) (M + H)+ |
|---|---|---|---|
| 31 | 2-(2-((5-chloro-2-((2-methoxy-4-(4-methyl-piperazin-1-yl)phenyl)amino)pyrimidin-4-yl)amino)phenyl)acrylic acid | 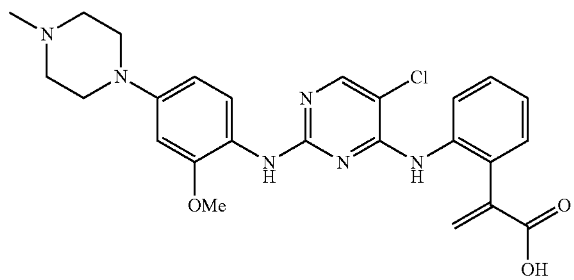 | 495 |
| 32 | 2-(2-((5-chloro-2-((4-((1-(2-fluoroethyl)aze-tidin-3-yl)amino)-2-methoxyphenyl)amino)pyrimidin-4-yl)amino)phenyl)acrylamide | 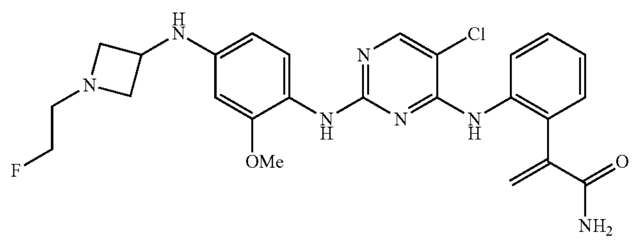 [SMILES: C=C(C(N)=O)c1ccccc1Nc1nc(Nc2ccc(NC3CN(CCF)C3)cc2OC)ncc1Cl] | 512 |
| 33 | 2-(2-((5-chloro-2-((4-((1-(2-fluoroethyl)aze-tidin-3-yl)amino)-2-methoxyphenyl)amino)pyrimidin-4-yl)amino)phenyl)acrylic acid | 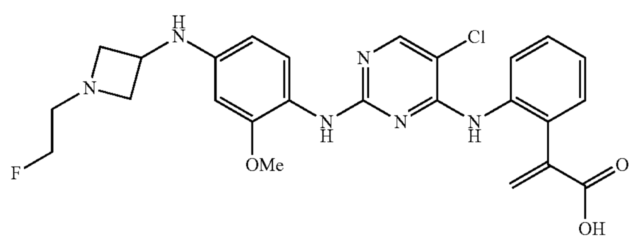 [SMILES: C=C(C(=O)O)c1ccccc1Nc1nc(Nc2ccc(NC3CN(CCF)C3)cc2OC)ncc1Cl] | 513 |
| 34 | 2-(2-((5-chloro-2-((2-methoxy-4-(1-methyl-piperidin-4-yl)phenyl)amino)pyrimidin-4-yl)amino)phenyl)acrylamide | 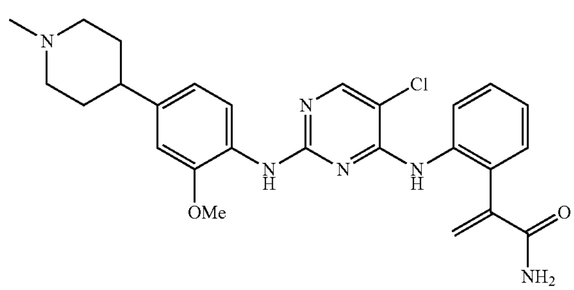 [SMILES: C=C(C(N)=O)c1ccccc1Nc1nc(Nc2ccc(C3CCN(C)CC3)cc2OC)ncc1Cl] | 493 |
| 35 | 2-(2-((5-chloro-2-((2-methoxy-4-(1-methyl-piperidin-4-yl)phenyl)amino)pyrimidin-4-yl)amino)phenyl)acrylic acid | 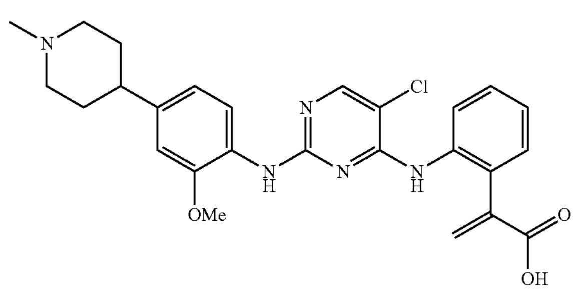 [SMILES: C=C(C(=O)O)c1ccccc1Nc1nc(Nc2ccc(C3CCN(C)CC3)cc2OC)ncc1Cl] | 494 |

| Ex No | Chemical Name | Structure | Physical Data (MS) (M + H)+ |
|---|---|---|---|
| 36 | 2-(2-((5-chloro-2-((2-methoxy-4-(piperidin-4-yl)phenyl)amino)pyrimidin-4-yl)amino)phenyl)acrylamide | 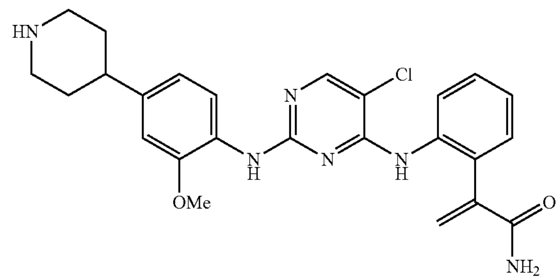 [SMILES: C=C(C(N)=O)c1ccccc1Nc1nc(Nc2ccc(C3CCNCC3)cc2OC)ncc1Cl] | 479 |
| 37 | 2-(2-((5-chloro-2-((2-methoxy-4-(piperidin-4-yl)phenyl)amino)pyrimidin-4-yl)amino)phenyl)acrylic acid | 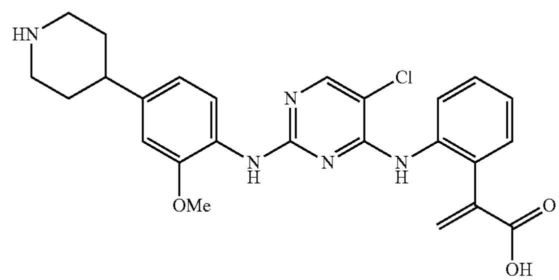 [SMILES: C=C(C(=O)O)c1ccccc1Nc1nc(Nc2ccc(C3CCNCC3)cc2OC)ncc1Cl] | 480 |
| 38 | 2-(2-((5-chloro-2-((4-(4-fluoropiperidin-1-yl)-2-methoxyphenyl)amino)pyrimidin-4-yl)amino)phenyl)acrylamide | 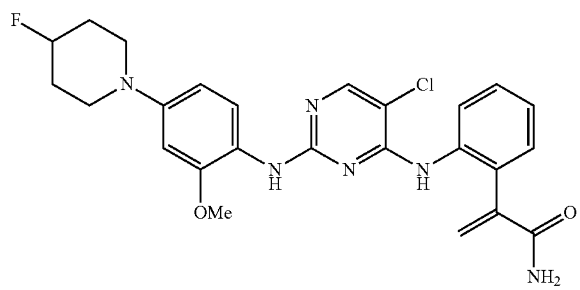 [SMILES: C=C(C(N)=O)c1ccccc1Nc1nc(Nc2ccc(N3CCC(F)CC3)cc2OC)ncc1Cl] | 497 |
| 39 | 2-(2-((5-chloro-2-((2-methoxy-4-(4-methoxy-piperidin-1-yl)phenyl)amino)pyrimidin-4-yl)amino)phenyl)acrylamide | 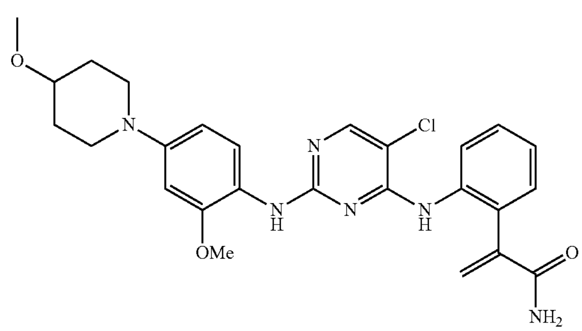 [SMILES: C=C(C(N)=O)c1ccccc1Nc1nc(Nc2ccc(N3CCC(OC)CC3)cc2OC)ncc1Cl] | 509 |

Example 40. Synthesis of Compound 40

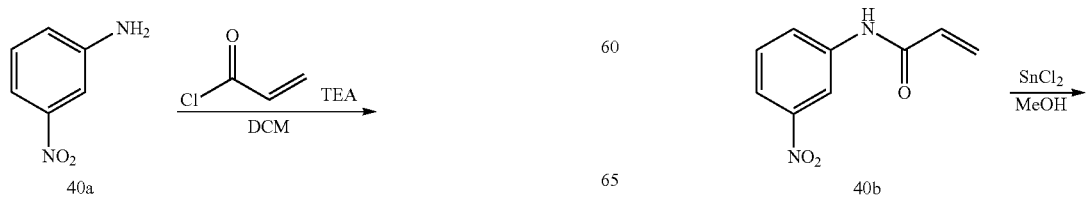

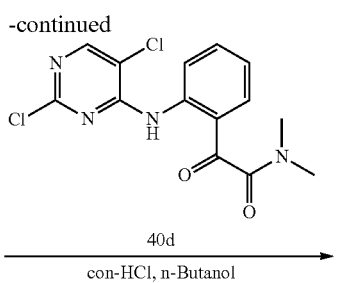

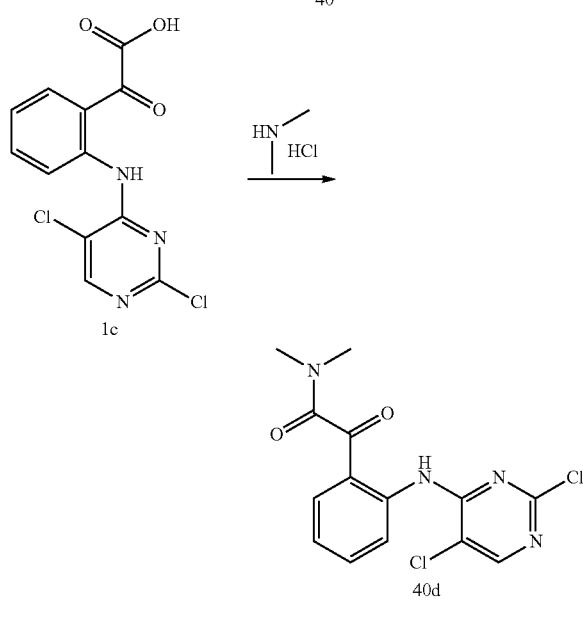

ethyl acetate (50.0 ml) and the aqueous solution of $K_2CO_3$ and filtered. The filtrate was separated and the organic phase was washed with water, dried over $Na_2SO_4$ and evaporated to dryness to give Compound 40c (1.5 g) as a yellow solid.

A mixture of Compound 1c (1.03 g), dimethylamine hydrochloride (0.54 g), HATU (1.51 g), and TEA (1.00 g) in DCM (20 ml) was stirred at 25° C. for 6 hrs. Then, the reaction mixture was concentrated under reduced pressure and the residue was purified by chromatography to give 0.64 g Compound 40d as a yellow solid.

Compound 40d (200 mg), Compound 40c (96 mg), con-HCl (3d) and n-BuOH (60 ml) was stirred at 130° C. in sealed tube until the reaction was complete detected by TLC (DCM:MeOH=10:1). Then, the reaction mixture was washed with water and concentrated under reduced pressure. After, the residue was purified by column chromatography to give 500 mg Compound 40 as a yellow solid. MS: 464.1 $(M+H)^+$. H-NMR (DMSO-d6, 400 MHz): 10.25 (s, 1H), 9.12 (s, 1H), 8.34 (s, 1H), 7.98 (s, 1H), 7.39-7.33 (m, 2H), 7.24-7.19 (m, 2H), 6.54-6.51 (m, 2H), 6.49-6.47 (m, 1H), 6.54-6.47 (m, 1H), 6.25-6.21 (dd, 1H), 5.74-5.71 (dd, 1H), 3.00 (s, 3H), 2.90 (s, 3H).

Example 41. Synthesis of Compound 41

Method 1

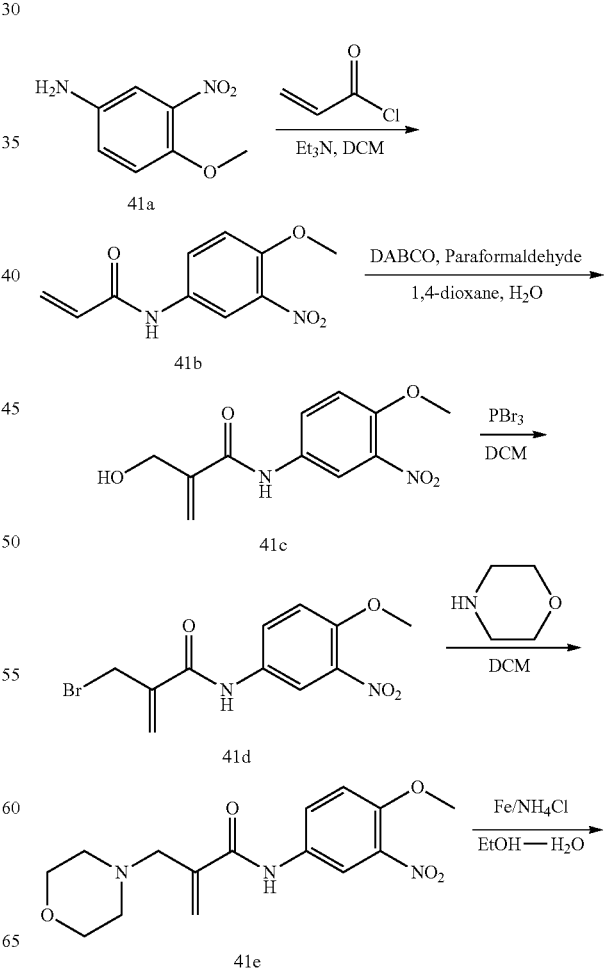

A three-necked round bottom flask equipped with mechanical stirrer, addition funnel and thermometer was charged with Compound 40a (10.0 g), TEA (12.0 ml) and DCM (30.0 ml). And then a solution of acryloyl chloride (5.9 g) in DCM (20.0 ml) was added dropwise (via addition funnel) after the reaction mixture was cooled to −10° C. The reaction mixture was stirred at −10° C. until the reaction was complete detected by TLC (PE:EA=3:1). Then, the reaction was quenched by water (30.0 ml) and filtered to give the crude product of Compound 40b (8.5 g) used for the next reaction directly.

A three-necked round bottom flask equipped with mechanical stirrer, addition funnel and thermometer was charged with Compound 40b (2.0 g), $SnCl_2$ (14.1 g) and MeOH (60.0 ml). Then, the reaction mixture was stirred at 80° C. until the reaction was complete detected by TLC (DCM:MeOH=10:1). After, the reaction mixture was concentrated under reduced pressure and partitioned between

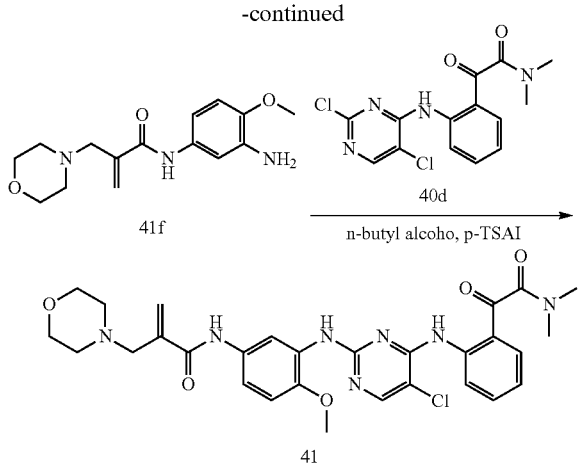

A mixture of 4-methoxy-3-nitroaniline (1.52 g, 9.04 mmol), triethylamine (1.37 g, 13.54 mmol) and DCM (60 ml) was cooled to 0° C., acryloyl chloride (0.90 g, 9.94 mmol) solution in DCM (20 mL) was added dropwise, the resulting mixture was stirred at 0~5° C. for 20 mins. The progress of the reaction was monitored by TLC. Reaction was quenched with water (50 ml), the aqueous solution was extracted with DCM (30 ml×2). The combined organic phase was dried over anhydrous Na₂SO₄, concentrated under reduced pressure to give 1.52 g Compound 41b as a yellow solid.

A mixture of Compound 41b (1.50 g, 6.75 mmol), 1,4-Diazabicyclo[2.2.2]octane (2.27 g, 20.25 mmol), paraformaldehyde (1.01 g, 33.75 mmol), 1,4-dioxane (100 ml) and water (60 ml) was heated to 80° C. for 15 h. Water (100 ml) was added, the resulting mixture was extracted with EA (100 ml×2). The combined organic phase was washed with brine (100 ml), dried over anhydrous Na₂SO₄, concentrated under reduced pressure, the residue was purified by column chromatography to give 1.25 g Compound 41c as a yellow solid.

A mixture of Compound 41c (1.20 g, 4.76 mmol) and DCM (130 ml) was cooled to 0° C., phosphorus tribromide (1.54 g, 5.71 mmol) solution in DCM (20 ml) was then added dropwise and quenched with water (50 ml) after 15 mins, the aqueous solution was extracted with DCM (30 ml×2). The combined organic phase was washed with brine (50 ml×2), dried over anhydrous Na₂SO₄, concentrated under reduced pressure and the residue (Compound 41d) was used for the next step without further purification.

To a solution of Compound 41d (1.35 g) in DCM (100 ml) was added morpholine (1.86 g, 21.40 mmol). The resulting mixture was stirred at ambient for 15 mins. Water (50 ml) was added, the organic solution was washed with brine (30 ml), dried over anhydrous Na₂SO₄, concentrated under reduced pressure to give 1.28 g Compound 41e as a brown solid.

A mixture of Compound 41e (1.25 g, 3.89 mmol), iron power (4.34 g, 77.80 mmol), EtOH (50 ml), saturated aqueous solution of ammonium chloride (20 ml) was heated to 65° C. for 30 mins. After cooling the mixture was filtered, brine (20 ml) was added and the product was extracted with EA (50 ml×3). The combined organic phase was washed with brine (50 ml), dried over anhydrous Na₂SO₄, concentrated under reduced pressure to give 0.94 g Compound 41f as a brown solid.

A mixture of Compound 41f (508 mg, 1.74 mmol), Compound 40d (705 mg, 2.09 mmol), p-toluenesulfonic acid (449 mg, 2.61 mmol) and n-butyl alcohol (100 ml) was heated to 100° C. for 14 hours. The mixture was cooled and concentrated under reduced pressure, the residue was basified with aqueous solution of sodium carbonate (50 ml), extracted with EA (50 ml, 30 ml×2), the combined organic phase was washed with brine (50 ml×2), dried over anhydrous Na₂SO₄ and evaporated under reduced pressure, the residue was purified by column chromatography to give 198 mg Compound 41 as a yellow solid. MS: 593.2 (M+H)+. HNMR (DMSO-d6, 400 MHz): 11.36 (s, 1H), 11.05 (s, 1H), 8.89 (d, 1H), 8.60 (s, 1H), 8.25 (s, 1H), 7.92 (s, 1H), 7.61 (d, 1H), 7.54-7.56 (m, 1H), 7.49 (t, 1H), 7.14 (t, 1H), 7.04 (d, 1H), 6.02 (s, 1H), 5.54 (s, 1H), 3.77 (s, 3H), 3.55 (s, 4H), 3.24 (s, 2H), 2.99 (s, 3H), 2.88 (s, 3H), 2.35 (s, 4H).

Method 2

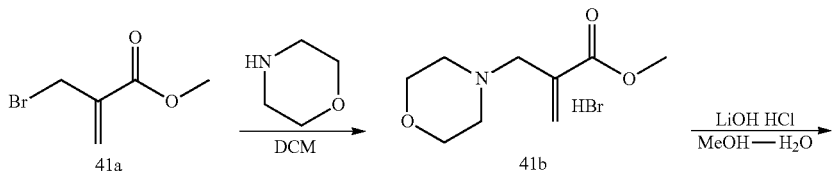

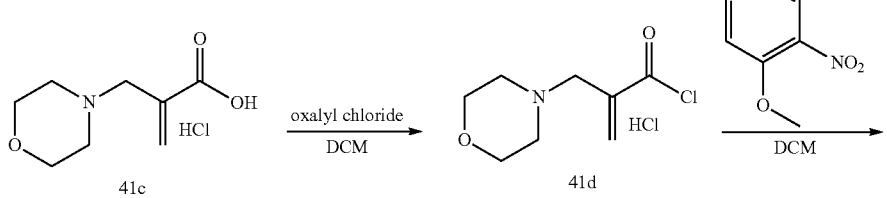

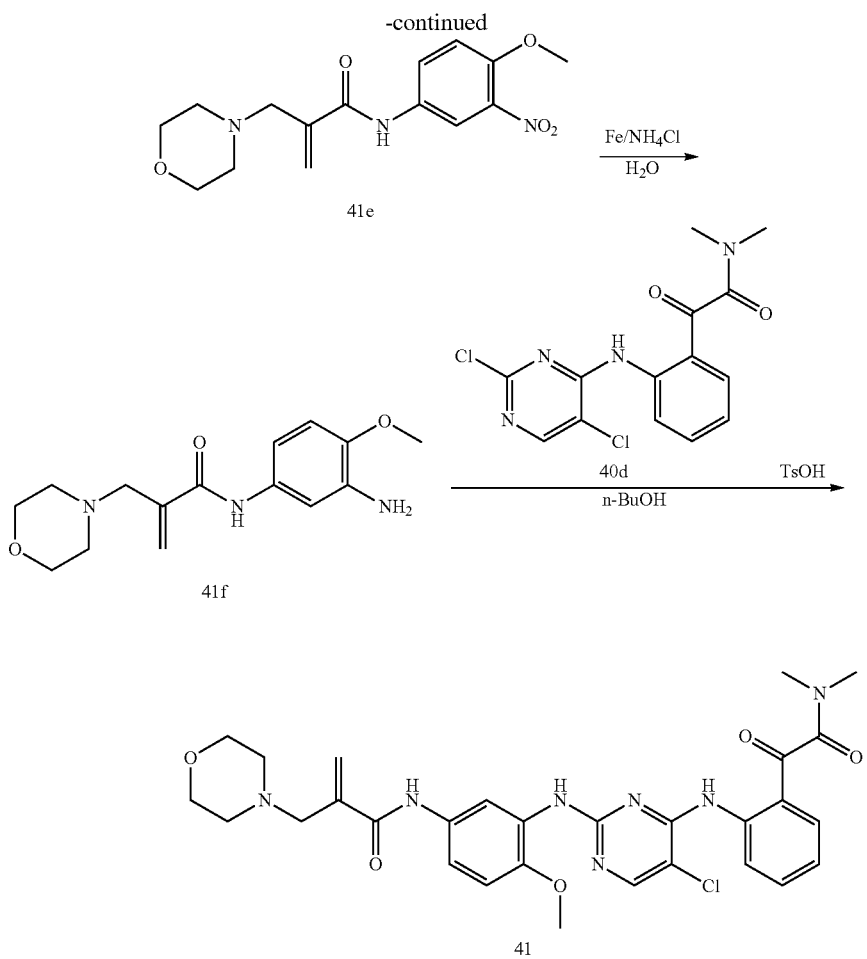

To a solution of Compound 41a (2.0 g) in DCM (25 ml) was added dropwise morpholine (0.6 g) in DCM (5 ml) at 0° C. with stirring. After that, the reaction mixture was stirred for another 3 hrs at 0-5° C. Then the reaction mixture was concentrated under reduced pressure to give 1.5 g Compound 41b as a white solid which was used for the next reaction directly.

A flask was charged with Compound 41b (1.45 g), LiOH (0.46 g), MeOH (10 ml) and water (5 ml). Then, the reaction mixture was stirred at room temperature for 1 hr. The reaction mixture was adjusted to PH=1-2 by con-HCl after most reaction solvent was removed under reduce pressure. And then, the appeared solid was filtered and the filter cake was dried to give 1.5 g Compound 41c.

A three-necked round bottom flask equipped with mechanical stirrer, addition funnel and thermometer was charged with Compound 41c (1.2 g) and DCM (25 ml). And then a solution of oxalyl chloride (1.1 g) in DCM (15 ml) was added dropwise (via addition funnel) at 0° C. while keeping inner temperature between 0-5° C. Then, the reaction mixture was warmed to 15° C. and then kept at 15° C. with stirring until the reaction was complete detected by TLC (DCM:MeOH=10:1). Reaction solvent was removed under reduce pressure to give 1.3 g Compound 41d used for the next reaction directly.

A three-necked round bottom flask equipped with mechanical stirrer, addition funnel and thermometer was charged with 4-methoxy-3-nitroaniline (0.8 g) and DCM (25 ml) and cooled to 0° C. After a solution of Compound 41d (1.3 g) in DCM (15 ml) was added dropwise (via addition funnel) while keeping inner temperature between 0-5° C. Then, the reaction mixture was stirred with warming naturally until the reaction was complete detected by TLC (DCM:MeOH=10:1) The reaction mixture was washed with water and organic phase was concentrated under reduced pressure to a residue, and then the residue was purified by column chromatography to give 0.8 g Compound 41e.

A three-necked round bottom flask equipped with mechanical stirrer and thermometer was charged with Compound 41e (98 mg), Fe (347 mg), and saturated aqueous solution of $NH_4Cl$ (15 ml). Then the reaction mixture was heated to 80° C. and stirred until the reaction was complete detected by TLC (DCM:MeOH=10:1). After, most reaction solvent was removed under reduce pressure to afford a residue. Then, the residue was partitioned between ethyl acetate (20 ml) and water (10 ml) 3 times and the combined organic phase was washed with brine and dried over $Na_2SO_4$ to give 62 mg Compound 41f.

Compound 40d (74 mg), Compound 41f (60 mg), TsOH (36 mg) and n-BuOH (15 ml) was stirred at 90° C. in sealed tube until the reaction was complete detected by TLC (DCM:MeOH=10:1). Then, the reaction mixture was washed with water and the organic phase was concentrated under reduced pressure. After that, the residue was purified by column chromatography to give 8 mg Compound 41 as a yellow solid. MS: 593.2 $(M+H)^+$.

| EX No | Chemical Name | Structure | Physical Data (MS) (M + H)+ |
|---|---|---|---|
| 42 | 1-(2-(2-(4-(4-acetylpiperazin-1-yl)-2-methoxyphenylamino)-5-chloropyrimidin-4-ylamino)phenyl)-2-morpholinoethane-1,2-dione | 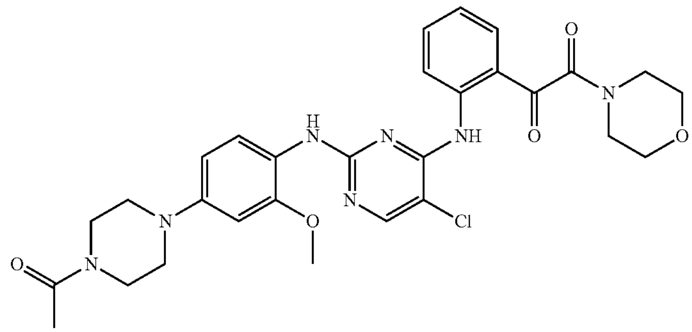 [SMILES: COc1cc(N2CCN(C(C)=O)CC2)ccc1Nc1ncc(Cl)c(Nc2ccccc2C(=O)C(=O)N2CCOCC2)n1] | 595.0 |
| 43 | 1-(2-(2-(2-methoxy-4-(4-methylpiperazin-1-yl)phenylamino)-5-(trifluoromethyl)pyrimidin-4-ylamino)phenyl)-2-morpholinoethane-1,2-dione | 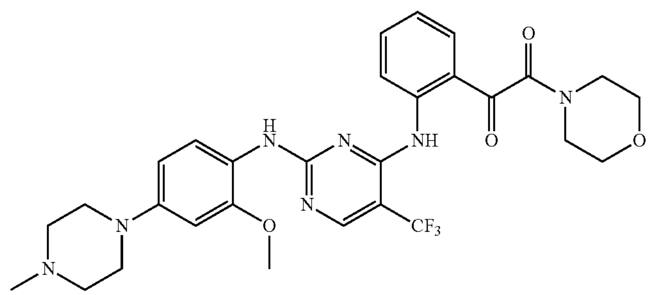 [SMILES: COc1cc(N2CCN(C)CC2)ccc1Nc1ncc(C(F)(F)F)c(Nc2ccccc2C(=O)C(=O)N2CCOCC2)n1] | 600.5 |
| 44 | 1-(2-(5-chloro-2-(2-methoxy-4-(4-methyl-piperazin-1-yl)phenylamino)pyrimidin-4-ylamino)phenyl)-2-morpholinoethane-1,2-dione | 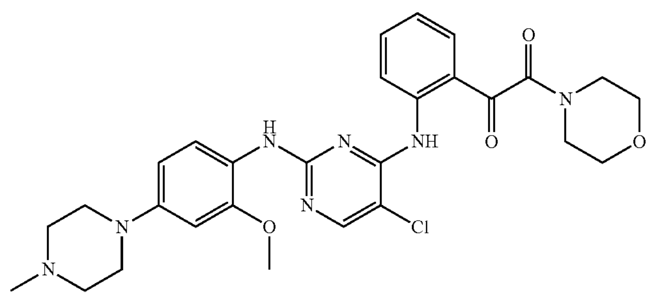 [SMILES: COc1cc(N2CCN(C)CC2)ccc1Nc1ncc(Cl)c(Nc2ccccc2C(=O)C(=O)N2CCOCC2)n1] | 567.0 |
| 45 | 1-(2-(2-(4-(4-(dimethylamino)piperidin-1-yl)-2-methoxyphenylamino)-5-(trifluoromethyl)pyrimidin-4-ylamino)phenyl)-2-morpholinoethane-1,2-dione | 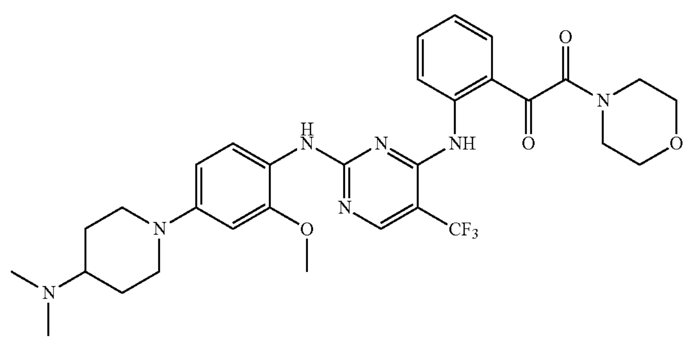 [SMILES: COc1cc(N2CCC(N(C)C)CC2)ccc1Nc1ncc(C(F)(F)F)c(Nc2ccccc2C(=O)C(=O)N2CCOCC2)n1] | 628.6 |
| 46 | 2-(2-(5-chloro-2-(2-methoxy-4-(4-methyl-piperazin-1-yl)phenylamino)pyrimidin-4-ylamino)phenyl)-N,N-dimethyl-2-oxo-acetamide | 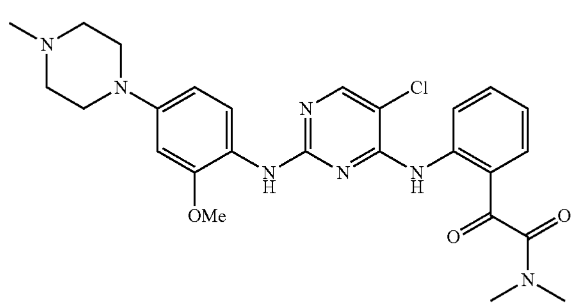 | 524.8 |

| EX No | Chemical Name | Structure | Physical Data (MS) (M + H)+ |
|---|---|---|---|
| 47 | 2-(2-(5-chloro-2-(2-methoxy-4-(4-methyl-piperazin-1-yl)phenylamino)pyrimidin-4-ylamino)phenyl)-N-methyl-2-oxo-acetamide | 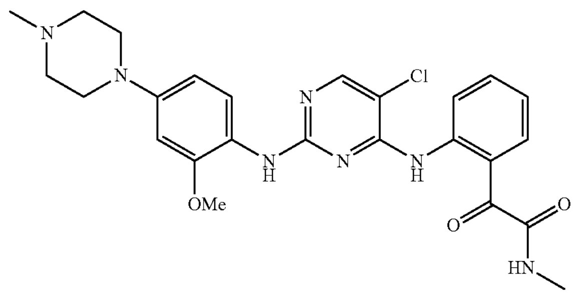 | 510.9 |
| 48 | 2-(2-(5-chloro-2-(2-methoxy-4-morpho-linophenylamino)pyrimidin-4-ylamino)phenyl)-N,N-dimethyl-2-oxoacetamide | 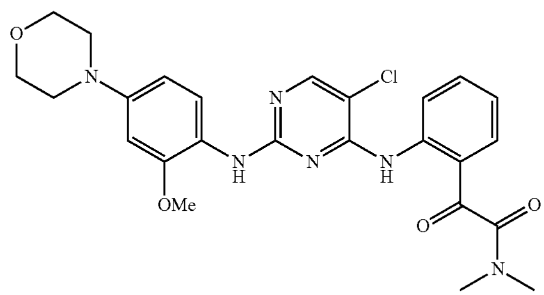 [SMILES: COc1cc(N2CCOCC2)ccc1Nc1ncc(Cl)c(Nc2ccccc2C(=O)C(=O)N(C)C)n1] | 511.8 |
| 49 | 2-(2-(5-chloro-2-(2-methoxy-4-(4-methyl-piperazin-1-yl)phenylamino)pyrimidin-4-ylamino)phenyl)-N-cyclopropyl-2-oxo-acetamide | 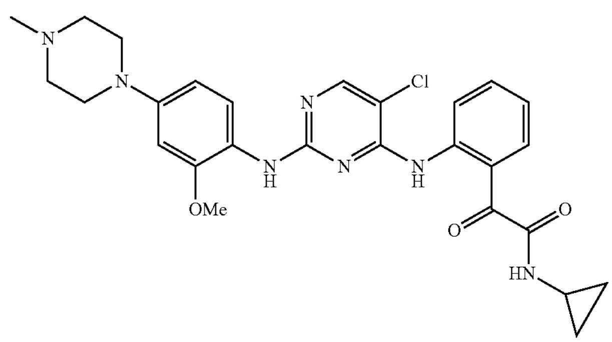 [SMILES: COc1cc(N2CCN(C)CC2)ccc1Nc1ncc(Cl)c(Nc2ccccc2C(=O)C(=O)NC2CC2)n1] | 536.9 |
| 50 | 2-(2-(2-(4-(4-acetylpiperazin-1-yl)-2-methoxyphenylamino)-5-chloropyrimidin-4-ylamino)phenyl)-N-cyclopropyl-2-oxo-acetamide | 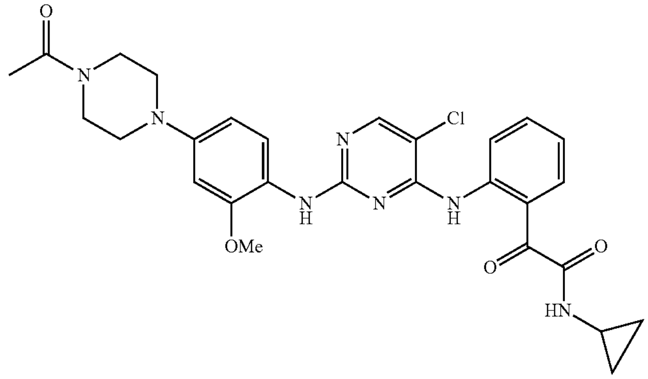 [SMILES: COc1cc(N2CCN(C(C)=O)CC2)ccc1Nc1ncc(Cl)c(Nc2ccccc2C(=O)C(=O)NC2CC2)n1] | 564.8 |

-continued

| EX No | Chemical Name | Structure | Physical Data (MS) (M + H)+ |
|---|---|---|---|
| 51 | 2-(2-(5-chloro-2-(2-methoxy-4-morpholinophenylamino)pyrimidin-4-ylamino)phenyl)-N-cyclopropyl-2-oxoacetamide | 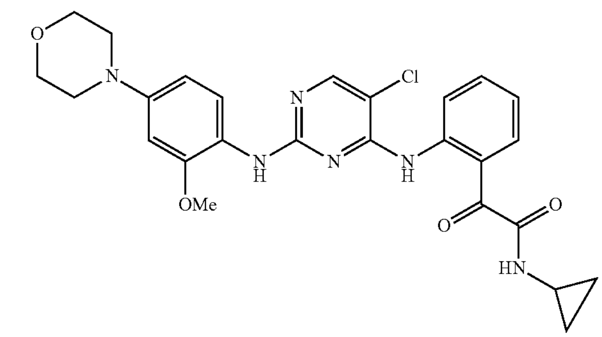 [SMILES: COc1cc(N2CCOCC2)ccc1Nc1ncc(Cl)c(Nc2ccccc2C(=O)C(=O)NC2CC2)n1] | 523.7 |
| 52 | 2-(2-(5-chloro-2-(2-methoxy-4-(4-propionylpiperazin-1-yl)phenylamino)pyrimidin-4-ylamino)phenyl)-N,N-dimethyl-2-oxoacetamide | 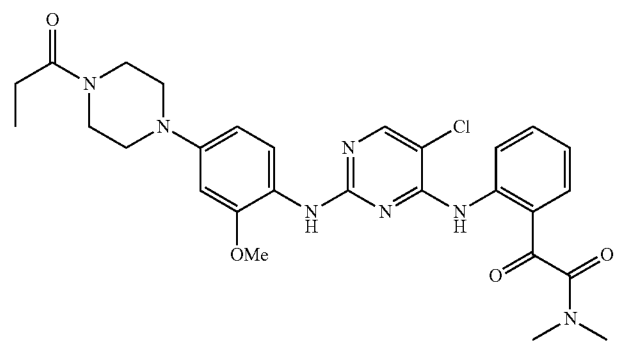 [SMILES: CCC(=O)N1CCN(c2ccc(Nc3ncc(Cl)c(Nc4ccccc4C(=O)C(=O)N(C)C)n3)c(OC)c2)CC1] | 567 |
| 53 | 2-(2-(2-(4-(4-acetylpiperazin-1-yl)-2-methoxyphenylamino)-5-chloropyrimidin-4-ylamino)phenyl)-N,N-dimethyl-2-oxoacetamide | 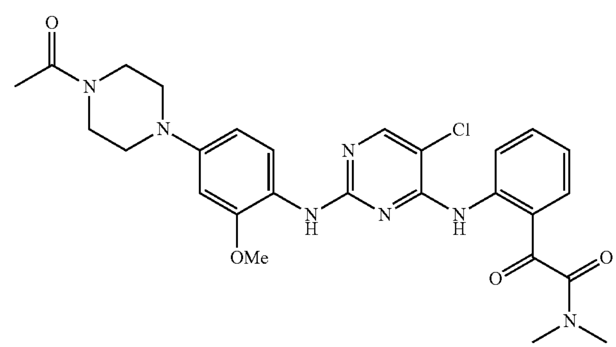 [SMILES: COc1cc(N2CCN(C(C)=O)CC2)ccc1Nc1ncc(Cl)c(Nc2ccccc2C(=O)C(=O)N(C)C)n1] | 552.8 |
| 54 | 2-(2-(5-chloro-2-(2-methoxy-4-(4-propionylpiperazin-1-yl)phenylamino)pyrimidin-4-ylamino)phenyl)-N-methyl-2-oxoacetamide | 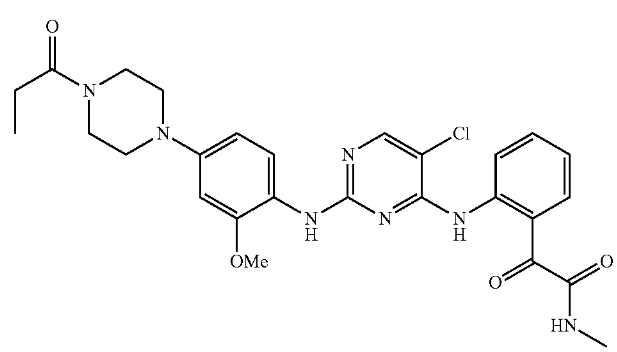 [SMILES: CCC(=O)N1CCN(c2ccc(Nc3ncc(Cl)c(Nc4ccccc4C(=O)C(=O)NC)n3)c(OC)c2)CC1] | 552.9 |

| EX No | Chemical Name | Structure | Physical Data (MS) (M + H)+ |
|---|---|---|---|
| 55 | N-(1-acryloylazetidin-3-yl)-2-(2-(5-chloro-2-(2-methoxy-4-(4-methylpiperazin-1-yl)phenylamino)pyrimidin-4-ylamino)phenyl)-2-oxoacetamide | 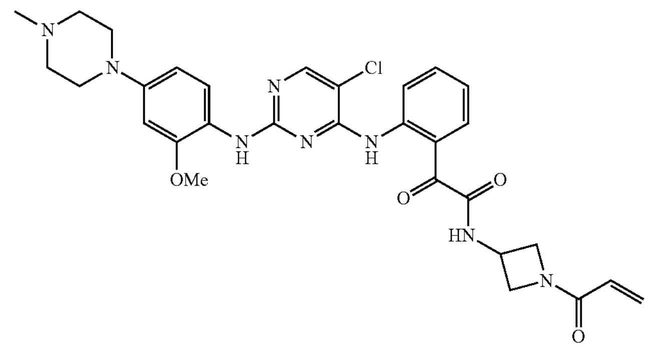 [SMILES: C=CC(=O)N1CC(NC(=O)C(=O)c2ccccc2Nc2nc(Nc3ccc(N4CCN(C)CC4)cc3OC)ncc2Cl)C1] | 606.1 |
| 56 | N-(1-acryloylpiperidin-4-yl)-2-(2-(5-chloro-2-(2-methoxy-4-(4-methylpiperazin-1-yl)phenylamino)pyrimidin-4-ylamino)phenyl)-2-oxoacetamide | 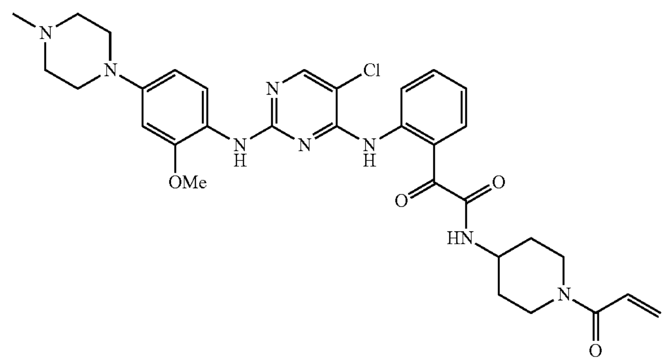 [SMILES: C=CC(=O)N1CCC(NC(=O)C(=O)c2ccccc2Nc2nc(Nc3ccc(N4CCN(C)CC4)cc3OC)ncc2Cl)CC1] | 634 |
| 57 | N-(3-(5-chloro-4-(2-(2-(methylamino)-2-oxoacetyl)phenylamino)pyrimidin-2-ylamino)phenyl)acrylamide | 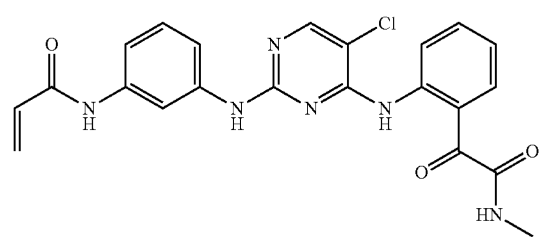 [SMILES: C=CC(=O)Nc1cccc(Nc2ncc(Cl)c(Nc3ccccc3C(=O)C(=O)NC)n2)c1] | 451.7 |
| 58 | N-(3-(4-(2-(2-amino-2-oxoacetyl)phenylamino)-5-(trifluoromethyl)pyrimidin-2-ylamino)phenyl)acrylamide | 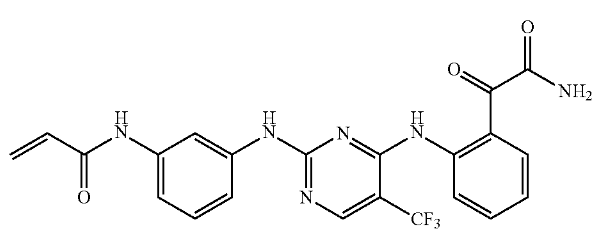 [SMILES: C=CC(=O)Nc1cccc(Nc2ncc(C(F)(F)F)c(Nc3ccccc3C(=O)C(N)=O)n2)c1] | 471.3 |
| 59 | N-(1-acryloylpiperidin-4-yl)-2-(2-(5-chloro-2-(4-fluoro-3-methoxyphenylamino)pyrimidin-4-ylamino)phenyl)-2-oxoacetamide | 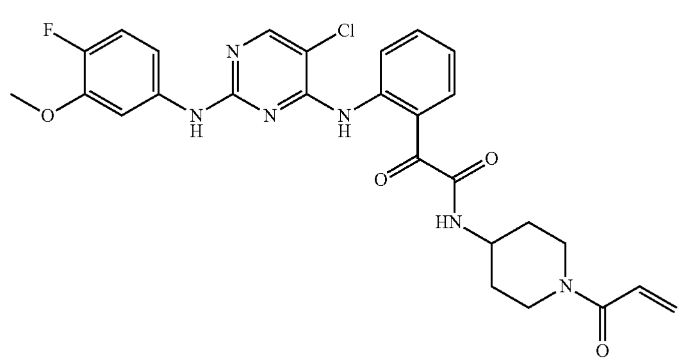 [SMILES: C=CC(=O)N1CCC(NC(=O)C(=O)c2ccccc2Nc2nc(Nc3ccc(F)c(OC)c3)ncc2Cl)CC1] | 553.9 |

| EX No | Chemical Name | Structure | Physical Data (MS) (M + H)+ |
|---|---|---|---|
| 60 | 2-(2-(5-chloro-2-(3-methoxy-4-(4-methyl-piperazin-1-yl)phenylamino)pyrimidin-4-ylamino)phenyl)-N-methyl-2-oxoacetamide | 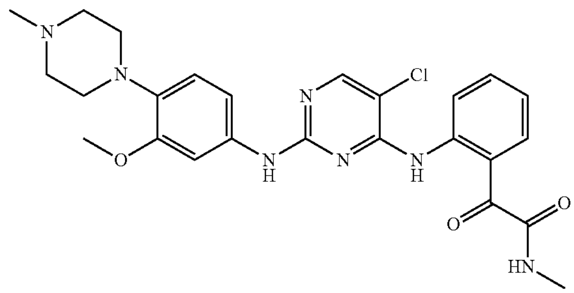 | 510.8 |
| 61 | 2-(2-(5-chloro-2-(3-methoxy-4-(4-methyl-piperazin-1-yl)phenylamino)pyrimidin-4-ylamino)phenyl)-N,N-dimethyl-2-oxoacetamide | 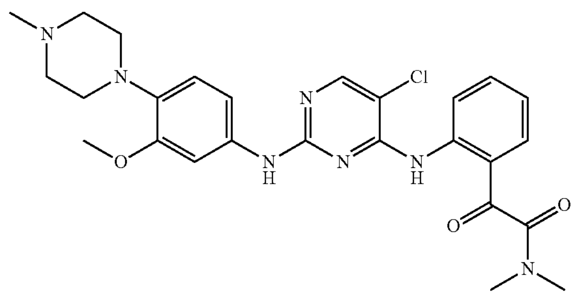 | 524.9 |
| 62 | 2-(2-(5-chloro-2-(4-fluoro-3-methoxy-phenylamino)pyrimidin-4-ylamino)phenyl)-N,N-dimethyl-2-oxoacetamide | 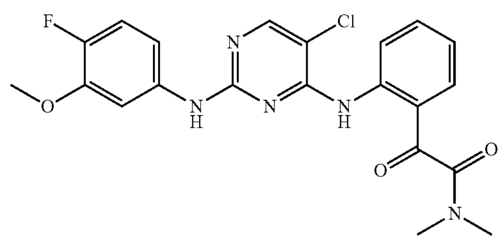 | 444.7 |
| 63 | 2-(2-(5-chloro-2-(4-fluoro-3-methoxy-phenylamino)pyrimidin-4-ylamino)phenyl)-N-methyl-2-oxoacetamide | 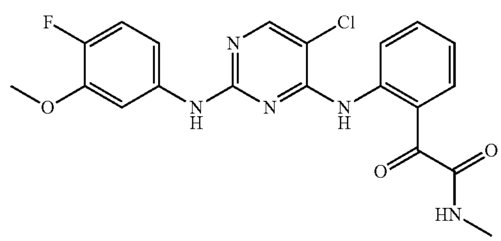 | 430.6 |
| 64 | N-(5-(5-chloro-4-(2-(2-(methylamino)-2-oxoacetyl)phenylamino)pyrimidin-2-ylamino)-2-methoxyphenyl)acrylamide | 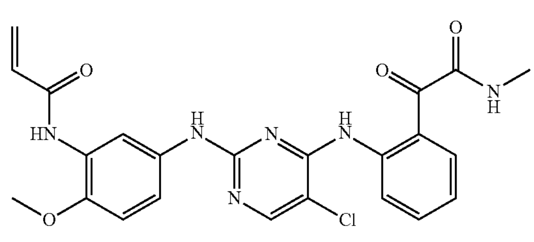 | 481.7 |
| 65 | N-(5-(5-chloro-4-(2-(2-(dimethylamino)-2-oxoacetyl)phenylamino)pyrimidin-2-ylamino)-2-methoxyphenyl)acrylamide | 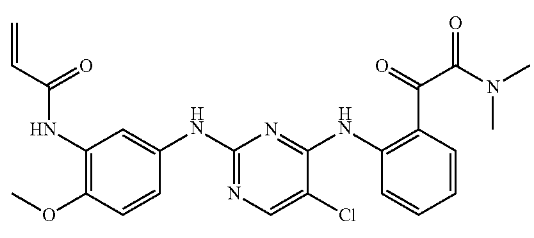 | 495.8 |

| EX No | Chemical Name | Structure | Physical Data (MS) (M + H)+ |
|---|---|---|---|
| 66 | N-(5-(5-chloro-4-(2-(2-(dimethylamino)-2-oxoacetyl)phenylamino)pyrimidin-2-ylamino)-2-fluoro-4-methoxyphenyl)acrylamide | 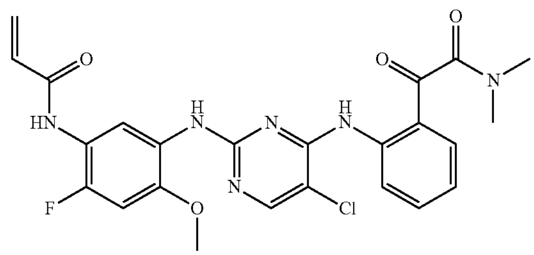 [SMILES: C=CC(=O)Nc1cc(Nc2ncc(Cl)c(Nc3ccccc3C(=O)C(=O)N(C)C)n2)c(OC)cc1F] | 513.9 |
| 67 | N-(3-(5-chloro-4-(2-(2-(dimethylamino)-2-oxoacetyl)phenylamino)pyrimidin-2-ylamino)-4-methoxyphenyl)acrylamide | 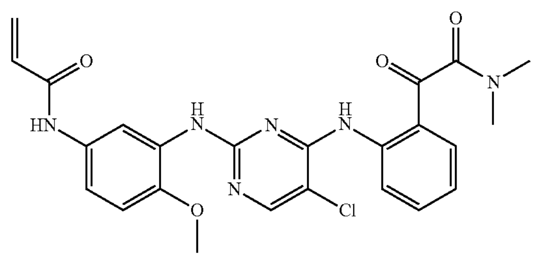 [SMILES: C=CC(=O)Nc1ccc(OC)c(Nc2ncc(Cl)c(Nc3ccccc3C(=O)C(=O)N(C)C)n2)c1] | 495.7 |
| 68 | N-(5-(5-chloro-4-(2-(2-(methylamino)-2-oxoacetyl)phenylamino)pyrimidin-2-ylamino)-4-fluoro-2-methoxyphenyl)acrylamide | 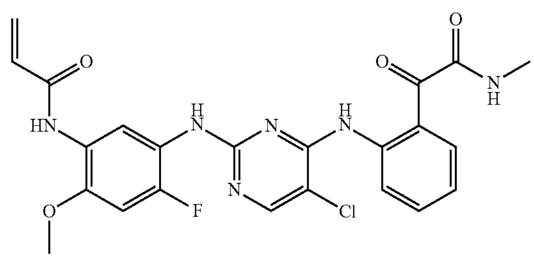 [SMILES: C=CC(=O)Nc1cc(Nc2ncc(Cl)c(Nc3ccccc3C(=O)C(=O)NC)n2)c(F)cc1OC] | 499.8 |
| 69 | N-(5-(5-chloro-4-(2-(2-(dimethylamino)-2-oxoacetyl)phenylamino)pyrimidin-2-ylamino)-4-fluoro-2-methoxyphenyl)acrylamide | 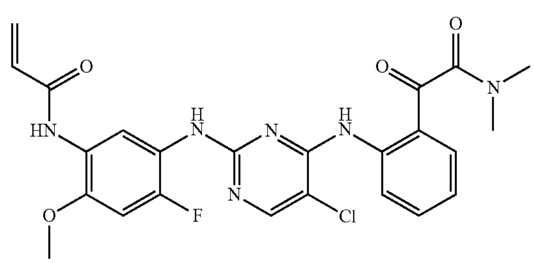 [SMILES: C=CC(=O)Nc1cc(Nc2ncc(Cl)c(Nc3ccccc3C(=O)C(=O)N(C)C)n2)c(F)cc1OC] | 513.8 |
| 70 | (E)-N-(3-(5-chloro-4-(2-(2-(dimethylamino)-2-oxoacetyl)phenylamino)pyrimidin-2-ylamino)-4-methoxyphenyl)but-2-enamide | 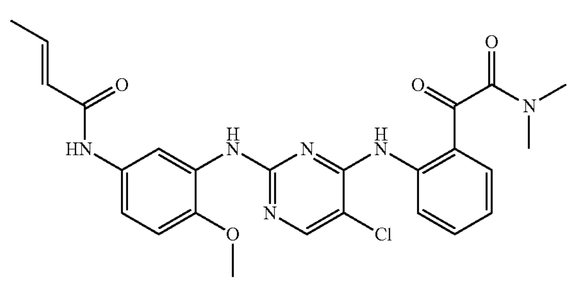 [SMILES: C/C=C/C(=O)Nc1ccc(OC)c(Nc2ncc(Cl)c(Nc3ccccc3C(=O)C(=O)N(C)C)n2)c1] | 509.9 |

| EX No | Chemical Name | Structure | Physical Data (MS) (M + H)+ |
|---|---|---|---|
| 71 | N-(3-(5-chloro-4-(2-(2-(dimethylamino)-2-oxoacetyl)phenylamino)pyrimidin-2-ylamino)-4-methoxyphenyl)-3-methylbut-2-enamide | 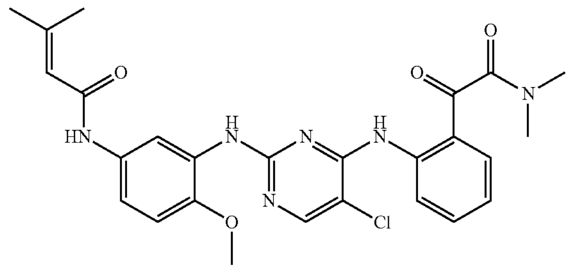 [SMILES: COc1ccc(NC(=O)C=C(C)C)cc1Nc1ncc(Cl)c(Nc2ccccc2C(=O)C(=O)N(C)C)n1] | 523.8 |
Example 72. Synthesis of Compound 72
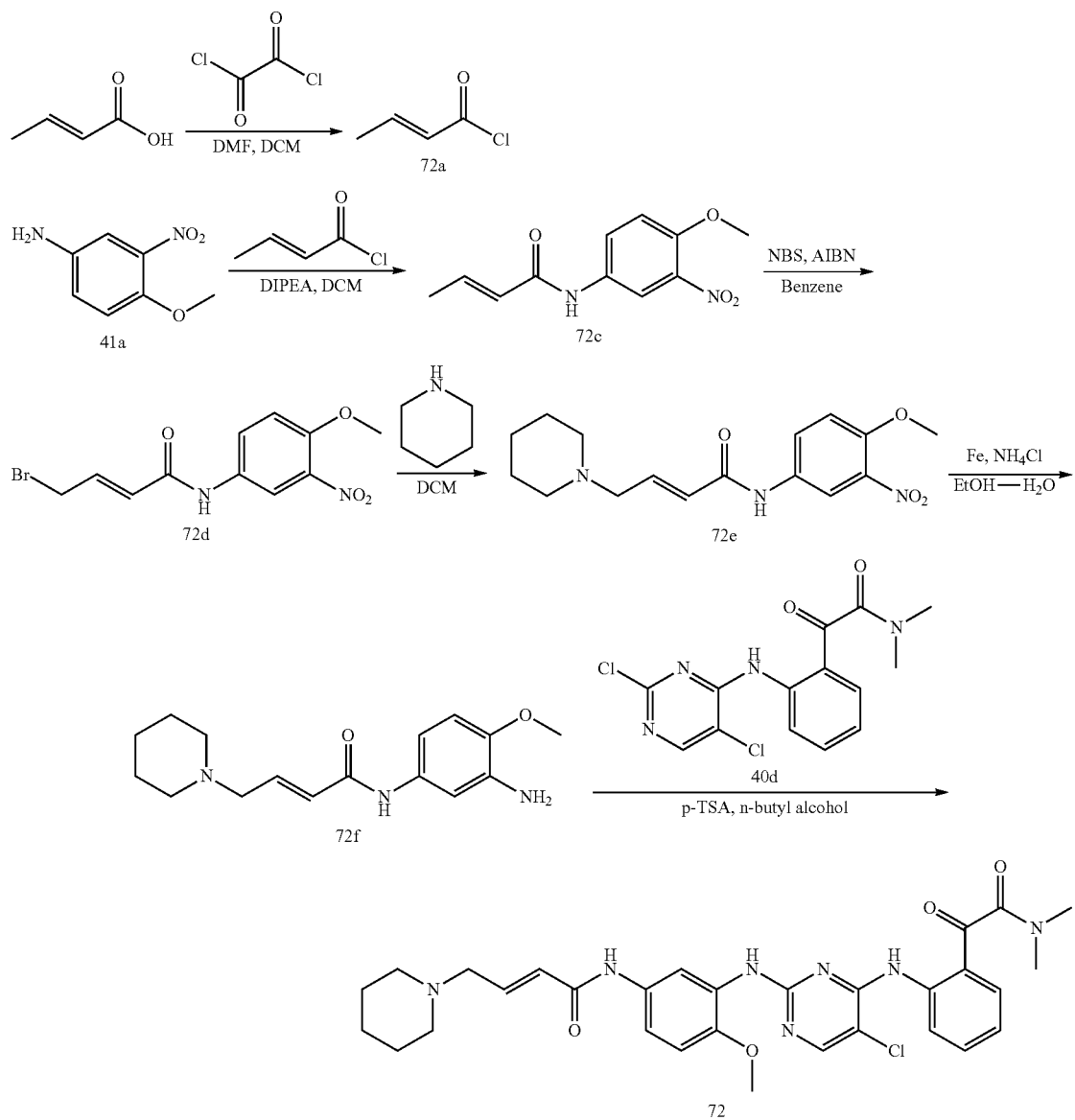

To a solution of crotonic acid (5.05 g, 58.65 mmol) and a drop of DMF in DCM (80 mL), was added oxalyl dichloride (11.12 g, 87.98 mmol) dropwise and the mixture was stirred at 15° C. for 30 min, then the solvent was concentrated under reduced pressure. The residue A (Compound 72a) was used for the next step without further purification.

To a solution of Compound 72b (4.92 g, 29.33 mmol) and DIPEA (3.80 g, 29.33 mmol) in DCM (100 mL) at 0° C., was A solution in DCM (30 mL) dropwise, and the resulting mixture was stirred at 0~5° C. for 30 min. Reaction was quenched with water (50 mL), the organic phase was concentrated under reduced pressure and the residue was purified by chromatography to give 4.21 g Compound 72c as a yellow solid.

A mixture of Compound 72c (402 mg, 1.72 mmol), NBS (334 mg, 1.88 mmol), AIBN (40 mg, 0.26 mmol) and benzene (70 mL) was heated to 80° C. for 5 hours. The mixture was concentrated under reduced pressure, and the residue of Compound 72d was used for the next step without further purification.

Compound 72d in DCM (30 mL) was added piperidine (1 mL), the resulting mixture was stirred at ambient temperature for 2 mins, evaporated to under reduced pressure, the residue was purified by chromatography to give 380 mg Compound 72e as a light yellow solid.

A mixture of Compound 72e (205 mg, 0.64 mmol), iron power (715 mg, 12.80 mmol) in EtOH (20 mL) and saturated aqueous solution of ammonium chloride (5 mL) was heated to 65° C. for 30 min. After cooled, water was added to filtrate and the product was extracted with EA (50 mL, 30 mL), the combined organic layers was washed with brine (30 mL), dried over anhydrous $Na_2SO_4$, concentrated under reduced pressure to give 108 mg Compound 72f as a brown solid.

A mixture of Compound 72f (105 mg, 0.36 mmol), Compound 40d (145 mg, 0.43 mmol), p-toluenesulfonic acid (93 mg, 0.54 mmol) in n-butyl alcohol (20 mL) was heated to 100° C. with stirring for 13 hours. The mixture was cooled and concentrated under reduced pressure, the residue was basified with aqueous solution of sodium carbonate (20 ml), extracted with EA (50 mL, 30 mL), the combined organic extracts was washed with brine (30 mL), dried over anhydrous sodium sulfate and evaporated under reduced pressure, the residue was purified by chromatography to give 38 mg Compound 72 as a yellow solid. MS: 591.2 $(M+H)^+$.

Example 74 Synthesis of Compound 74

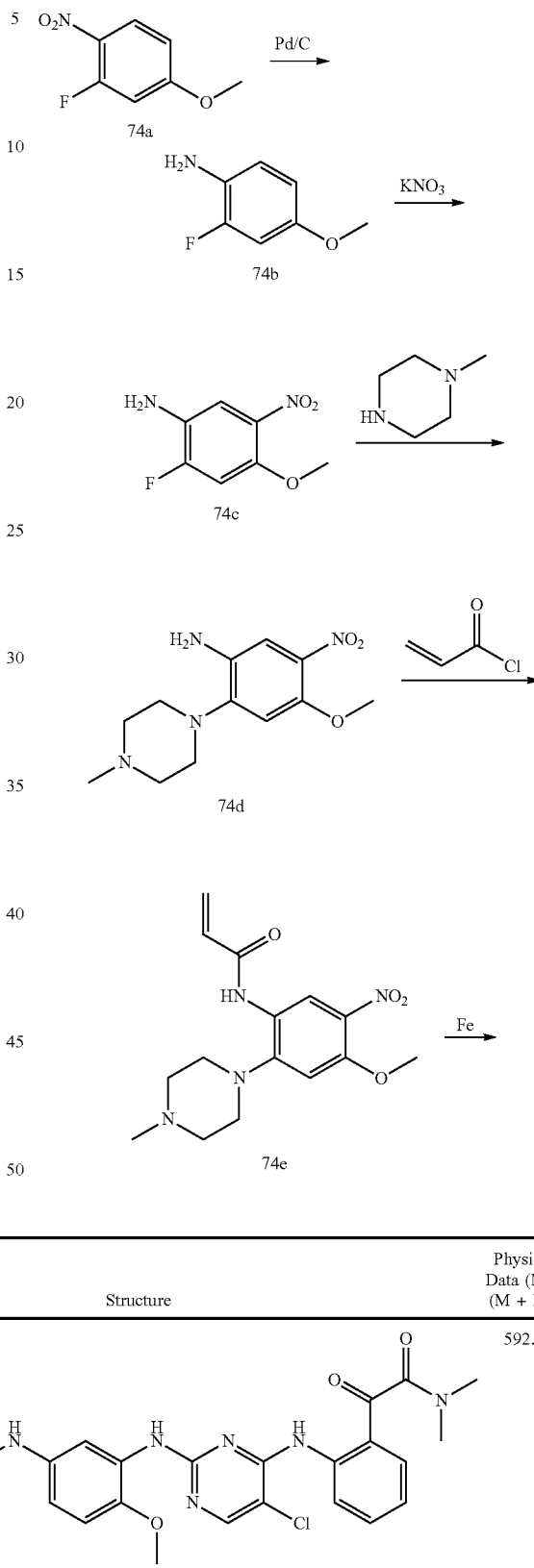

| EX No. | Chemical Name | Structure | Physical Data (MS) $(M + H)^+$ |
|---|---|---|---|
| 73 | N-(3-(5-chloro-4-(2-(2-(dimethylamino)-2-oxoacetyl)phenylamino)pyrimidin-2-ylamino)-4-methoxyphenyl)-2-(piperidin-1-ylmethyl)acrylamide | 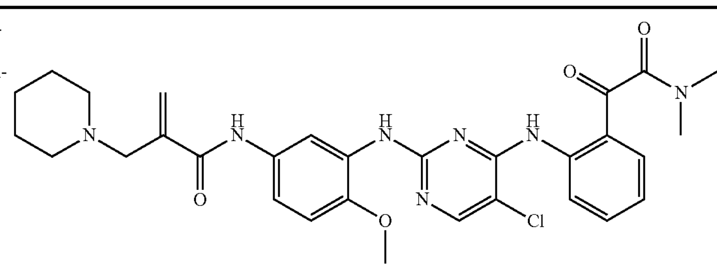 | 592.9 |

75

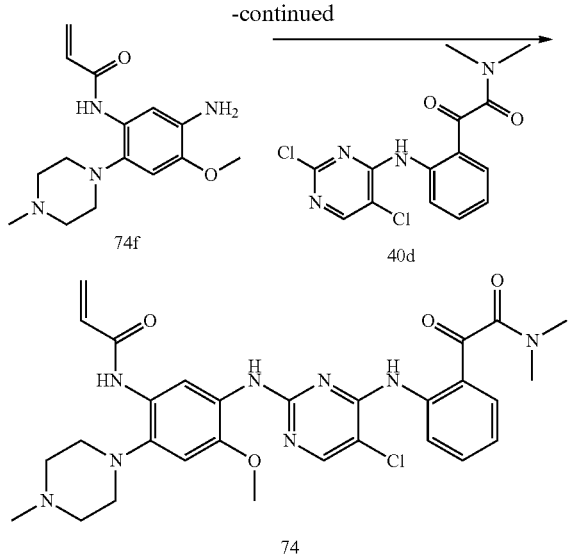

74f

40d

74

A solution of Compound 74a (50 g) and Pd/C (10 g) in MeOH (100 ml) under $H_2$ was stirred at room temperature for 4 hrs. After filtered, the filtrate was concentrated under reduced pressure to give 41 g Compound 74b.

To a solution of Compound 74b (8.05 g) dissolved in con.$H_2SO_4$ (40 ml), was added $KNO_3$ (5.77 g) with stirring for 2 hrs at ice bath. The reaction mixture was poured into NaOH solution, and the appeared solid was filtered to give 8.5 g Compound 74c as a yellow solid.

76

A mixture of Compound 74c (19.7 g), 1-methylpiperazine (15.9 g), and $K_2CO_3$ (21.94 g) in DMF was stirred at 80° C. for 8 hrs. Water was added to the reaction mixture and extracted with EA, the organic layer was washed with brine, dried over $Na_2SO_4$, concentrated under reduced pressure to give 10.2 g Compound 74d as a yellow solid.

To a solution of Compound 74d (1.02 g) and TEA (0.5 g) in DCM (20 ml), was added dropwise acryloyl chloride (0.38 g) at ice bath with stirring for 1 hr. The mixture was quenched with water and the organic layer was separated, after dried, it was concentrated under reduced pressure to give 0.98 g Compound 74e as a solid.

Compound 74e (0.98 g), iron powder (0.85 g) and $NH_4Cl$ (0.82 g) were dissolved in ethanol and water, then the mixture was stirred at 50° C. for 2 hrs. After filtered, the filtrated was extracted with EA, dried over $Na_2SO_4$, and concentrated under reduced pressure to give 0.58 g Compound 74f as a solid.

A mixture of Compound 74f (16.5 g), Compound 40d (23.2 g) and TsOH (11.75 g) in BuOH (250 ml) was stirred at 70° C. for 8 hrs. After the solvent was removed, the residue was purified by chromatography to give 11.3 g Compound 74 as a light yellow solid. MS: 592.2 $(M+H)^+$. HNMR (DMSO-d6, 400 MHz): 8.84-8.82 (d, J=7.76 Hz, 1H), 8.24 (s, 1H), 8.09-8.07 (d, J=6 Hz, 1H), 7.63-7.61 (d, J=8 Hz, 1H), 7.53 (s, 1H), 7.16-7.12 (t, J=7.6 Hz, 1H), 6.87 (s, 1H), 6.63-6.56 (dd, J=10 Hz, J=17.2 Hz, 1H), 6.18-6.13 (d, J=16.8 Hz, 1H), 5.71-5.68 (d, J=10.4 Hz, 1H), 3.77 (s, 3H), 3.00 (s, 3H), 2.89 (s, 6H), 2.55-2.50 (m, 5H), 2.25-2.25 (m, 3H).

| EX No. | Chemical Name | Structure | Physical Data (MS) $(M + H)^+$ |
|---|---|---|---|
| 75 | N-(5-(5-chloro-4-(2-(2-(methylamino)-2-oxoacetyl)phenylamino)pyrimidin-2-ylamino)-4-methoxy-2-(4-methylpiperazin-1-yl)phenyl)acrylamide | 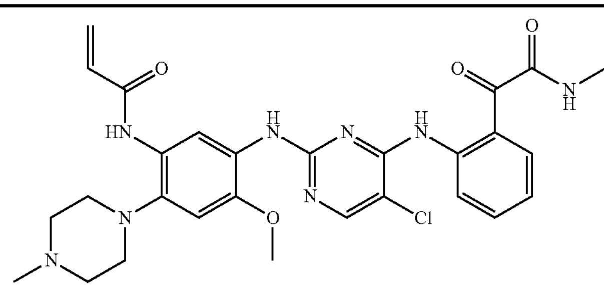 | 579.8 |
| 76 | N-(3-(5-chloro-4-(2-(2-(2-(dimethylamino)ethylamino)-2-oxoacetyl)phenylamino)pyrimidin-2-ylamino)phenyl)acrylamide | 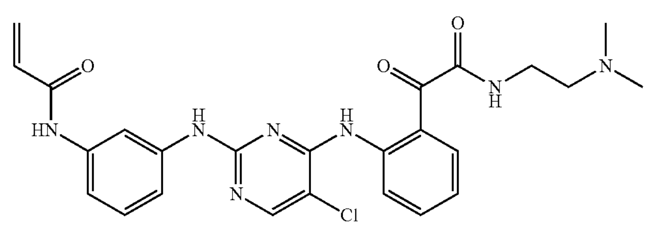 [SMILES: C=CC(=O)Nc1cccc(Nc2ncc(Cl)c(Nc3ccccc3C(=O)C(=O)NCCN(C)C)n2)c1] | 508.7 |
| 77 | N-(3-(5-chloro-4-(2-(2-(2-(dimethylamino)ethylamino)-2-oxoacetyl)phenylamino)pyrimidin-2-ylamino)-4-methoxyphenyl)acrylamide | 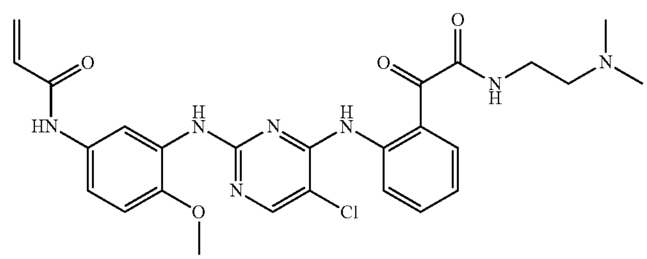 [SMILES: C=CC(=O)Nc1ccc(OC)c(Nc2ncc(Cl)c(Nc3ccccc3C(=O)C(=O)NCCN(C)C)n2)c1] | 538.9 |

| EX No. | Chemical Name | Structure | Physical Data (MS) (M + H)+ |
|---|---|---|---|
| 78 | N-(3-(5-chloro-4-(2-(2-(dimethylamino)-2-oxoacetyl)phenylamino)pyrimidin-2-ylamino)-4-methoxyphenyl)-2-((dimethylylamino)methyl)acrylamide | 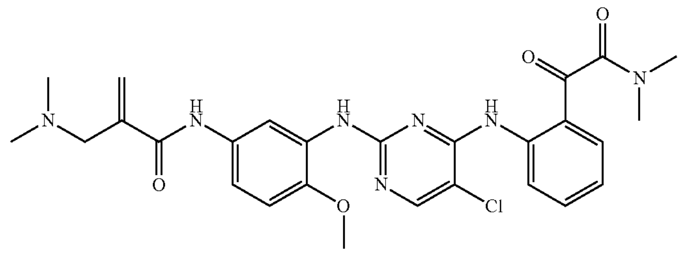 | 552.8 |
Example 79. Synthesis of Compound 79
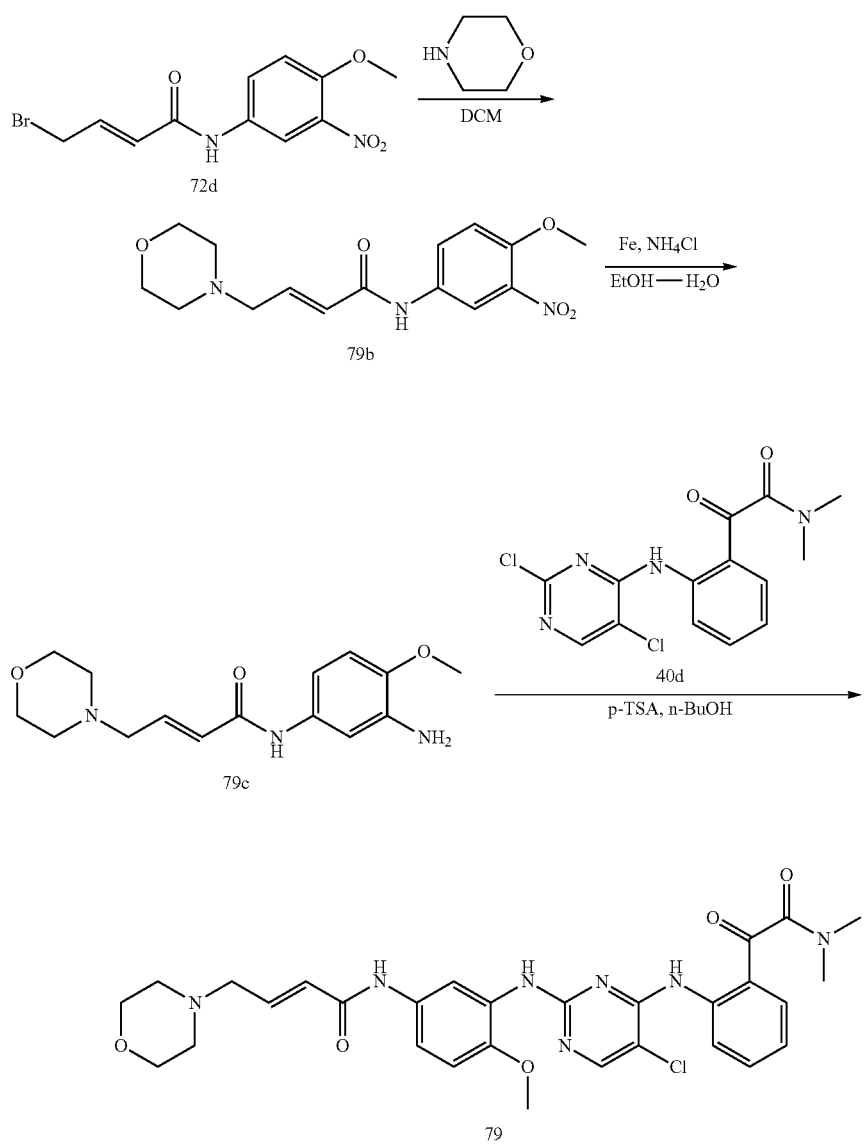

The mixture of Compound 72d (0.5 g) and DCM (50 ml) was added morpholine (1 ml), the resulting mixture was stirred at ambient temperature for 5 mins, evaporated to dryness, the residue was purified by chromatography to give 350 mg Compound 79b as a light yellow solid.

A mixture of Compound 79b (152 mg, 0.47 mmol), iron power (525 mg, 9.40 mmol), EtOH (20 ml) and saturated aqueous solution of ammonium chloride (10 ml) was heated to 65° C. for 15 mins. After cooling the mixture was filtered, brine (30 ml) was added and the product was extracted with EA (50 ml, 30 ml). The combined organic phase was washed with brine (30 ml), dried over anhydrous $Na_2SO_4$, concentrated under reduced pressure to give 102 mg Compound 79c as a brown solid.

A mixture of Compound 79c (102 mg, 0.34 mmol), Compound 40d (138 mg, 0.41 mmol), p-toluenesulfonic acid (87 mg, 0.51 mmol) and n-butyl alcohol (15 ml) was heated to 105° C. for 7 hrs. The mixture was cooled and concentrated in vacuo, the residue was basified with aqueous solution of sodium carbonate (20 ml), extracted with EA (50 ml, 30 ml), the combined organic phase was washed with brine (30 ml), dried over anhydrous $Na_2SO_4$ and evaporated to dryness, the residue was purified by chromatography to give 92 mg Compound 79 as a yellow solid. MS: 594.9 $(M+H)^+$. HNMR (DMSO-d6, 400 MHz): 11.35 (s, 1H), 9.93 (s, 1H), 8.85 (d, 1H), 8.61 (s, 1H), 8.28 (s, 1H), 7.93 (s, 1H), 7.63 (d, 1H), 7.48 (m, 2H), 7.13 (t, 1H), 7.04 (d, 1H), 6.65-6.68 (m, 1H), 6.24 (d, 1H), 3.77 (s, 3H), 3.59 (s, 4H), 3.11 (s, 2H), 3.01 (s, 3H), 2.90 (s, 3H), 2.38 (s, 4H).

| EX No. | Chemical Name | Structure | Physical Data (MS) $(M + H)^+$ |
|---|---|---|---|
| 80 | (E)-N-(3-(5-chloro-4-(2-(2-(dimethylamino)-2-oxoacetyl)phenylamino)pyrimidin-2-ylamino)-4-methoxyphenyl)-4-(dimethylamino)but-2-enamide | 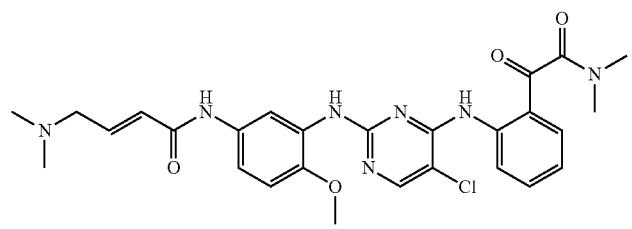 | 552.9 |
| 81 | N-(5-(5-chloro-4-(2-(2-(methylamino)-2-oxoacetyl)phenylamino)pyrimidin-2-ylamino)-2-(2-(dimethylamino)ethoxy)-4-methoxyphenyl)acrylamide | 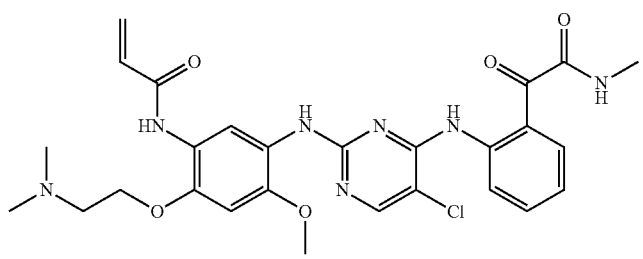 | 568.8 |
| 82 | N-(5-(5-chloro-4-(2-(2-(dimethylamino)-2-oxoacetyl)phenylamino)pyrimidin-2-ylamino)-2-(2-(dimethylamino)ethoxy)-4-methoxyphenyl)acrylamide | 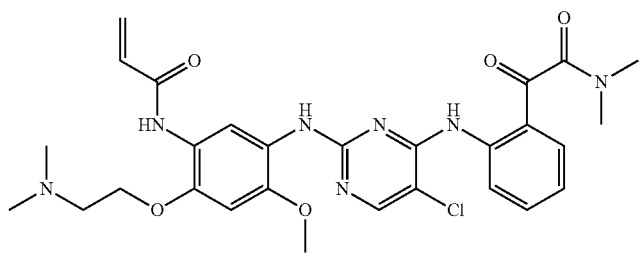 | 583.1 |
| 83 | N-(5-(5-chloro-4-(2-(2-(dimethylamino)-2-oxoacetyl)phenylamino)pyrimidin-2-ylamino)-4-methoxy-2-(3-morpholinopropoxy)phenyl)acrylamide | 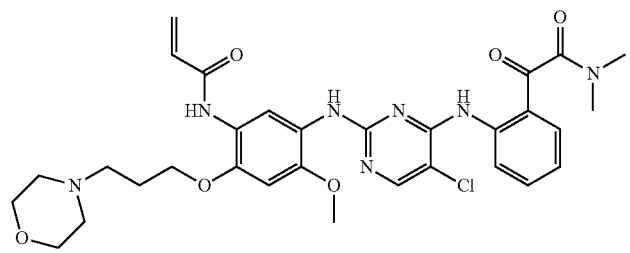 [SMILES: C=CC(=O)Nc1cc(Nc2ncc(Cl)c(Nc3ccccc3C(=O)C(=O)N(C)C)n2)c(OC)cc1OCCCN1CCOCC1] | 638.9 |

| EX No. | Chemical Name | Structure | Physical Data (MS) (M + H)+ |
|---|---|---|---|
| 84 | N-(5-(5-chloro-4-(2-(2-(methylamino)-2-oxoacetyl)phenylamino)pyrimidin-2-ylamino)-4-methoxy-2-(3-morpholinopropoxy)phenyl)acrylamide | 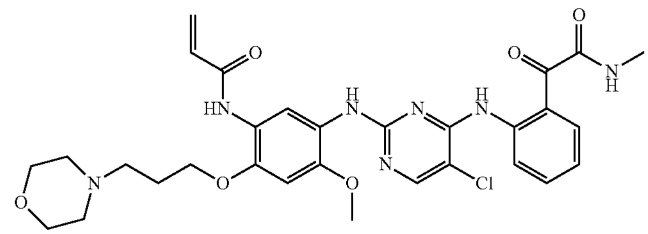 [SMILES: C=CC(=O)Nc1cc(Nc2ncc(Cl)c(Nc3ccccc3C(=O)C(=O)NC)n2)c(OC)cc1OCCCN1CCOCC1] | 625.0 |
| 85 | N-(3-(5-chloro-4-(2-(2-morpholino-2-oxoacetyl)phenylamino)pyrimidin-2-yl-amino)-4-methoxyphenyl)acrylamide | 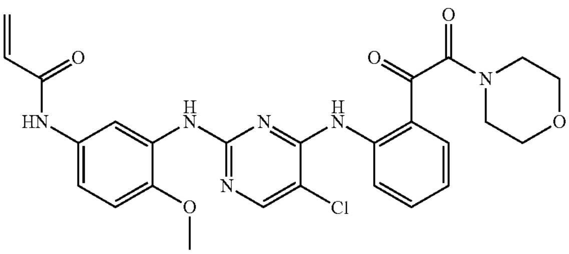 [SMILES: C=CC(=O)Nc1ccc(OC)c(Nc2ncc(Cl)c(Nc3ccccc3C(=O)C(=O)N3CCOCC3)n2)c1] | 537.9 |
| 86 | N-(5-(5-chloro-4-(2-(2-(2-(dimethylamino)ethylamino)-2-oxoacetyl)phenylamino)pyrimidin-2-ylamino)-2-methoxyphenyl)acrylamide | 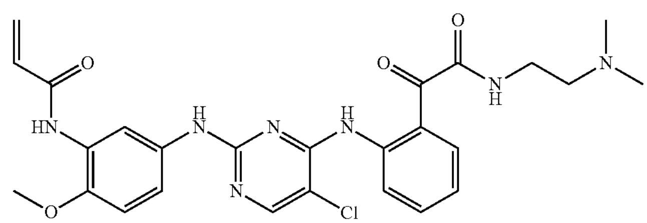 [SMILES: C=CC(=O)Nc1cc(Nc2ncc(Cl)c(Nc3ccccc3C(=O)C(=O)NCCN(C)C)n2)ccc1OC] | 538.8 |
| 87 | 2-(2-(2-(4-acryloyl-3,4-dihydro-2H-benzo[b][1,4]oxazin-6-ylamino)-5-chloropyrimidin-4-ylamino)phenyl)-N,N-dimethyl-2-oxoacetamide | 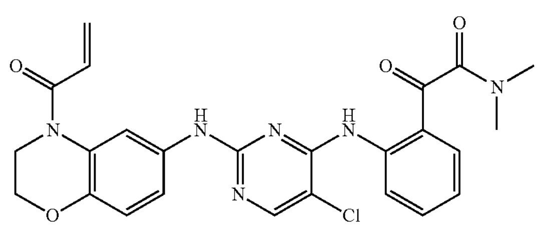 [SMILES: C=CC(=O)N1CCOc2ccc(Nc3ncc(Cl)c(Nc4ccccc4C(=O)C(=O)N(C)C)n3)cc21] | 506.1 |
| 88 | 2-(2-(2-(4-(4-acryloylpiperazin-1-yl)-2-methoxyphenylamino)-5-chloropyrimidin-4-ylamino)phenyl)-N,N-dimethyl-2-oxoacetamide | 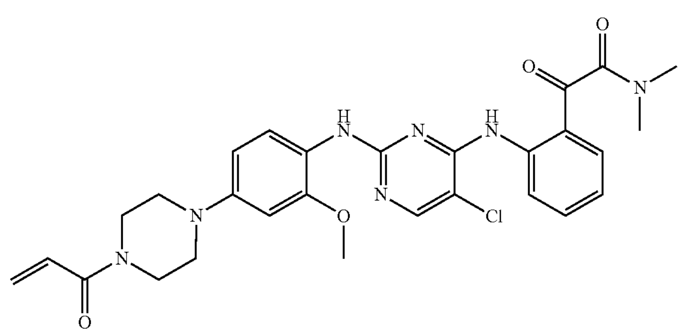 [SMILES: C=CC(=O)N1CCN(c2ccc(Nc3ncc(Cl)c(Nc4ccccc4C(=O)C(=O)N(C)C)n3)c(OC)c2)CC1] | 564.9 |
| 89 | N-(3-(5-chloro-4-(2-(2-(4-methylpiperazin-1-yl)-2-oxoacetyl)phenylamino)pyrimidin-2-ylamino)-4-methoxyphenyl)acrylamide | 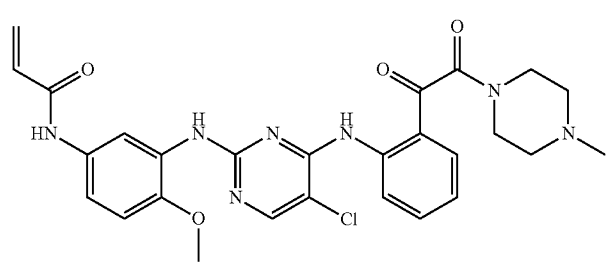 [SMILES: C=CC(=O)Nc1ccc(OC)c(Nc2ncc(Cl)c(Nc3ccccc3C(=O)C(=O)N3CCN(C)CC3)n2)c1] | 550.8 |

-continued

| EX No. Chemical Name | Structure | Physical Data (MS) (M + H)+ |
|---|---|---|
| 90 N-(3-(5-chloro-4-(2-(2-morpholino-2-oxoacetyl)phenylamino)pyrimidin-2-ylamino)phenyl)acrylamide | | 507.7 |
| 91 N-(3-(5-chloro-4-(2-(2-(4-methylpiperazin-1-yl)-2-oxoacetyl)phenylamino)pyrimidin-2-ylamino)phenyl)acrylamide | | 520.9 |
| 92 N-(5-(5-chloro-4-(2-(2-morpholino-2-oxoacetyl)phenylamino)pyrimidin-2-ylamino)-2-methoxyphenyl)acrylamide | | 537.8 |
| 93 N-(5-(5-chloro-4-(2-(2-(4-methylpiperazin-1-yl)-2-oxoacetyl)phenylamino)pyrimidin-2-ylamino)-2-methoxyphenyl)acrylamide | | 550.9 |
| 94 2-(2-(2-(4-(4-acetylpiperazin-1-yl)-3-methoxyphenylamino)-5-chloropyrimidin-4-ylamino)phenyl)-N,N-dimethyl-2-oxo-acetamide | | 551.2 |
| 95 2-(aziridin-1-ylmethyl)-N-(3-(5-chloro-4-(2-(2-(dimethylamino)-2-oxoacetyl)phenylamino)pyrimidin-2-ylamino)-4-methoxyphenyl)acrylamide | | 549.2 |

| EX No. | Chemical Name | Structure | Physical Data (MS) (M + H)+ |
|---|---|---|---|
| 96 | 2-(azetidin-1-ylmethyl)-N-(3-(5-chloro-4-(2-(2-(dimethylamino)-2-oxoacetyl)phenylamino)pyrimidin-2-ylamino)-4-methoxyphenyl)acrylamide | 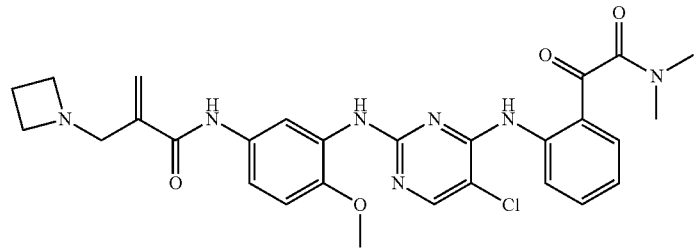 [SMILES: C=C(CN1CCC1)C(=O)Nc1ccc(OC)c(Nc2ncc(Cl)c(Nc3ccccc3C(=O)C(=O)N(C)C)n2)c1] | 563.2 |
| 97 | N-(3-(5-chloro-4-(2-(2-(dimethylamino)-2-oxoacetyl)phenylamino)pyrimidin-2-ylamino)-4-methoxyphenyl)-2-(pyrrolidin-1-ylmethyl)acrylamide | 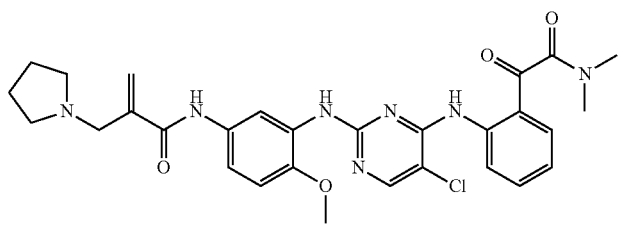 [SMILES: C=C(CN1CCCC1)C(=O)Nc1ccc(OC)c(Nc2ncc(Cl)c(Nc3ccccc3C(=O)C(=O)N(C)C)n2)c1] | 577.2 |
| 98 | N-(5-(5-chloro-4-(2-(2-(dimethylamino)-2-oxoacetyl)phenylamino)pyrimidin-2-ylamino)-4-methoxy-2-(2-morpholinoethoxy)phenyl)acrylamide | 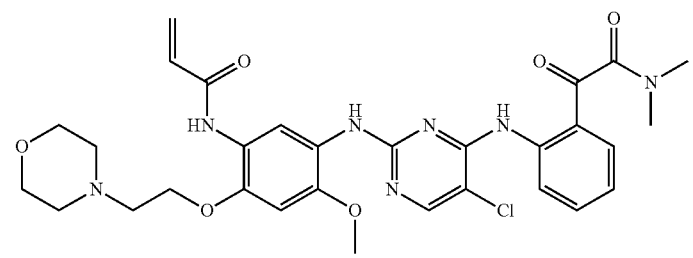 [SMILES: C=CC(=O)Nc1cc(Nc2ncc(Cl)c(Nc3ccccc3C(=O)C(=O)N(C)C)n2)c(OC)cc1OCCN1CCOCC1] | 623.2 |
| 99 | N-(5-(5-chloro-4-(2-(2-(dimethylamino)-2-oxoacetyl)phenylamino)pyrimidin-2-ylamino)-2-((2-(dimethylamino)ethyl)(methyl)amino)phenyl)acrylamide | 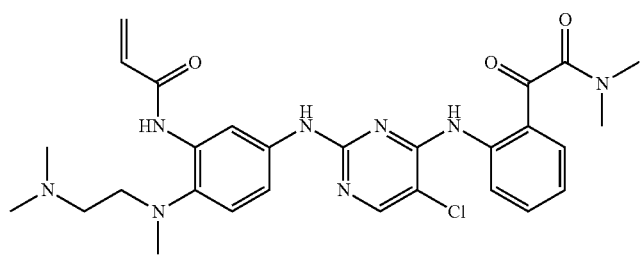 | 564.2 |
| 100 | N-(3-(4-(2-(2-(dimethylamino)-2-oxoacetyl)phenylamino)-5-methylpyrimidin-2-ylamino)-4-methoxyphenyl)-2-((dimethylamino)methyl)acrylamide | 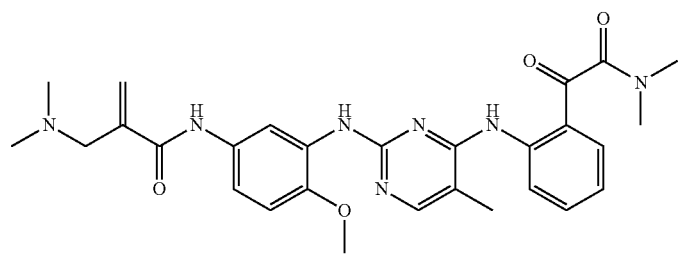 | 531.3 |
| 101 | N-(5-(4-(2-(2-(dimethylamino)-2-oxoacetyl)phenylamino)-5-methylpyrimidin-2-ylamino)-2-methoxyphenyl)acrylamide | 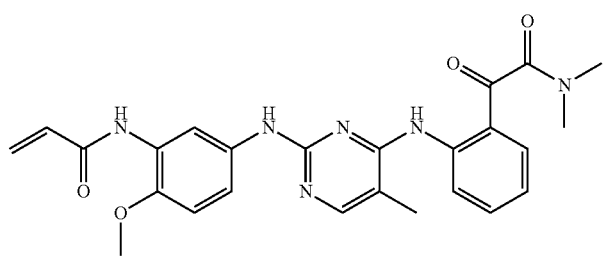 [SMILES: C=CC(=O)Nc1cc(Nc2ncc(C)c(Nc3ccccc3C(=O)C(=O)N(C)C)n2)ccc1OC] | 474.2 |

-continued

| EX No. Chemical Name | Structure | Physical Data (MS) (M + H)+ |
|---|---|---|
| 102 N-(5-(5-chloro-4-(2-(2-((2-(dimethylamino)ethyl)(methyl)amino)-2-oxoacetyl)phenylamino)pyrimidin-2-ylamino)-2-methoxyphenyl)acrylamide | 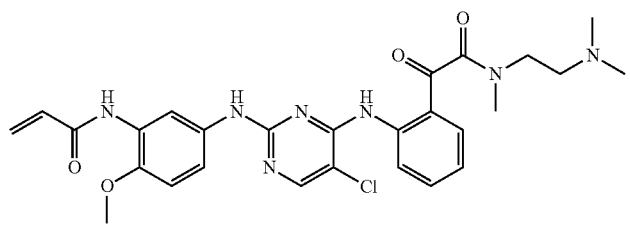 [SMILES: C=CC(=O)Nc1cc(Nc2ncc(Cl)c(Nc3ccccc3C(=O)C(=O)N(C)CCN(C)C)n2)ccc1OC] | 551.2 |
| 103 N-(5-(5-chloro-4-(2-(2-(dimethylamino)-2-oxoacetyl)phenylamino)pyrimidin-2-ylamino)-2-(2-(dimethylamino)ethoxy)phenyl)-3-methoxypropanamide | 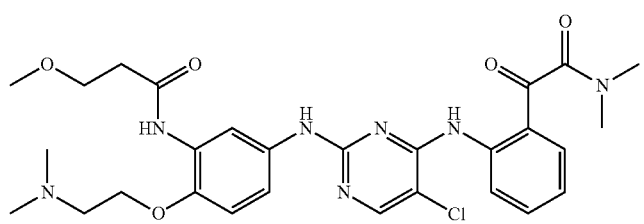 | 583.2 |
| 104 N-(5-(5-chloro-4-(2-(2-(dimethylamino)-2-oxoacetyl)phenylamino)pyrimidin-2-ylamino)-2-cyclopropoxyphenyl)acrylamide | 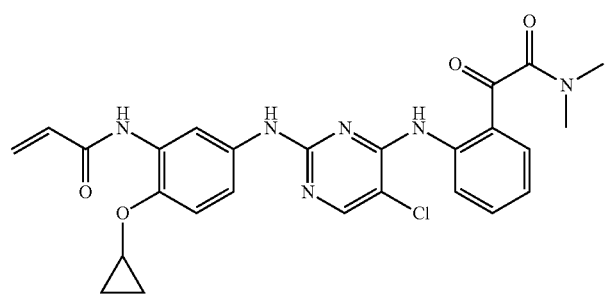 | 520.2 |
| 105 N-(5-(5-chloro-4-(2-(2-(dimethylamino)-2-oxoacetyl)phenylamino)pyrimidin-2-ylamino)-2-(cyclopentyloxy)phenyl)acrylamide | 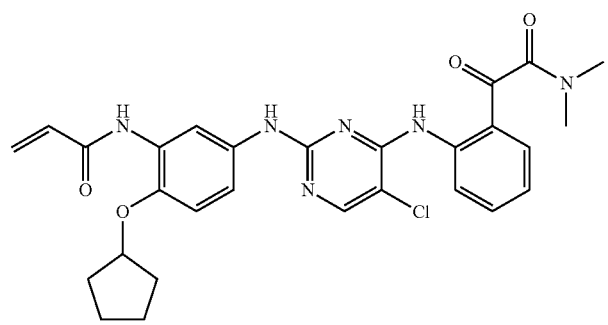 | 548.2 |
| 106 N-(5-(5-chloro-4-(2-(2-(dimethylamino)-2-oxoacetyl)phenylamino)pyrimidin-2-ylamino)-2-(1-methylpyrrolidin-3-yloxy)phenyl)acrylamide | 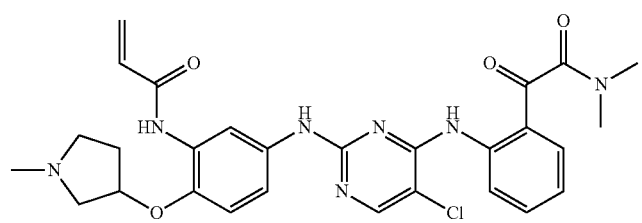 | 563.2 |
| 107 N-(5-(5-chloro-4-(2-(2-(dimethylamino)-2-oxoacetyl)phenylamino)pyrimidin-2-ylamino)-2-(4-(dimethylamino)cyclohexyloxy)phenyl)acrylamide | 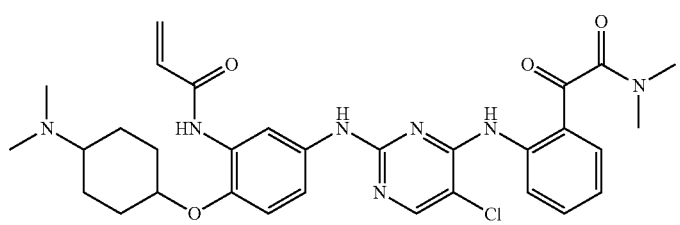 | 605.3 |

-continued

| EX No. | Chemical Name | Structure | Physical Data (MS) (M + H)+ |
|---|---|---|---|
| 108 | N-(2-(azetidin-3-yloxy)-5-(5-chloro-4-(2-(2-(dimethylamino)-2-oxoacetyl)phenylamino)pyrimidin-2-ylamino)phenyl)acrylamide | 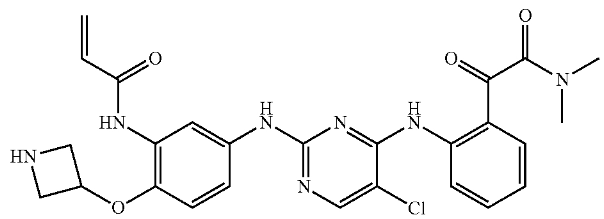 [SMILES: C=CC(=O)Nc1cc(Nc2ncc(Cl)c(Nc3ccccc3C(=O)C(=O)N(C)C)n2)ccc1OC1CNC1] | 535.2 |
| 109 | N-(5-(5-chloro-4-(2-(2-(dimethylamino)-2-oxoacetyl)phenylamino)pyrimidin-2-ylamino)-2-(1-methylazetidin-3-yloxy)phenyl)acrylamide | 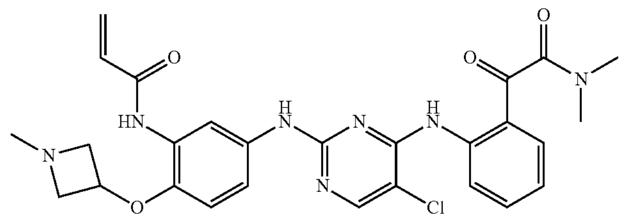 | 549.2 |
| 110 | N-(5-(5-chloro-4-(2-(2-(dimethylamino)-2-oxoacetyl)phenylamino)pyrimidin-2-ylamino)-2-morpholinophenyl)acrylamide | 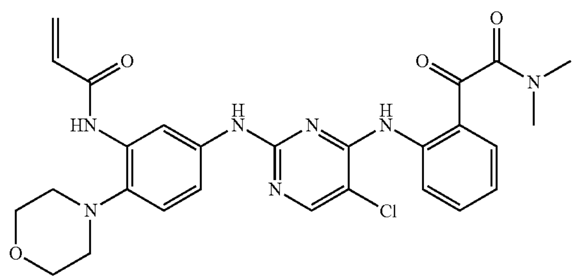 [SMILES: C=CC(=O)Nc1cc(Nc2ncc(Cl)c(Nc3ccccc3C(=O)C(=O)N(C)C)n2)ccc1N1CCOCC1] | 549.2 |
| 111 | N-(5-(5-chloro-4-(2-(2-(dimethylamino)-2-oxoacetyl)phenylamino)pyrimidin-2-ylamino)-2-(4-methylpiperazin-1-yl)phenyl)acrylamide | 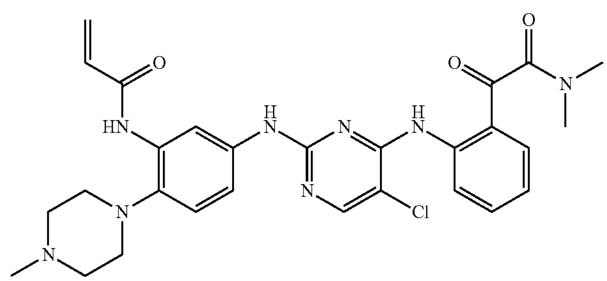 | 562.2 |
| 112 | N-(3-(5-chloro-4-(2-(2-(dimethylamino)-2-oxoacetyl)phenylamino)pyrimidin-2-ylamino)phenyl)-2-(morpholinomethyl)acrylamide | 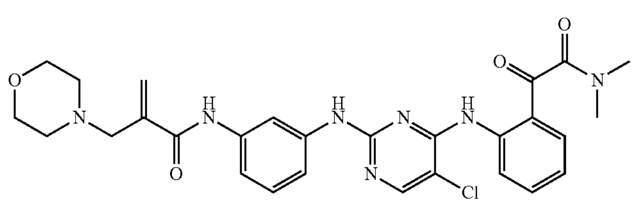 [SMILES: C=C(CN1CCOCC1)C(=O)Nc1cccc(Nc2ncc(Cl)c(Nc3ccccc3C(=O)C(=O)N(C)C)n2)c1] | 563.2 |
| 113 | N-(3-(5-chloro-4-(2-(2-(dimethylamino)-2-oxoacetyl)phenylamino)pyrimidin-2-ylamino)phenyl)-2-(piperidin-1-ylmethyl)acrylamide | 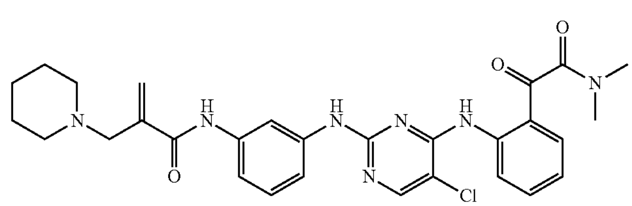 [SMILES: C=C(CN1CCCCC1)C(=O)Nc1cccc(Nc2ncc(Cl)c(Nc3ccccc3C(=O)C(=O)N(C)C)n2)c1] | 561.2 |

| EX No. | Chemical Name | Structure | Physical Data (MS) (M + H)+ |
|---|---|---|---|
| 114 | (E)-N-(3-(5-chloro-4-(2-(2-(dimethylamino)-2-oxoacetyl)phenylamino)pyrimidin-2-ylamino)phenyl)-4-(dimethylamino)but-2-enamide | 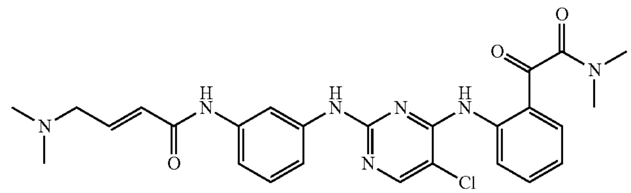 | 521.2 |

Example 115. Synthesis of Compound 115

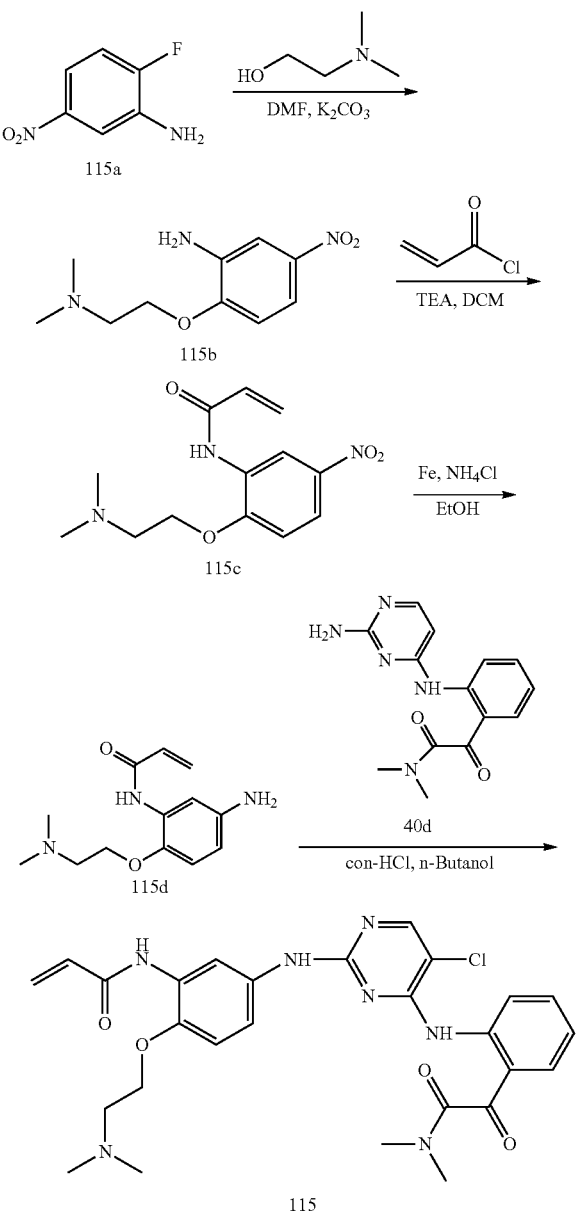

To a stirred solution of N,N-dimethylethanolamine (8.58 g, 96 mmol) in DMF (80 ml) at 0° C., NaH (1.54 g, 64 mmol) was added slowly. After the mixture was stirred at 0-5° C. for 30 minutes, Compound 115a (5.01 g, 32 mmol) in DMF was added dropwise. Then the reaction mixture was stirred with warming naturally to the room temperature for 4 hours. The reaction was complete detected by TLC (PE: EA=1:1). Then water (80 ml) was added to the solution to quench the overdose NaH. Afterwards, the mixture was extracted with ethyl acetate (80 ml×2). The combined organic phase was washed with brine (80 ml) and dried over sodium sulfate and concentrated under reduced pressure to give 6.49 g Compound 115b.

To a stirred solution of Compound 115b (6.49 g, 28.81 mmol) and triethylamine (4.8 ml, 34.58 mmol) in DCM (55 ml) at 0° C., a solution of acryloyl chloride (2.3 ml, 31.68 mmol) in DCM (10 ml) was added dropwise. The reaction mixture was stirred at 0° C. for 30 mins and then the reaction solution was washed with water (60 ml) and the organic phase was concentrated under reduced pressure to give 7.32 g Compound 115c.

A mixture of Compound 115c (7.32 g, 25.93 mmol) in ethanol (15 ml), iron powder (8.84 g, 155.57 mmol) and ammonium chloride (2.77 g, 51.86 mmol) in water (70 ml) was heated to 90° C. for 30 mins. Then the reaction solution was filtered and the filtrate was extracted with ethyl acetate (80 ml×2) and the combined organic phase was washed with brine (80 ml) and dried over sodium sulfate and concentrated under reduced pressure to give 2.31 g Compound 115d.

A mixture of Compound 115d (2.30 g, 9.23 mmol), Compound 40d (3.13 g, 9.23 mmol) and hydrochloric acid (0.3 ml) in n-Butanol (30 ml) was heated to 110° C. for 6 hours. The progress was monitored by TLC (DCM: MeOH=10:1). Then the reaction mixture was cooled to room temperature and concentrated under reduced pressure to afford crude compound. The crude product was purified by column chromatography to give 1.71 g Compound 115 as a yellow solid. MS: 551.2 (M+H)+. H-NMR (DMSO-d6, 400 MHz): 8.35 (s, 1H), 8.29 (s, 1H), 7.88-7.82 (m, 1H), 7.47 (s, 1H), 7.32-7.15 (m, 4H), 7.05-7.02 (m, 1H), 6.25-6.21 (m, 1H), 5.70-5.67 (m, 1H), 4.33-4.32 (t, 3H), 3.60-3.55 (t, 3H), 3.00 (s, 6H), 2.90 (s, 6H).

| EX No. | Chemical Name | Structure | Physical Data (MS) (M + H)+ |
|---|---|---|---|
| 116 | N-(5-(5-chloro-4-(2-(2-(dimethylamino)-2-oxoacetyl)phenylamino)pyrimidin-2-ylamino)-2-(difluoromethoxy)phenyl)acrylamide | 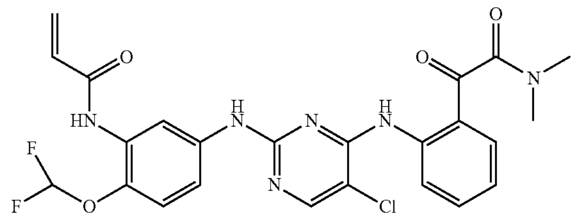 [SMILES: C=CC(=O)Nc1cc(Nc2ncc(Cl)c(Nc3ccccc3C(=O)C(=O)N(C)C)n2)ccc1OC(F)F] | 530.1 |
| 117 | 2-(2-(5-chloro-2-(3-methoxy-4-morpholinophenylamino)pyrimidin-4-ylamino)phenyl)-N,N-dimethyl-2-oxoacetamide | 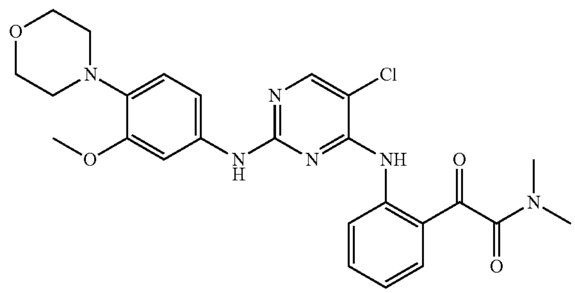 [SMILES: COc1cc(Nc2ncc(Cl)c(Nc3ccccc3C(=O)C(=O)N(C)C)n2)ccc1N1CCOCC1] | 510.2 |
| 118 | 2-(2-(5-chloro-2-(4-(4-(dimethylamino)piperidin-1-yl)-3-methoxyphenylamino)pyrimidin-4-ylamino)phenyl)-N,N-dimethyl-2-oxoacetamide | 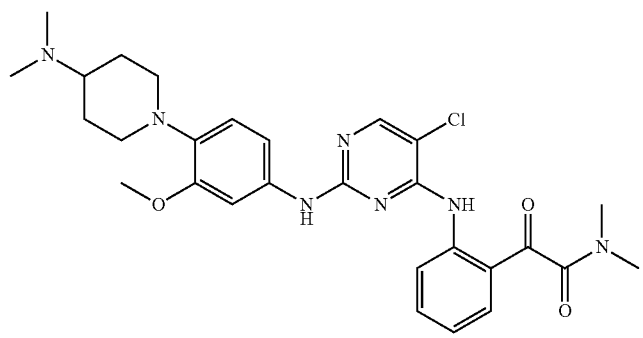 | 551.2 |
| 119 | 2-(2-(5-chloro-2-(4-(4-methylpiperazin-1-yl)phenylamino)pyrimidin-4-ylamino)phenyl)-N,N-dimethyl-2-oxoacetamide | 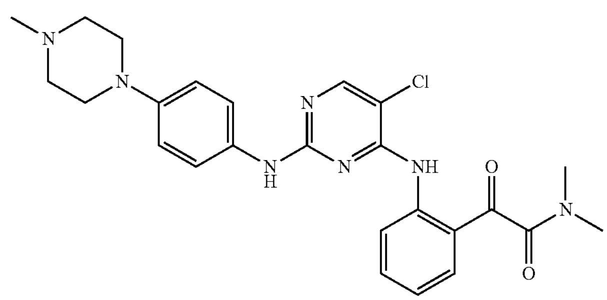 | 493.2 |
| 120 | N-(5-(5-chloro-4-(2-(2-(dimethylamino)-2-oxoacetyl)phenylamino)pyrimidin-2-ylamino)-2-(2-(dimethylamino)ethoxy)phenyl)propionamide | 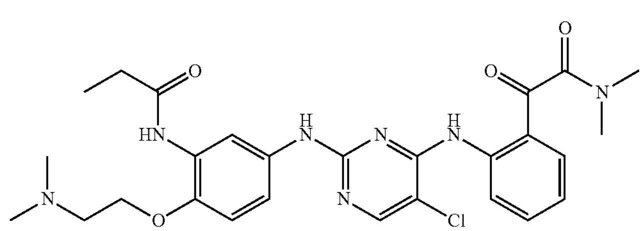 | 553.2 |

| EX No. | Chemical Name | Structure | Physical Data (MS) (M + H)+ |
|---|---|---|---|
| 121 | (E)-N-(5-(5-chloro-4-(2-(2-(dimethylamino)-2-oxoacetyl)phenylamino)pyrimidin-2-ylamino)-2-(4-methylpiperazin-1-yl)phenyl)-3-(dimethylamino)acrylamide | 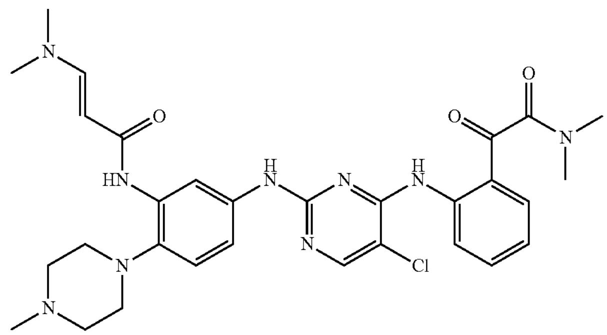 | 605.3 |
| 122 | N-(5-(5-chloro-4-(2-(2-(dimethylamino)-2-oxoacetyl)phenylamino)pyrimidin-2-ylamino)-2-propoxyphenyl)acrylamide | 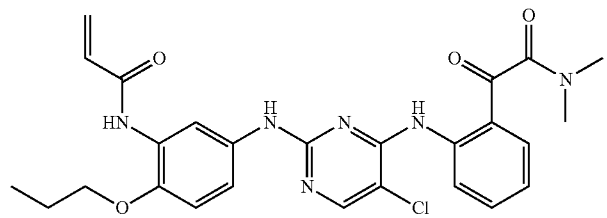 [SMILES: C=CC(=O)Nc1cc(Nc2ncc(Cl)c(Nc3ccccc3C(=O)C(=O)N(C)C)n2)ccc1OCCC] | 522.2 |
| 123 | N-(5-(5-chloro-4-(2-(2-(dimethylamino)-2-oxoacetyl)phenylamino)pyrimidin-2-ylamino)-2-fluorophenyl)-3-morpholino propanamide | 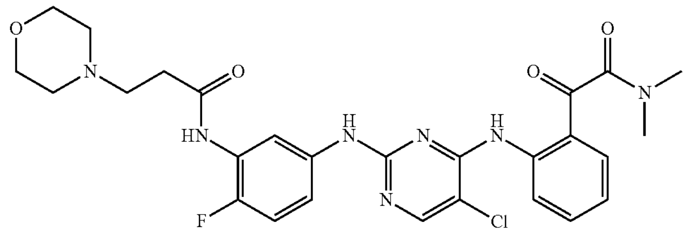 [SMILES: CN(C)C(=O)C(=O)c1ccccc1Nc1nc(Nc2ccc(F)c(NC(=O)CCN3CCOCC3)c2)ncc1Cl] | 569.2 |

Example 124. Synthesis of Compound 124

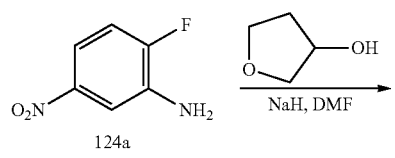

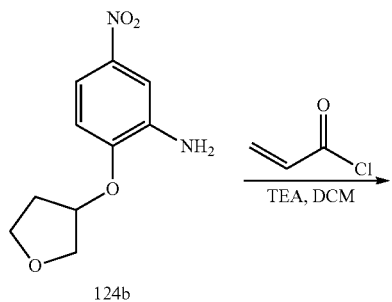

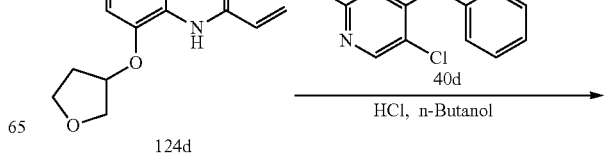

-continued

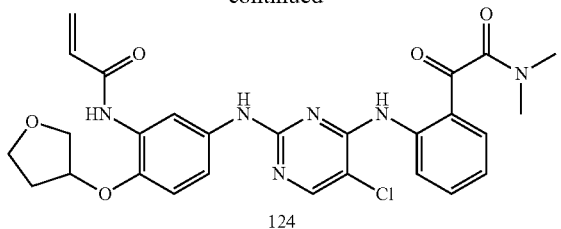

124

To a stirred solution of 3-hydroxy tetrahydrofuran (203 mg) in DMF (10 ml) at 0° C., NaH (92 mg) was added slowly. After the mixture was stirred at 0-5° C. for 30 minutes, the compound 124a (300 mg) in DMF was added dropwised. Then the reaction mixture was stirred with warming naturally to the room temperature. The reaction was complete detected by TLC (PE:EA=1:1) after 4 hours. Then 15 ml H₂O was added to the solution. Afterwards, the mixture was extracted by EA (15 ml×2). The combined organic phase was combined and washed with aqueous solution of NaCl and dried over Na₂SO₄ and concentrated under reduced pressure to give crude Compound 124b. The crude product was purified by column chromatography to give 226 mg Compound 124b.

To a stirred solution of Compound 124b (220 mg) and TEA (0.2 ml) in DCM (15 ml) at 0° C., a solution of acryloyl chloride (0.1 ml) in DCM (2.0 ml) was added dropwised. The reaction mixture was stirred at 0° C. for 30 minutes. Then the reaction was complete detected by TLC (PE:EA=1:1). The reaction solution was washed by water (20 ml) and the organic phase was concentrated under reduced pressure to give 220 mg Compound 124c.

To a stirred solution of Compound 124c (220 mg) in ethanol (5 ml), Fe powder (500 mg) and saturated aqueous solution of NH₄Cl (15 ml) was added. Then the reaction mixture was heated to 90° C. and stirred until the reaction was complete detected by TLC (DCM:MeOH=10:1). The reaction solution was filtered and the filtrate was partitioned between ethyl acetate (20 ml) and water (10 ml) 2 times. Then the combined organic phase was washed with aqueous solution of NaCl and dried over Na₂SO₄ and concentrated under reduced pressure to give 160 mg Compound 124d.

A mixture solution of Compound 124d (150 mg), 40d (205 mg) and con-HCl (0.05 ml) in n-Butanol was heated to 85° C. with stirring for 3 hrs. The reaction was complete detected by TLC (DCM:MeOH=10:1). Then, after the reaction mixture was cooled to 20° C., it was filtered and the filter cake was dried to give 115 mg Compound 124. MS: 550.2 (M+H)⁺. H-NMR (DMSO-d6, 400 MHz): 11.38 (s, 1H), 9.81 (s, 1H), 9.19 (s, 1H), 8.90 (s, 1H), 8.40 (s, 1H), 8.22 (s, 1H), 7.64-7.69 (m, 2H), 7.32-7.36 (m, 1H), 7.23-7.27 (t, 1H), 7.00 (d, 1H), 6.64-6.71 (dd, 1H), 6.18-6.22 (dd, 1H), 5.71-5.74 (dd, 1H), 5.02 (d, 1H), 3.87-3.94 (m, 2H), 3.73-3.78 (m, 2H), 3.00 (s, 3H), 2.90 (s, 3H), 2.19 (m, 1H), 2.05-2.10 (m, 1H).

| EX No. | Chemical Name | Structure | Physical Data (MS) (M + H)⁺ |
|---|---|---|---|
| 125 | N-(3-(5-chloro-4-(2-(2-(dimethylamino)-2-oxoacetyl)phenylamino)pyrimidin-2-ylamino)phenyl)-2-(((2-(dimethylamino)ethyl)(methyl)amino)methyl)acrylamide | 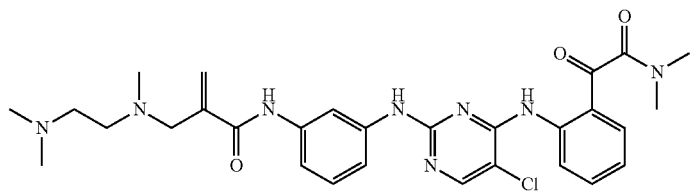 | 578.3 |
| 126 | N-(3-(5-chloro-4-(2-(2-(dimethylamino)-2-oxoacetyl)phenylamino)pyrimidin-2-ylamino)-4-methoxyphenyl)-2-(((2-(dimethylamino)ethyl)(methyl)amino)methyl)acrylamide | 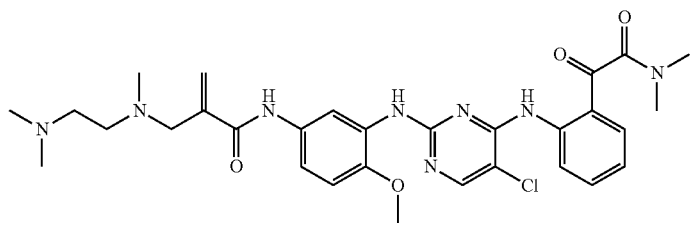 | 608.3 |
| 127 | N-(3-(5-chloro-4-(2-(2-((2-(dimethylamino)ethyl)(methyl)amino)-2-oxoacetyl)phenylamino)pyrimidin-2-ylamino)-4-methoxyphenyl)acrylamide | 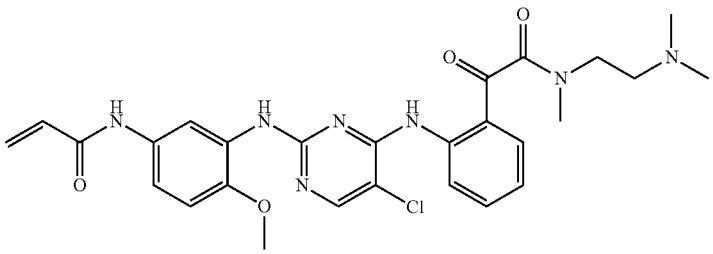 [SMILES: C=CC(=O)Nc1ccc(OC)c(Nc2ncc(Cl)c(Nc3ccccc3C(=O)C(=O)N(C)CCN(C)C)n2)c1] | 551.2 |

| EX No. | Chemical Name | Structure | Physical Data (MS) (M + H)+ |
|---|---|---|---|
| 128 | N-(5-(5-chloro-4-(2-(2-(dimethylamino)-2-oxoacetyl)phenylamino)pyrimidin-2-ylamino)-2-(4-methylpiperazin-1-yl)phenyl)-2-(piperidin-1-ylmethyl)acrylamide | 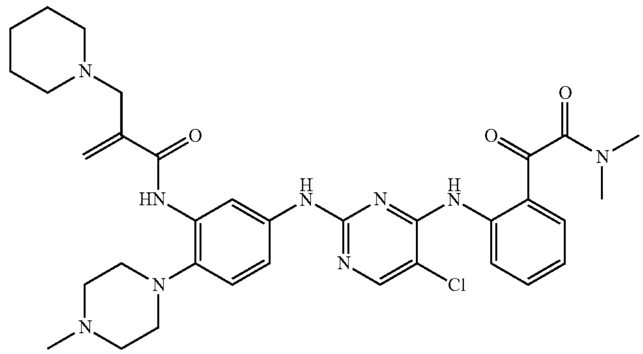 [SMILES: C=C(CN1CCCCC1)C(=O)Nc1cc(Nc2ncc(Cl)c(Nc3ccccc3C(=O)C(=O)N(C)C)n2)ccc1N1CCN(C)CC1] | 659.3 |
| 129 | N-(5-(5-chloro-4-(2-(2-(dimethylamino)-2-oxoacetyl)phenylamino)pyrimidin-2-ylamino)-2-morpholinophenyl)-2-(piperidin-1-ylmethyl)acrylamide | 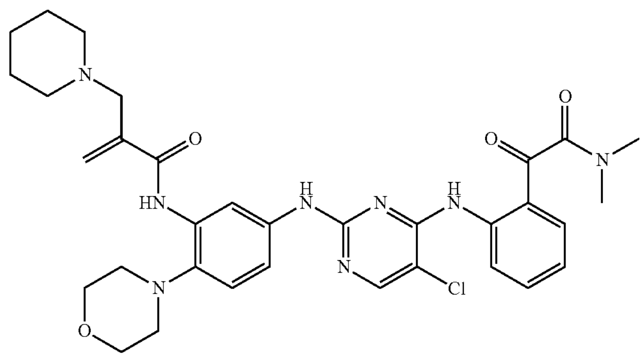 [SMILES: C=C(CN1CCCCC1)C(=O)Nc1cc(Nc2ncc(Cl)c(Nc3ccccc3C(=O)C(=O)N(C)C)n2)ccc1N1CCOCC1] | 646.3 |
| 130 | 2-(2-(5-chloro-2-(3-methoxy-4-(4-methylpiperazin-1-yl)phenylamino)pyrimidin-4-ylamino)phenyl)-N,N-diethyl-2-oxo acetamide | 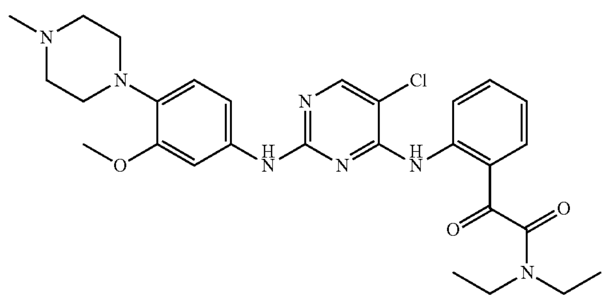 [SMILES: CCN(CC)C(=O)C(=O)c1ccccc1Nc1nc(Nc2ccc(N3CCN(C)CC3)c(OC)c2)ncc1Cl] | 551.2 |
| 131 | N-(3-(5-chloro-4-(2-(2-(diethylamino)-2-oxoacetyl)phenylamino)pyrimidin-2-ylamino)-4-methoxyphenyl)acrylamide | 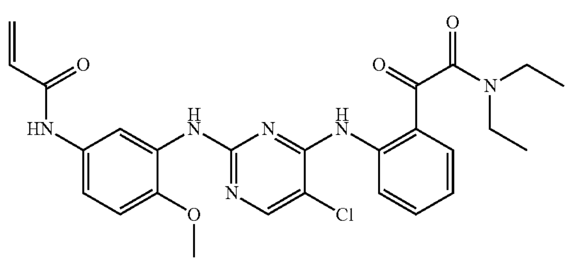 [SMILES: C=CC(=O)Nc1ccc(OC)c(Nc2ncc(Cl)c(Nc3ccccc3C(=O)C(=O)N(CC)CC)n2)c1] | 522.2 |
| 132 | N-(5-(5-chloro-4-(2-(2-(diethylamino)-2-oxoacetyl)phenylamino)pyrimidin-2-ylamino)-2-methoxyphenyl)acrylamide | 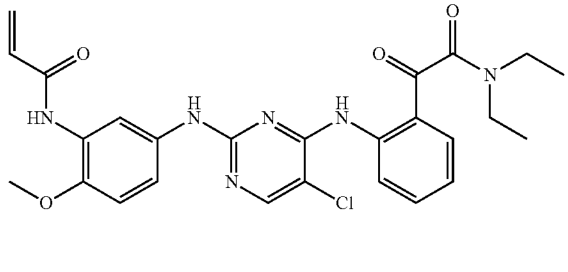 [SMILES: C=CC(=O)Nc1cc(Nc2ncc(Cl)c(Nc3ccccc3C(=O)C(=O)N(CC)CC)n2)ccc1OC] | 522.2 |

| EX No. | Chemical Name | Structure | Physical Data (MS) (M + H)+ |
|---|---|---|---|
| 133 | N-(3-(5-chloro-4-(2-(2-(dimethylamino)-2-oxoacetyl)phenylamino)pyrimidin-2-ylamino)-5-(trifluoromethyl)phenyl) acrylamide | 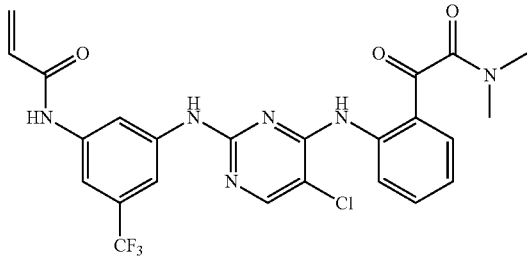 [SMILES: C=CC(=O)Nc1cc(Nc2ncc(Cl)c(Nc3ccccc3C(=O)C(=O)N(C)C)n2)cc(C(F)(F)F)c1] | 532.1 |
| 134 | N-(3-(5-chloro-4-(2-(2-(dimethylamino)-2-oxoacetyl)phenylamino)pyrimidin-2-ylamino)-4-((2-(dimethylamino)ethyl)(methyl)amino)phenyl)acrylamide | 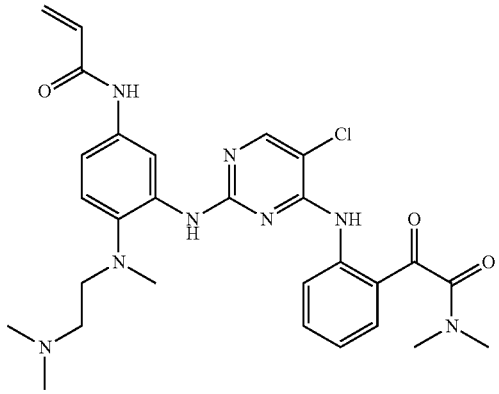 | 564.2 |
| 135 | N-(3-(5-chloro-4-(2-(2-(dimethylamino)-2-oxoacetyl)phenylamino)pyrimidin-2-ylamino)-4-(4-methylpiperazin-1-yl)phenyl)acrylamide | 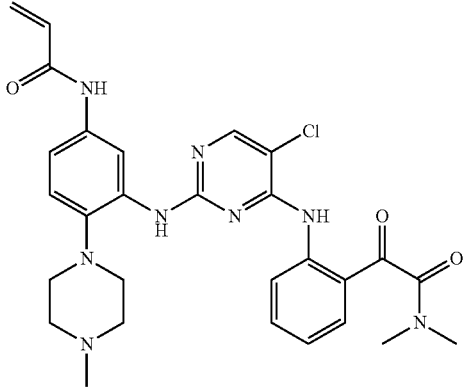 [SMILES: C=CC(=O)Nc1ccc(N2CCN(C)CC2)c(Nc2ncc(Cl)c(Nc3ccccc3C(=O)C(=O)N(C)C)n2)c1] | 562.2 |
| 136 | N-(3-(5-chloro-4-(2-(2-(dimethylamino)-2-oxoacetyl)phenylamino)pyrimidin-2-ylamino)-4-(tetrahydrofuran-3-yloxy)phenyl)acrylamide | 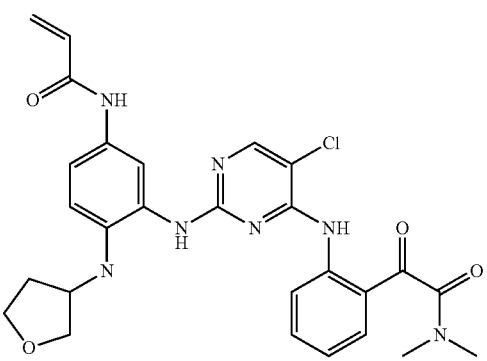 [SMILES: C=CC(=O)Nc1ccc(NC2CCOC2)c(Nc2ncc(Cl)c(Nc3ccccc3C(=O)C(=O)N(C)C)n2)c1] | 550.2 |

| EX No. | Chemical Name | Structure | Physical Data (MS) (M + H)+ |
|---|---|---|---|
| 137 | N-(5-(5-chloro-4-(2-(2-(dimethylamino)-2-oxoacetyl)phenylamino)pyrimidin-2-ylamino)-2-((2-(dimethylamino)ethoxy)methyl)phenyl)acrylamide | 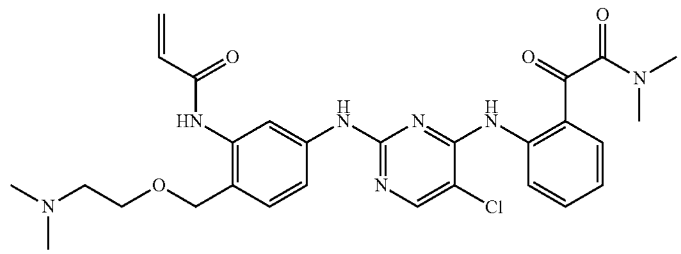 | 565.2 |
| 138 | N-(5-(5-chloro-4-(2-(2-(dimethylamino)-2-oxoacetyl)phenylamino)pyrimidin-2-ylamino)-2-((2-(dimethylamino)ethoxy)methyl)-4-methoxyphenyl)acrylamide | 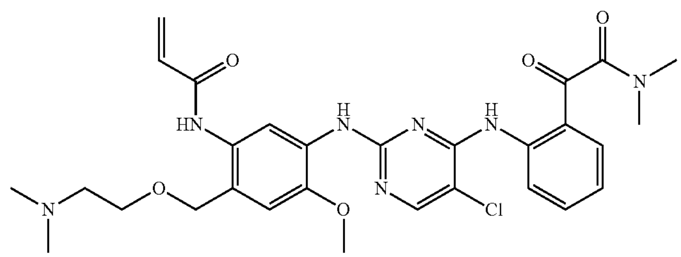 | 595.2 |
| 139 | N-(5-(5-chloro-4-(2-(2-(dimethylamino)-2-oxoacetyl)phenylamino)pyrimidin-2-ylamino)-2-((dimethylamino)methyl)phenyl)acrylamide | 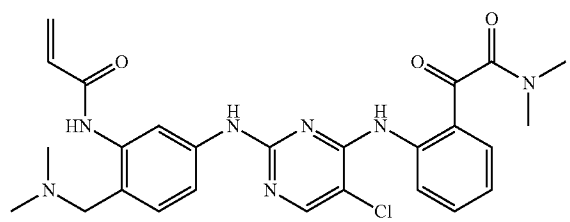 | 521.2 |
| 140 | N-(5-(5-chloro-4-(2-(2-(dimethylamino)-2-oxoacetyl)phenylamino)pyrimidin-2-ylamino)-2-((dimethylamino)methyl)-4-methoxyphenyl)acrylamide | 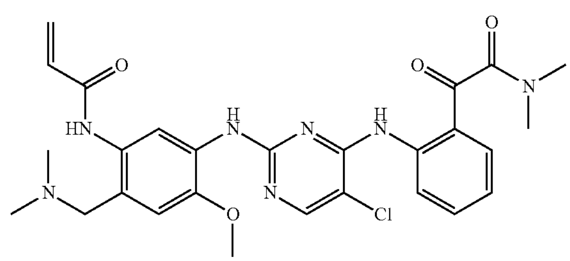 | 551.2 |
| 141 | N-(5-(5-chloro-4-(2-(2-(dimethylamino)-2-oxoacetyl)phenylamino)pyrimidin-2-ylamino)-2-((4-methylpiperazin-1-yl)methyl)phenyl)acrylamide | 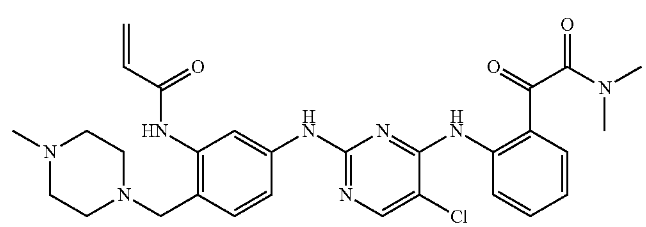 | 576.2 |
| 142 | N-(5-(5-chloro-4-(2-(2-(dimethylamino)-2-oxoacetyl)phenylamino)pyrimidin-2-ylamino)-4-methoxy-2-((4-methylpiperazin-1-yl)methyl)phenyl)acrylamide | 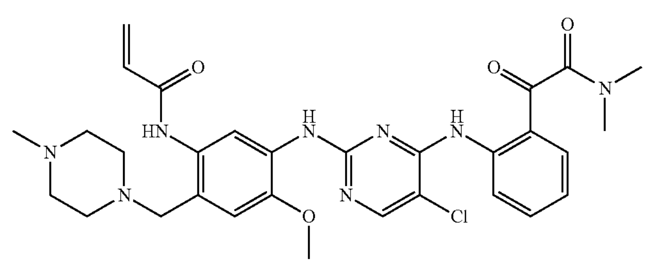 | 606.2 |

Example 143. Synthesis of Compound 143
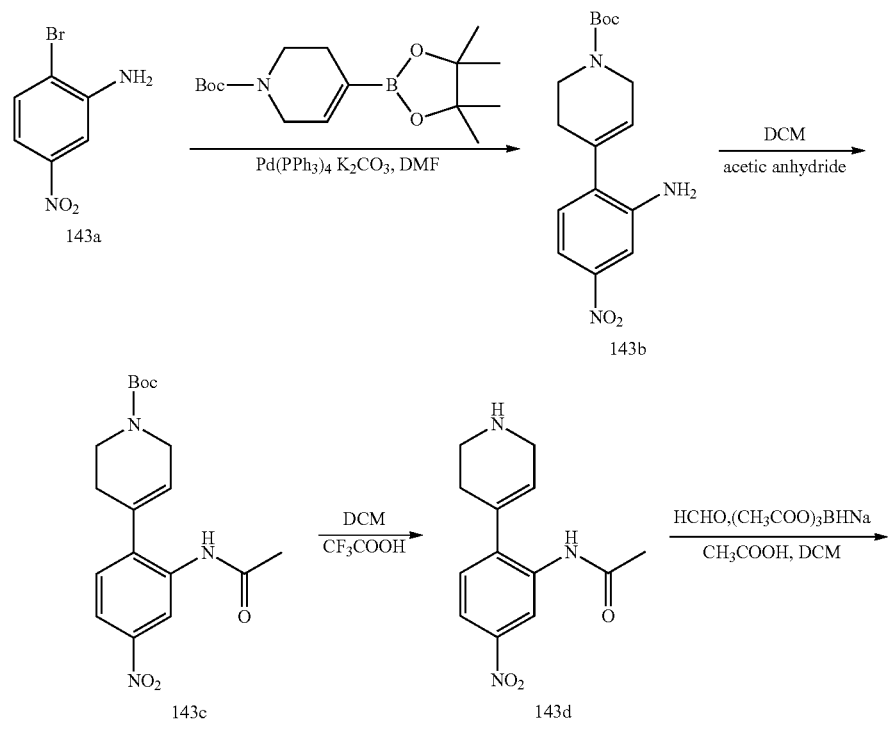
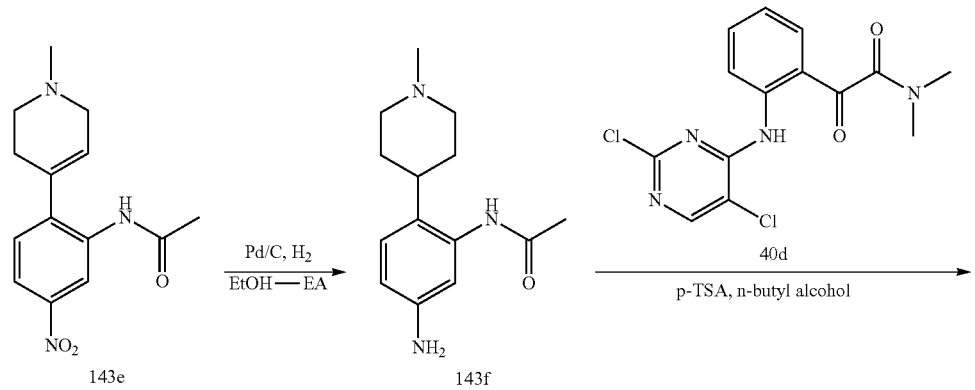
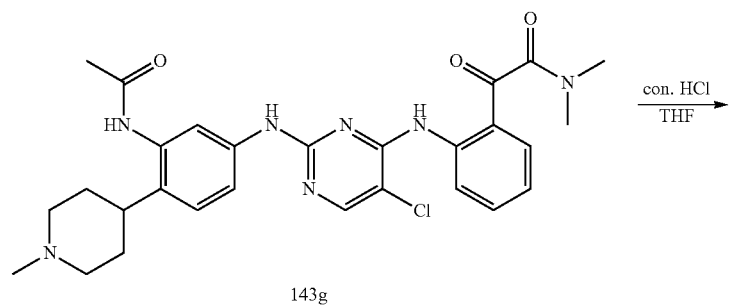

-continued

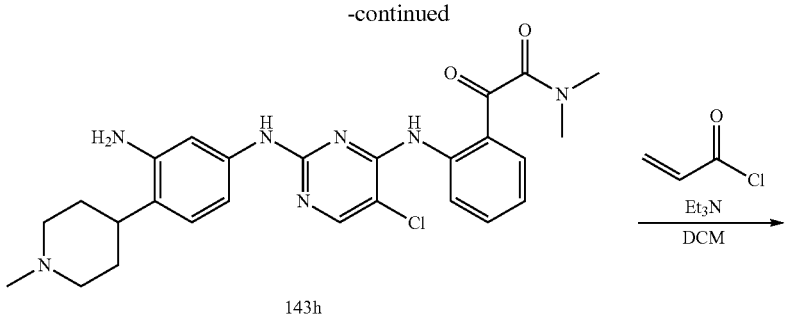

143h

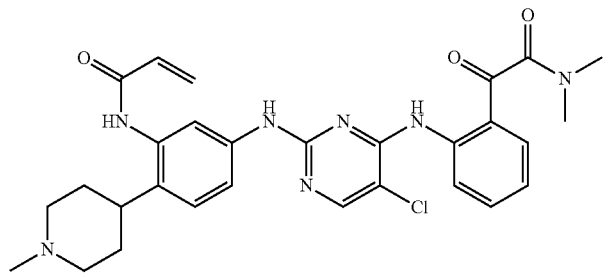

143

A mixture of Compound 143a (5.12 g, 23.59 mmol), tert-butyl 4-(4,4,5,5-tetramethyl-1,3,2-dioxaborolan-2-yl)-5,6-dihydropyridine-1(2H)-car-boxylate (7.30 g, 23.59 mmol), tetrakis (triphenylphosphine) palladium(0) (1.36 g, 1.18 mmol) and $K_2CO_3$ (8.15 g, 58.98 mmol) in DMF (200 ml) was degassed with five vacuum/nitrogen cycles. The mixture was heated to 80° C. with stirring under nitrogen for 16.5 hours. After cooled to 10° C., water (300 ml) was added, and the resulting mixture was extracted with ethyl acetate (300 ml, 150 ml×2). The combined organic extracts were washed with brine (200 ml×2), dried over anhydrous $Na_2SO_4$ and then evaporated under reduced pressure. The residue was purified by chromatography to give 4.82 g Compound 143b as a yellow solid.

A mixture of Compound 143b (4.81 g, 15.08 mmol), acetic anhydride (5 ml, 52.89 mmol) in DCM (300 ml) was stirred at 25° C. for 20 hours. After concentrated in under reduced pressure, the residue was dissolved in saturated aqueous solution of sodium bicarbonate (200 ml) with stirring for 12 hours at ambient temperature. The precipitated solid was collected by filtration to give 5.28 g Compound 143c.

A mixture solution of Compound 143c (5.27 g, 14.58 mmol) and trifluoroacetic acid (13 ml, 175 mmol) in DCM was stirred at 40° C. for 2 hours. The progress of the reaction was monitored by TLC. After completion of the reaction, the reaction mixture was concentrated under reduced pressure, the residue (Compound 143d) was used for the next step without further purification.

A mixture of Compound 143d (3.80 g, 14.54 mmol), formaldehyde solution (5 ml, 178.90 mmol), acetic acid (1 ml, 17.48 mmol), sodium triacetoxyborohyride (9.25 g, 43.65 mmol) and DCM (150 ml) was stirred at ambient temperature for 20 mins. Saturated aqueous solution of $K_2CO_3$ (100 ml) was added, the resulting mixture was extracted with DCM (100 ml×2). The combined organic layers were washed with brine (100 ml), dried over anhydrous $Na_2SO_4$, then concentrated under reduced pressure and the residue (Compound 143e) was used for the next step without further purification.

To a solution of Compound 143e (3.81 g, 13.84 mmol) in EA (100 ml) and EtOH (100 ml) was added palladium 10% on carbon (1.05 g). The resulting mixture was stirred at ambient under hydrogen atmosphere for 2 hours. After completion of the reaction, the reaction mixture was filtered and the filtrate was concentrated to give 3.21 g Compound 143f.

A mixture of Compound 143f (3.21 g, 12.99 mmol), Compound 40d (4.40 g, 12.99 mmol), p-toluenesulfonic acid (2.68 g, 15.59 mmol) and n-butyl alcohol (150 ml) was heated to 100° C. with stirring for 7 hours. The mixture was cooled and concentrated under reduced pressure, the residue was purified by chromatography to give 5.02 g Compound 143 g as a light yellow solid.

To a stirred solution of Compound 143 g (1.98 g, 3.60 mmol) in THF (50 ml) was added con.hydrochloric acid (15 ml), the resulting mixture was stirred at 65° C. for 17 hours. Reaction was monitored by TLC. After completion of the reaction, the mixture was cooled to 0-5° C. and saturated aqueous solution of $K_2CO_3$ was added to adjust pH value to 9-10, then extracted with DCM (100 ml×2), the combined organic extracts was washed with brine (100 ml), dried over anhydrous $Na_2SO_4$ and evaporated under reduced pressure. Crude product was purified by chromatography to give 0.28 g Compound 143 h as a yellow solid.

To a solution of Compound 143 h (255 mg, 0.5 mmol), triethylamine (100 mg, 1.0 mmol) in DCM (100 ml) was added acryloyl chloride (69 mg, 0.75 mmol) dropwise and the mixture was stirred at 0-5° C. Reaction was quenched with saturated aqueous solution of potassium carbonate (200 ml), extracted with DCM (100 ml×3), the combined organic extracts was washed with brine (100 ml×2), dried over anhydrous $Na_2SO_4$ and evaporated under reduced pressure, the residue was purified by Pre-TLC to give 138 mg Compound 143 as a yellow solid. MS: 561.2 $(M+H)^+$. HNMR (DMSO-d6, 400 MHz): 11.32 (s, 1H), 9.61 (s, 1H), 9.02 (d, 1H), 8.33 (s, 1H), 7.63-7.80 (m, 3H), 7.50 (d, 1H), 7.20-7.23 (m, 2H), 6.46-6.53 (m, 1H), 6.19-6.23 (dd, 1H), 5.72-5.75 (dd, 1H), 3.01 (s, 3H), 2.91 (s, 3H), 2.87 (s, 2H), 2.61-2.67 (m, 1H), 2.21 (s, 3H), 1.98 (m, 2H), 1.63-1.65 (m, 4H).

| EX No. | Chemical Name | Structure | Physical Data (MS) (M + H)+ |
|---|---|---|---|
| 144 | N-(5-(5-chloro-4-(2-(2-(dimethylamino)-2-oxoacetyl)phenylamino)pyrimidin-2-ylamino)-4-methoxy-2-(1-methyl-piperidin-4-yl)phenyl)acrylamide | 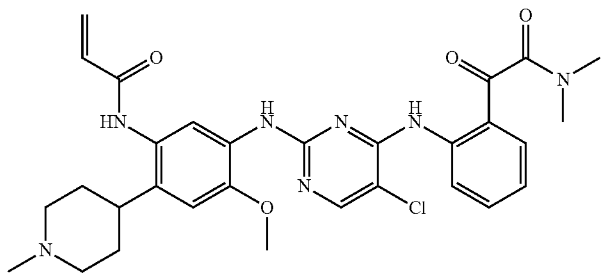 | 591.2 |
| 145 | 2-(2-(5-chloro-2-(3-methoxy-4-(1-methylpiperidin-4-yl)phenylamino)pyrimidin-4-ylamino)phenyl)-N,N-dimethyl-2-oxo-acetamide | 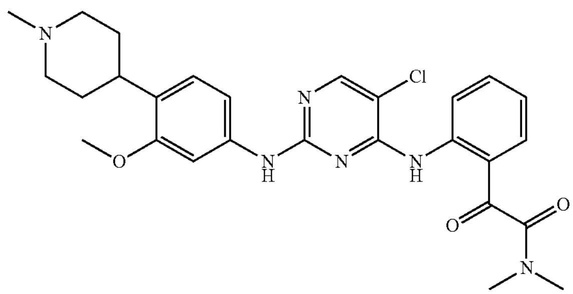 [SMILES: COc1cc(Nc2ncc(Cl)c(Nc3ccccc3C(=O)C(=O)N(C)C)n2)ccc1C1CCN(C)CC1] | 522.2 |
| 146 | 2-(2-(2-(4-(1-acetylpiperidin-4-yl)-3-methoxyphenylamino)-5-chloropyrimidin-4-ylamino)phenyl)-N,N-dimethyl-2-oxo acetamide | 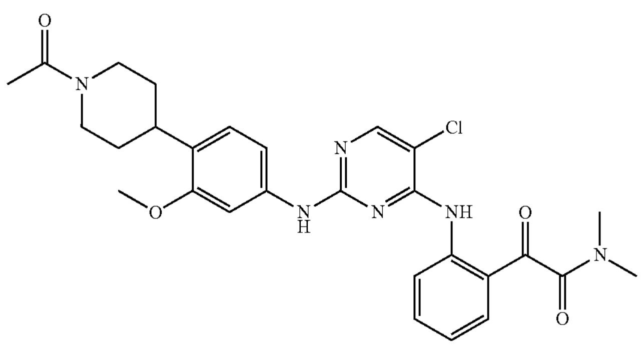 | 550.2 |
| 147 | N-(5-(5-chloro-4-(2-(2-(dimethylamino)-2-oxoacetyl)phenylamino)pyrimidin-2-ylamino)-2-(2-(dimethylamino)ethyl)phenyl)acrylamide | 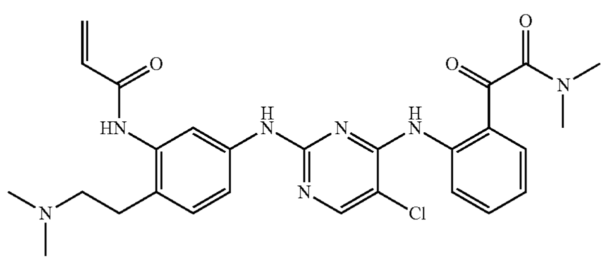 | 535.2 |
| 148 | N-(5-(5-chloro-4-(2-(2-(dimethylamino)-2-oxoacetyl)phenylamino)pyrimidin-2-ylamino)-2-(3-(dimethylamino)propyl)phenyl)acrylamide | 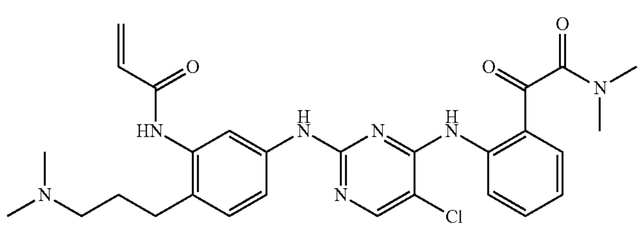 | 549.2 |

-continued

| EX No. | Chemical Name | Structure | Physical Data (MS) (M + H)+ |
|---|---|---|---|
| 149 | 2-(2-(5-chloro-2-(4-(1-isopropylpiperidin-4-yl)-3-methoxyphenylamino)pyrimidin-4-ylamino)phenyl)-N,N-dimethyl-2-oxoacetamide | 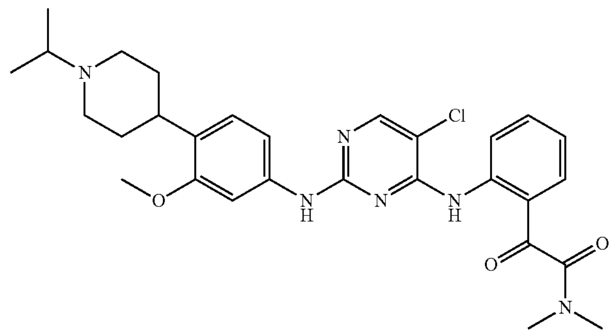 [SMILES: COc1cc(Nc2ncc(Cl)c(Nc3ccccc3C(=O)C(=O)N(C)C)n2)ccc1C1CCN(C(C)C)CC1] | 550.3 |
| 150 | 2-(2-(5-chloro-2-(2-isopropoxy-5-methyl-4-(piperidin-4-yl)phenylamino)pyrimidin-4-ylamino)phenyl)-N,N-dimethyl-2-oxoacetamide | 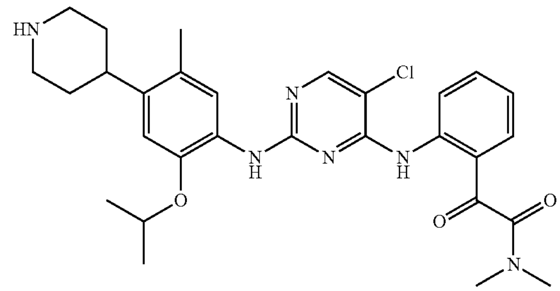 [SMILES: Cc1cc(Nc2ncc(Cl)c(Nc3ccccc3C(=O)C(=O)N(C)C)n2)c(OC(C)C)cc1C1CCNCC1] | 550.3 |

Pharmacological Testing

Example A. Kinase Assays (Single Dose Inhibition)

Assays were conducted for an in vitro kinase panel having EGFR WT, L858R, T790M, L858R/T790M and ALK. Assay conditions included 10 μM ATP and 100 nM test compounds.

Assay Protocol:

All reactions are initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting. This assay is performed by Millipore. The experiment is carried out in duplicate. The value for the control sample (DMSO) was set to 100%, and the values for the compound-treated samples were expressed as activity relative to the control sample.

Kinase-Specific Assay Conditions

Alk (h) is incubated with 8 mM MOPS pH7.0, 0.2 mM EDTA, 250 μM KKKSPGEYVNIEFG, 10 mM MgAcetate, [γ-$^{33}$P-ATP] (specific activity approx. 500 cpm/pmol, concentration as required) and 0.1 μM test compound.

EGFR (h) and EGFR (L858R) (h) are incubated with 8 mM MOPS pH7.0, 0.2 mM EDTA, 10 mM MnCl$_2$, 0.1 mg/mL poly(Glu, Tyr)4:1, 10 mM MgAcetate, [γ-$^{33}$P-ATP] (specific activity approx. 500 cpm/pmol, concentration as required) and 0.1 μM test compound.

EGFR (T790M) (h) and EGFR (T790M, L858R) (h) are incubated with 8 mM MOPS pH7.0, 0.2 mM EDTA, 250 μM GGMEDIYFEFMGGKKK, 10 mM MgAcetate, [γ-$^{33}$P-ATP] (specific activity approx. 500 cpm/pmol, concentration as required) and 0.1 μM test compound.

TABLE 1

| Example | Activity (control) % | | | | |
|---|---|---|---|---|---|
| | ALK (h) | EGFR (h) | EGFR (L858R) (h) | EGFR (T790M) (h) | EGFR (T790M, L858R) (h) |
| CO-1686@0.1 μM | 49 | 92 | 97 | 21 | 7 |
| 4 @0.1 μM | 8 | 65 | 8 | 4 | 2 |
| 40 @0.1 μM | 28 | 106 | 103 | 79 | 24 |
| 53 @0.1 μM | 5 | 109 | 60 | 21 | 4 |
| 61 @0.1 μM | 5 | 101 | 70 | 54 | 13 |
| 64 @0.1 μM | 47 | 106 | 100 | 79 | 39 |
| 65 @0.1 μM | 19 | 118 | 102 | 80 | 25 |
| 66 @0.1 μM | 35 | 107 | 104 | 66 | 24 |
| 67 @0.1 μM | 13 | 105 | 85 | 50 | 9 |
| 41 @0.1 μM | 21 | 76 | 39 | 2 | 3 |
| 72 @0.1 μM | 14 | 102 | 28 | 54 | 9 |
| 73 @0.1 μM | 17 | 67 | 37 | 3 | 3 |
| 74 @0.1 μM | 9 | 110 | 73 | 62 | 12 |
| 78 @0.1 μM | 36 | 68 | 37 | 2 | 3 |
| 79 @0.1 μM | 7 | 92 | 25 | 16 | 2 |
| 80 @0.1 μM | 10 | 101 | 43 | 42 | 7 |
| 102 @0.1 μM | 5 | 98 | 57 | 40 | 5 |
| 87 @0.1 μM | 5 | 88 | 44 | 8 | 1 |
| 89 @0.1 μM | 8 | 67 | 10 | 5 | 1 |
| 94 @0.1 μM | 6 | 100 | 84 | 45 | 9 |
| 97 @0.1 μM | 23 | 74 | 46 | 2 | 6 |
| 101 @0.1 μM | 35 | 110 | 94 | 83 | 41 |
| 123 @0.1 μM | 17 | 115 | 94 | 84 | 31 |
| 111 @0.1 μM | 8 | 109 | 76 | 59 | 11 |
| 112 @0.1 μM | 21 | 85 | 66 | 14 | 1 |
| 113 @0.1 μM | 19 | 88 | 78 | 16 | 3 |
| 114 @0.1 μM | 10 | 91 | 52 | 47 | 8 |
| 115 @0.1 μM | 6 | 73 | 45 | 12 | 3 |
| 117 @0.1 μM | 8 | 113 | 88 | 65 | 14 |
| 118 @0.1 μM | 3 | 82 | 29 | 18 | 2 |
| 120 @0.1 μM | 8 | 115 | 76 | 62 | 14 |
| 124 @0.1 μM | 16 | 109 | 100 | 78 | 20 |
| 125 @0.1 μM | 20 | 106 | 54 | 18 | 2 |

TABLE 1-continued

| Example | ALK (h) | EGFR (h) | EGFR (L858R) (h) | EGFR (T790M) (h) | EGFR (T790M, L858R) (h) |
|---|---|---|---|---|---|
| 126 @0.1 μM | 19 | 93 | 47 | 5 | 2 |
| 129 @0.1 μM | 8 | 104 | 75 | 24 | 3 |
| 130 @0.1 μM | 13 | 113 | 98 | 84 | 22 |
| 131 @0.1 μM | 9 | 104 | 104 | 82 | 27 |
| 132 @0.1 μM | 16 | 103 | 114 | 77 | 30 |
| 135 @0.1 μM | 80 | 106 | 103 | 96 | 95 |
| 136 @0.1 μM | 29 | 99 | 104 | 92 | 54 |

Example B. Kinase Assays ($IC_{50}$)

Assays were conducted for an in vitro kinase panel having EGFR WT, L858R, T790M, L858R/T790M and ALK. Assay conditions included 10 pt curves with 1 μM (EGFR L858R, T790M, L858R/T790M and ALK) or 10 μM (EGFR WT) top concentration (duplicates) and Km ATP.

Kinase Assay Protocol:

Bar-coded Corning, low volume NBS, black 384-well plate (Corning Cat. #4514)

1. 2.5 μL—4× Test Compound or 100 nL 100× plus 2.4 μL kinase buffer;
2. 5 μL—2× Peptide/Kinase Mixture;
3. 2.5 μL—4×ATP Solution;
4. 30-second plate shake;
5. 60-minute Kinase Reaction incubation at room temperature;
6. 5 μL—Development Reagent Solution;
7. 30-second plate shake;
8. 60-minute Development Reaction incubation at room temperature;
9. Read on fluorescence plate reader and analyze the data.

Kinase-Specific Assay Conditions:

ALK

The 2×ALK/Tyr 01 mixture is prepared in 50 mM HEPES pH 7.5, 0.01% BRIJ-35, 10 mM $MgCl_2$, 1 mM EGTA. The final 10 μL Kinase Reaction consists of 4.25-96 ng ALK and 2 μM Tyr 01 in 50 mM HEPES pH 7.5, 0.01% BRIJ-35, 10 mM $MgCl_2$, 1 mM EGTA. After the 1 hour Kinase Reaction incubation, 5 μL of a 1:256 dilution of Development Reagent B is added.

EGFR (ErbB1)

The 2×EGFR (ErbB1)/Tyr 04 mixture is prepared in 50 mM HEPES pH 7.5, 0.01% BRIJ-35, 10 mM $MgCl_2$, 4 mM $MnCl_2$, 1 mM EGTA, 2 mM DTT. The final 10 μL Kinase Reaction consists of 1.1-8 ng EGFR (ErbB1) and 2 μM Tyr 04 in 50 mM HEPES pH 7.5, 0.01% BRIJ-35, 10 mM MgCl2, 2 mM $MnCl_2$, 1 mM EGTA, 1 mM DTT. After the 1 hour Kinase Reaction incubation, 5 μL of a 1:64 dilution of Development Reagent B is added.

EGFR (ErbB1) L858R

The 2×EGFR (ErbB1) L858R/Tyr 04 mixture is prepared in 50 mM HEPES pH 7.5, 0.01% BRIJ-35, 10 mM $MgCl_2$, 4 mM $MnCl_2$, 1 mM EGTA, 2 mM DTT. The final 10 μL Kinase Reaction consists of 0.2-3.36 ng EGFR (ErbB1) L858R and 2 μM Tyr 04 in 50 mM HEPES pH 7.5, 0.01% BRIJ-35, 10 mM $MgCl_2$, 2 mM $MnCl_2$, 1 mM EGTA, 1 mM DTT. After the 1 hour Kinase Reaction incubation, 5 μL of a 1:64 dilution of Development Reagent B is added.

EGFR (ErbB1) T790M

The 2×EGFR (ErbB1) T790M/Tyr 04 mixture is prepared in 50 mM HEPES pH 6.5, 0.01% BRIJ-35, 10 mM $MgCl_2$, 1 mM EGTA, 0.02% $NaN_3$. The final 10 μL Kinase Reaction consists of 3.9-34.8 ng EGFR (ErbB1) T790M and 2 μM Tyr 04 in 50 mM HEPES pH 7.0, 0.01% BRIJ-35, 10 mM $MgCl_2$, 1 mM EGTA, 0.01% $NaN_3$. After the 1 hour Kinase Reaction incubation, 5 μL of a 1:64 dilution of Development Reagent B is added.

EGFR (ErbB1) T790M L858R

The 2×EGFR (ErbB1) T790M L858R/Tyr 04 mixture is prepared in 50 mM HEPES pH 6.5, 0.01% BRIJ-35, 10 mM $MgCl_2$, 1 mM EGTA, 0.02% $NaN_3$. The final 10 μL Kinase Reaction consists of 0.36-2.96 ng EGFR (ErbB1) T790M L858R and 2 μM Tyr 04 in 50 mM HEPES pH 7.0, 0.01% BRIJ-35, 10 mM $MgCl_2$, 1 mM EGTA, 0.01% $NaN_3$. After the 1 hour Kinase Reaction incubation, 5 μL of a 1:64 dilution of Development Reagent B is added.

Compounds formula (I) included potent inhibitors of EGFR mutants in kinase assays. For example, for the resistant mutant EGFR L858R/T790M, previously known inhibitors gefitinib, icotinib, and CO-1686 had $IC_{50}$ values between 16.6 nM to >1 μM, while many compounds of formula (I) exhibited $IC_{50}$ values in the range of 4.08 to 22.8 nM. Thus, compounds of formula (I) could provide the necessary inhibitors for EGFR-driven cancers.

TABLE 2

| | | $IC_{50}$/nm | | | |
|---|---|---|---|---|---|
| Example | ALK | EGFR (ErbB1) L858R | EGFR (ErbB1) T790M L858R | EGFR (ErbB1) T790M | EGFR (ErbB1) |
| Icotinib | | 2.02 | >1000 | >1000 | 1.23 |
| Gefitinib | | 0.458 | 412 | 179 | <0.508 |
| CO-1686 | 145 | 108 | 16.6 | 13.7 | 101 |
| 4 | 27.9 | 44.3 | 4.08 | 7.52 | 45.1 |
| 61 | 12.2 | >1000 | 22.8 | 38.2 | 756 |
| 67 | 17.3 | 500 | 15.4 | 18.9 | 273 |
| 74 | 9.33 | 422 | 15.5 | 15.8 | 513 |
| 87 | 15.1 | 225 | 14.7 | 21.3 | 354 |
| 115 | 8.62 | 547 | 11.7 | 18.7 | 397 |
| 118 | 10.8 | 158 | 5.13 | 4.92 | 77.6 |

Example C. Cell Proliferation Assay

NSCLC cell lines were used to examine the activity of compounds of formula (I) against 3 general forms of EGFR: wild type EGFR (the naturally occurring form, WT), EGFR with an activating mutation (delE746_A750 [Del]; this form is sensitive to first generation EGFR inhibitors), and EGFR with both an activating mutation and a T790M resistance mutation (L858R/T790M; the addition of the T790M mutation makes this form resistant to first generation EGFR inhibitors).

Effects of test compounds on in vitro proliferation were measured by MTS cell viability assay.

Cell Culture

H1975 (EGFR L858R/T790M), HCC827 (EGFR Del), A549 (EGFR WT) and A431(EGFR WT) NSCLC cells were all obtained from ATCC.

H1975 and HCC827 cells were maintained in RPMI 1640 (Gibco) supplemented with 10% FBS, 100 units/mL penicillin, 100 units/mL streptomycin, and 2 mM glutamine.

A549 cells were maintained in Ham's F12K medium (Gibco) supplemented with 10% FBS, 100 units/mL penicillin, 100 units/mL streptomycin, and 2 mM glutamine.

A431 cells were maintained in DMEM (Gibco) supplemented with 10% FBS, 100 units/mL penicillin, 100 units/mL streptomycin, and 2 mM glutamine.

MTS Cell Viability Assay:

1. Seed cells at density of 2×103 cells per well of 96-wells plates, grow for 24 hours;
2. Prepare test compounds in each well with a final medium volume of 200 μl;
3. Incubate for 3 days of exposure;
4. Prepare reagents following the instructions in the Cell Proliferation Assay kit (Promega);
5. Change to serum-free medium with a final volume of 100 μl/well. Prepare a set of wells with medium only for background subtraction;
6. Add 20 μl MTS solution containing PMS to each well (final concentration of MTS will be 0.33 mg/ml);
7. Incubate 1 to 4 hours at 37° C. in a humidified, 5% $CO_2$ atmosphere.
8. Record absorbance at 490 nm using VICTOR™X5 plate reader (PerkinElmer).

All experimental points were set up in three wells and all experiments were repeated at least three times.

The Compound of Example 40, 65, 66, 67, 74, 112 and 118 demonstrated potent activity against both activated and resistant T790M forms of EGFR in vitro cellular assays. For example, in one set of studies, proliferation of HCC827 cells expressing EGFR Del were inhibited with $GI_{50}$s of 20 nM by Example 67 and 118; and proliferation of H1975 cells expressing EGFR-L858R/T790M were inhibited with $GI_{50}$s (20 nM and 10 nM) similar to that of HCC827 cells.

In contrast, Example 67 and 118 were essentially inactive against EGFR WT in cellular assays, i.e., inhibited proliferation with $GI_{50}$s>1500 nM in A549 cells (EGFR WT), showing a great selectivity between EGFR WT and mutants. However the second generation EGFR TKI afatinib induced similar inhibition of proliferation on HCC827 cells (EGFR Del) and A431 cells (EGFR WT).

TABLE 3

| Example | $IC_{50}$ (H1975)/μM | $IC_{50}$ (HCC827)/μM | $IC_{50}$ (A549)/μM | $IC_{50}$ (A431)/μM |
|---|---|---|---|---|
| CO-1686 | 0.08 | 0.09 | 2.00 | 0.45 |
| WZ4002 | 0.15 | 0.03 | >3 | NA |
| 24 | >3 | >3 | NA | NA |
| 18 | 2.86 | >3 | NA | NA |
| 3 | 0.84 | 0.94 | >3 | NA |
| 17 | 0.86 | 1.23 | >3 | 0.26 |
| 16 | 1.13 | 0.90 | >3 | NA |
| 1 | >3 | >3 | NA | NA |
| 2 | >3 | >3 | NA | NA |
| 4 | >3 | 2.63 | >3 | NA |
| 15 | >3 | >3 | NA | NA |
| 10 | >3 | >3 | NA | NA |
| 42 | >3 | >3 | >3 | NA |
| 43 | >3 | >3 | >3 | NA |
| 44 | 1.23 | 2.36 | >3 | NA |
| 45 | >3 | >3 | >3 | NA |
| 46 | 0.81 | 1.63 | >3 | NA |
| 47 | >3 | >3 | >3 | NA |
| 48 | 1.95 | 1.94 | NA | NA |
| 25 | >3 | >3 | NA | NA |
| 49 | >3 | >3 | NA | NA |
| 53 | 0.21 | 0.54 | >3 | 0.05 |
| 40 | 0.01 | 0.07 | 0.64 | NA |
| 54 | >3 | >3 | NA | NA |
| 55 | >3 | >3 | NA | NA |
| 56 | >3 | >3 | NA | NA |
| 57 | 0.10 | 0.27 | >3 | NA |
| 58 | 0.98 | 0.53 | 0.37 | NA |
| 59 | 0.19 | >3 | >3 | NA |

TABLE 3-continued

| Example | $IC_{50}$ (H1975)/μM | $IC_{50}$ (HCC827)/μM | $IC_{50}$ (A549)/μM | $IC_{50}$ (A431)/μM |
|---|---|---|---|---|
| 60 | 0.15 | 0.87 | 2.08 | NA |
| 61 | 0.01 | 0.17 | 0.74 | 0.01 |
| 62 | >3 | 2.33 | >3 | NA |
| 63 | 0.64 | >3 | >3 | NA |
| 64 | 0.09 | 0.45 | >3 | NA |
| 65 | 0.02 | 0.12 | >3 | NA |
| 66 | 0.05 | 0.12 | >3 | NA |
| 67 | 0.02 | 0.02 | 1.58 | 0.11 |
| 68 | 0.65 | 1.20 | >3 | NA |
| 69 | 0.31 | 1.20 | >3 | NA |
| 70 | 0.31 | 1.05 | 1.37 | NA |
| 71 | 0.99 | 0.78 | 1.19 | NA |
| 74 | 0.05 | 0.03 | 0.62 | 0.05 |
| 87 | 0.01 | 0.02 | 0.05 | 0.06 |
| 118 | 0.01 | 0.02 | 1.89 | 0.01 |
| 112 | 0.01 | 0.03 | 0.04 | 0.10 |
| 126 | 0.01 | 0.02 | NA | 0.21 |
| 131 | 0.01 | 0.05 | NA | 0.75 |

The compounds of the present invention are preferably formulated as pharmaceutical compositions administered by a variety of routes. Most preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al, eds., 19$^{th}$ ed., Mack Publishing Co., 1995). The compounds of Formula I are generally effective over a wide dosage range.

For example, dosages per day normally fall within the range of about 1 mg to about 200 mg total daily dose, preferably 1 mg to 150 mg total daily dose, more preferably 1 mg to 50 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

What is claimed is:

1. A compound of Formula I or a pharmaceutically acceptable salt:

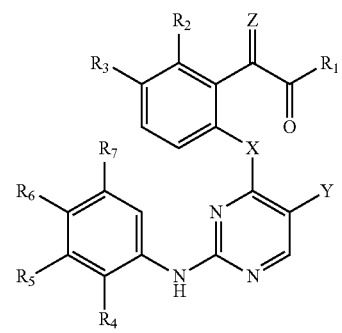

I wherein,
X is NH;
Y is halogen;

Z is O;
$R_1$ is $N(R_8)(R_9)$, wherein each $R_8$ and $R_9$ is independently H, or alkyl;
$R_2$ is H
$R_3$ is H
$R_4$ is $C_{1-6}$alkoxy;
$R_5$ is H or $C_{1-6}$alkyl
$R_7$ is $—NR_{22}C(O)CR_{23}=CR_{10}R_{11}$
wherein
each $R_{10}$, $R_{11}$, $R_{22}$ or $R_{23}$ is independently H, or alkyl
$R_6$ is

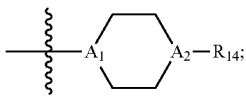

wherein
each $A_1$ or $A_2$ is, independently, CH or N; and $R_{14}$ is alkyl.

2. The compound of claim 1, wherein each $R_6$ is independently

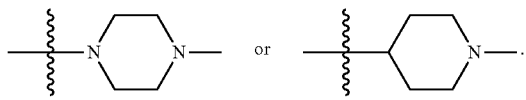

3. The compound of claim 1, wherein each $R_1$ is independently $—NHCH_3$, $—NCH_3CH_3$,

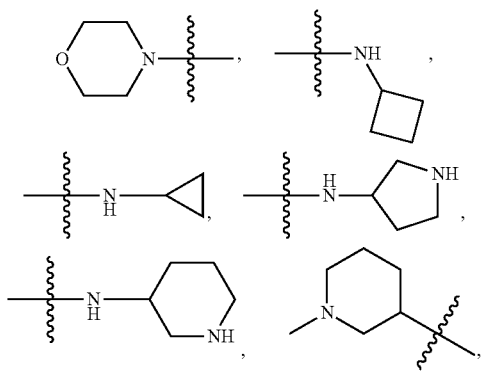

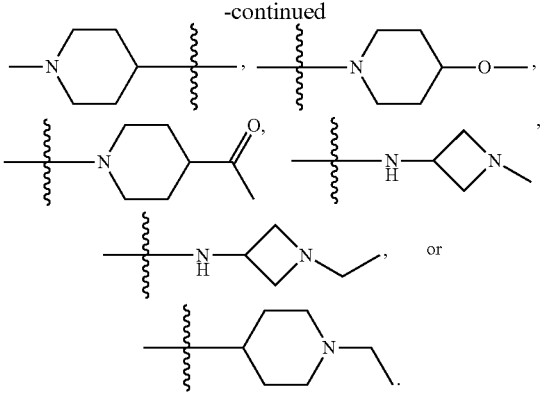

4. The compound of claim 1, wherein $R_4$ is $—OCH_3$.

5. The compound of claim 1, wherein $R_5$ is H.

6. The compound of claim 1, wherein $R_7$ is

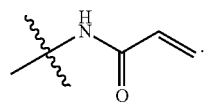

7. The compound of claim 1, wherein the compound is

N-(5-(5-chloro-4-(2-(2-(dimethylamino)-2-oxoacetyl) phenylamino)pyrimidin-2-ylamino)-4-methoxy-2-(4-methylpiperazin-1-yl)phenyl)acrylamide;

N-(5-(5-chloro-4-(2-(2-(methylamino)-2-oxoacetyl)phenylamino)pyrimidin-2-ylamino)-4-methoxy-2-(4-methylpiperazin-1-yl)phenyl)acrylamide; or N-(5-(5-chloro-4-(2-(2-(dimethylamino)-2-oxoacetyl) phenylamino)pyrimidin-2-ylamino)-4-methoxy-2-(1-methylpiperidin-4-yl)phenyl)acrylamide.

8. A pharmaceutical composition comprising the compound of claim 1 and a pharmaceutically acceptable excipient.

9. The pharmaceutical composition according to claim 8, wherein a weight ratio of said compound to said excipient is from about 0.0001 to about 10.

* * * * *